US010300143B2

(12) United States Patent
Sengupta et al.

(10) Patent No.: US 10,300,143 B2
(45) Date of Patent: May 28, 2019

(54) COMPOSITIONS FOR TREATING CANCER AND METHODS FOR MAKING THE SAME

(71) Applicant: THE BRIGHAM AND WOMEN'S HOSPITAL, INC., Boston, MA (US)

(72) Inventors: Shiladitya Sengupta, Waltham, MA (US); Ashish Kulkarni, Waltham, MA (US); Poornima Rao, Waltham, MA (US); Bhaskar Roy, Belmont, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/722,831

(22) Filed: Oct. 2, 2017

(65) Prior Publication Data

US 2018/0125987 A1    May 10, 2018

Related U.S. Application Data

(62) Division of application No. 14/406,938, filed as application No. PCT/US2013/045893 on Jun. 14, 2013, now Pat. No. 9,789,193.

(60) Provisional application No. 61/689,950, filed on Jun. 15, 2012, provisional application No. 61/797,484, filed on Dec. 7, 2012.

(51) Int. Cl.
*A61K 45/06* (2006.01)
*A61K 47/54* (2017.01)
*A61K 47/55* (2017.01)

(52) U.S. Cl.
CPC .............. *A61K 47/55* (2017.08); *A61K 45/06* (2013.01); *A61K 47/554* (2017.08)

(58) Field of Classification Search
CPC ......... A61K 45/06; A61K 47/54; A61K 47/55
See application file for complete search history.

(56) References Cited

U.S. PATENT DOCUMENTS

| | | | |
|---|---|---|---|
| 6,218,367 | B1 | 4/2001 | Jacob |
| 9,107,824 | B2 | 8/2015 | Pilkiewicz et al. |
| 2005/0043239 | A1 | 2/2005 | Douangpanya et al. |
| 2005/0209174 | A1 | 9/2005 | McChesney et al. |
| 2006/0003976 | A1 | 1/2006 | Zhang et al. |
| 2006/0079538 | A1 | 4/2006 | Hallahan et al. |
| 2010/0331290 | A1 | 12/2010 | Ansell et al. |

FOREIGN PATENT DOCUMENTS

| | | |
|---|---|---|
| CN | 1743337 A | 3/2006 |
| CN | 101631464 A | 1/2010 |
| CN | 101878024 A | 11/2010 |
| EP | 0237051 A2 | 9/1987 |
| EP | 1862470 A1 | 12/2007 |
| WO | 2008/109163 A1 | 9/2008 |
| WO | 2010/123931 A1 | 10/2010 |

OTHER PUBLICATIONS

Bradley et al., "Tumor Targeting by Covalent Conjugation og a Natural Fatty Acid to Paclitaxel", Clinical Cancer Research 7:3229-3238 (2001).
Fruman et al., "PI3Kδ Inhibitors in Cancer: Rationale and Serendipity Merge in the Clinic", Cancer Discovery 1(7):562-572 (2011).
Hennenfent et al., "Novel formulation of taxanes: a review. Old wine in a new bottle?", Annals of Oncology 17:735-749 (2006).
Kulkarni et al., "Supramolecular Nanoparticles That Target Phosphoinositide-3-Kinase Overcome Insulin Resistance and Exert Pronounced Antitumor Efficacy", Cancer Research 73(23):6987-6997 (2013).
Lin et al., "High-performance liquid chromatography analysis of a novel small-molecule, anti-cancer drug, Palomid 529, in human and mouse plasma and in mouse tissue homogenates", Journal of Chromatography B 879:3823-3831 (2011).
SciFinder search for compounds taught in the Chinese document CN 174337.
Sengupta et al., "Cholesterol-tethered platinum II-based supramolecular nanoparticle increases antitumor efficacy and reduces nephrotoxicity", Proceedings of the National Academy of Sciences 109(28):11294-11299 (2012).
Stevens P., "An Approach to Drug Formulation and Targeting: Liposmes and Lipid Nanoparticles for Folate Receptor Targeting", Doctoral Dissertation, The Ohio State University (2005). (126 pages).
Sutton et al., "Functionalized Micellar Systems for Cancer Targeted Drug Delivery", Pharmaceutical Research 24(6):1029-1046 (2007).
Taniguchi et al., "Phosphoinositide 3-kinase regulatory subunit p85α suppresses insulin action via positive regulation of PTEN", Proceedings of the National Academy of Sciences 103(32):12093-12097 (2006).
Wang et al., "Self-assembled nanoparticles of cholesterol-modified O-carbozymethyl chitosan as a novel carrier for paclitaxel", Nanotechnology 19:145101 (2008). (8 pages).
Watanabe K., "Development of drug delivery system with dendritic poly (L-lysine)", Doctoral Dissertation of Division of Life Engineering, Graduate School of System Life Sciences Kyushu University 7-10 (2012).
Yuan et al., "A Stabilized Demethoxyviridin Derivative Inhibits P13 kinase", Bioorganic & Medicinal Chemistry Letters 19(15):4223-4227 (2009).
Zhang et al., "C-Src-mediated RANKL-induced breast cancer cell migration by activation of the ERK and Akt pathway", Oncology Letters 3:395-400 (2012).
Borrelli et al., "New class of squalene-based releasable nanoassemblies of paclitaxel, podophyllotoxin, camptothecin and epothilone A", European Journal of Medicinal Chemistry 85:179-190 (2014).
Gulati et al., "Lipophilic drug derivatives in liposomes", International Journal of Pharmaceutics 165:129-168 (1998).

(Continued)

*Primary Examiner* — Shirley V Gembeh
(74) *Attorney, Agent, or Firm* — David S. Resnick; Nixon Peabody LLP

(57) ABSTRACT

Described herein are compositions and methods relating to chemotherapeutic agent conjugates and the treatment of cancer.

16 Claims, 45 Drawing Sheets
Specification includes a Sequence Listing.

(56) References Cited

OTHER PUBLICATIONS

Sarpietro et al., "Squalenoyl prodrug of paclitaxel: Synthesis and evaluation of its incorporation in phospholipid bilayers", International Journal of Pharmaceutics 436:135-140 (2012).
Stevens et al., "A Folate Receptor—Targeted Lipid Nanoparticle Formulation for a Lipophilic Paclitaxel Prodrug", Pharmaceutical Research 21(12):2153-2157 (2004).
Atta-Ur-Rahman et al., "PI3KS as a Link Betweeen Inflammation and Angiogenesis", Anti-angiogenesis Drug Discovery and Development 1:75-80 (2011).
Gharbi et al., "Exploring the specificity of the PI3K family inhibitor LY294002", Biochem J 404: 15-21 (2007).

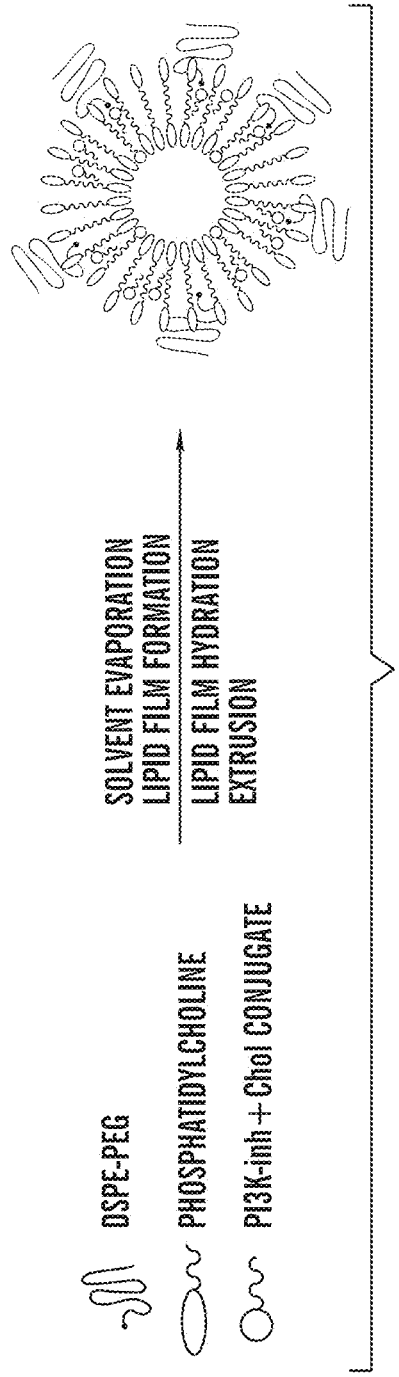
FIG. 1C
FIG. 1D
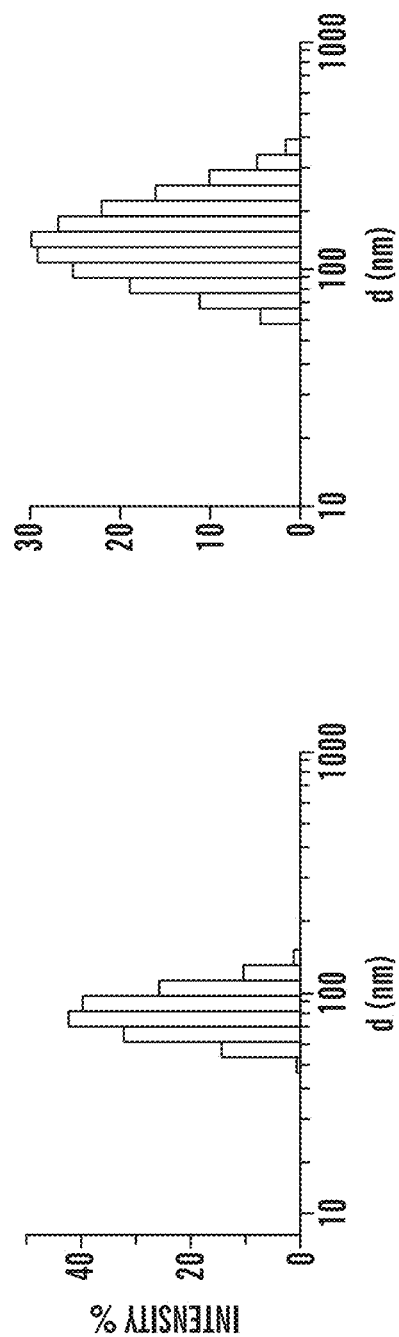
FIG. 1E

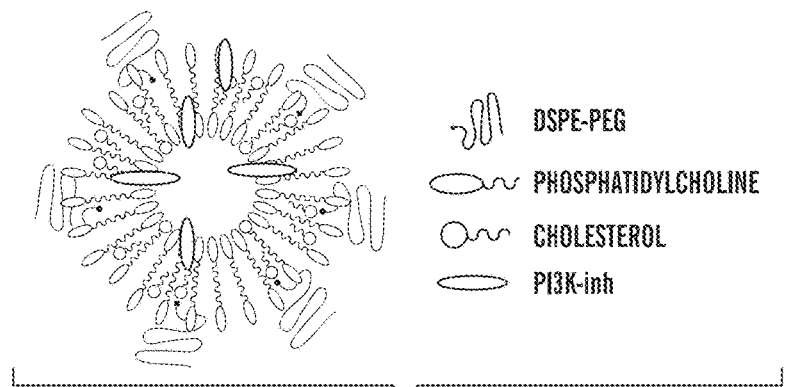
*FIG. 8A*
| NO. | PI-103 (mg) | CHOLESTEROL (mg) | PC (mg) | DSPE-PEG (mg) | SIZE (nm) | % INCORPORATION |
|---|---|---|---|---|---|---|
| I | 1 | 5 | 10 | 1 | 110 | 2 |
| II | 1 | 1.2 | 6.5 | 2.2 | 275 | 14 |
| III | 1 | 1 | 5 | 10 | 296 | 30 |
*FIG. 8B*
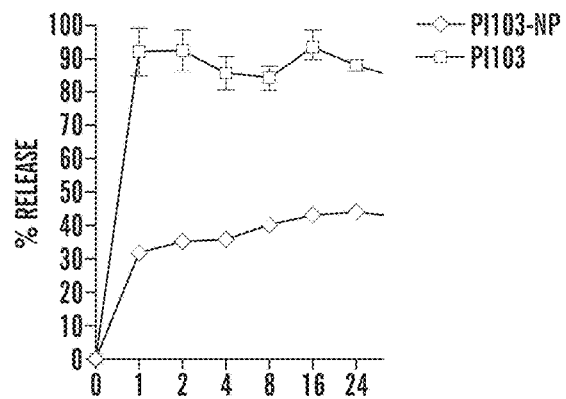
*FIG. 8C*

| Composition (mol%) | | | Size, nm | PDI | loading (%) | Zeta potential |
|---|---|---|---|---|---|---|
| Pacli-chol | DSPE-PEG | PC | | | | |
| 20 | 1 | 79 | 210 | 0.189 | 35 | -40.4±4.46 |
| 20 | 10 | 70 | 170±5 | 0.391 | 55±5 | -36.1±4.46 |
| 20 | 20 | 60 | 180±10 | 0.185 | 75±8 | -20.8±4.47 |
| 20 | 30 | 50 | 180±10 | 0.188 | 88±4 | -20±7.01 |
| 25 | 20 | 55 | 185 | 0.287 | 76 | -23.9±4.94 |
| 25 | 30 | 45 | 170±10 | 0.324 | 62±2 | -15.3±4.27 |
| 30 | 10 | 60 | 150±25 | 0.675 | 30±20 | -40.8±6.30 |
| 30 | 20 | 50 | 132 | 0.303 | 40 | -22.5±7.63 |

FIG. 21C

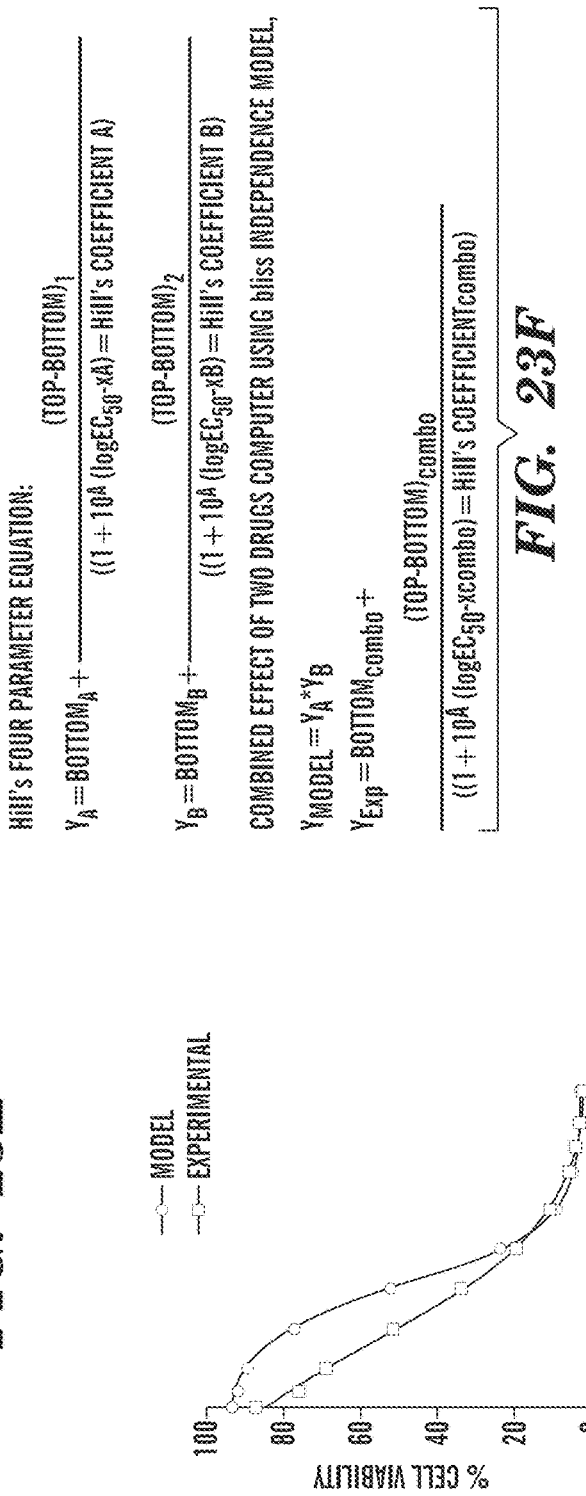

| Parameters | Pacli-chol NPs | PI103 | Combo |
|---|---|---|---|
| EC$_{50}$, nM | 51.97 | 80.27 | 22.42 |
| Hill's cofficient | -1.095 | -1.067 | -0.9106 |
| Bottom | 18.66 | 8.502 | 3.463 |
| Top | 103.8 | 89.32 | 92.73 |
| Log EC$_{50}$ | 1.716 | 1.901 | 1.325 |

COMPOSITIONS FOR TREATING CANCER AND METHODS FOR MAKING THE SAME

CROSS-REFERENCE TO RELATED APPLICATIONS

This application is a Divisional Application of U.S. application Ser. No. 14/406,938 filed Dec. 10, 2014, which is a 35 U.S.C. § 371 National Phase Entry Application of International Application No. PCT/US2013/045893 filed Jun. 14, 2013, which designates the U.S., and which claims benefit under 35 U.S.C. § 119(e) of U.S. Provisional Application Nos. 61/689,950 filed Jun. 15, 2012 and 61/797,484 filed Dec. 7, 2012, the contents of each of which are incorporated herein by reference in their entireties.

GOVERNMENT SUPPORT

This invention was made with federal funding under Grant Nos. W81XWH-07-1-0482 and W81XWH-09-0698/700 awarded by the Department of Defense and 1R01CA135242-01A2 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Oct. 2, 2017, is named 043214-090290-DIV and is 1,279 bytes in size.

TECHNICAL FIELD

The compositions and methods described herein relate to the technical field of drug delivery and the treatment of cancer.

BACKGROUND

According to the World Health Organization, mortality due to cancer is expected to increase from 7.6 million in 2008 to 12 million deaths in 2030 (1). To address this growing problem, two emerging paradigms that are driving the evolution of newer treatment strategies are: (i) better understanding of oncogenic drivers, leading to the development of molecularly 'targeted' therapeutics (2-3); and, (ii) the use of nanotechnology to deliver drugs specifically to the tumor, thereby improving therapeutic index (4-5). However the interface between these two paradigms, which can offer unique opportunities for improving cancer chemotherapy, currently remains largely underexplored.

SUMMARY

The level of a chemotherapeutic agent which is necessary in order to effectively treat a cancer is often well above the level at which dangerous side effects are likely to occur. The inventors have designed conjugates, and compositions comprising those conjugates, which increase the level of chemotherapeutic agent which is delivered to the tumor while reducing the accumulation of the chemotherapeutic in other tissues, e.g. the liver. These conjugates overcome the difficulties typically encountered with nanoformulation of chemotherapeutic agents, which limit the entrapment efficiency or introduce sub-optimal release kinetics.

In one aspect, described herein is a conjugate comprising a chemotherapeutic agent conjugated to cholesterol. In some embodiments, the conjugate is an amphiphile. In some embodiments, the agent is conjugated to cholesterol via a linker. In some embodiments, the linker is selected from the group consisting of: —O—, —S—, —S—S—, —NR$^1$, —C(O)—, —C(O)O—, —C(O)NR$^1$, —SO—, —SO$_2$—, —SO$_2$NR$^1$—, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl; wherein one or more methylenes can be interrupted or terminated by O, S, S(O), SO$_2$, N(R$^1$)$_2$, C(O), C(O)O, C(O)NR$^1$, cleavable linking group, substituted or unsubstituted aryl, substituted or unsubstituted heteroaryl, substituted or unsubstituted heterocyclic, and wherein R$^1$ is hydrogen, acyl, aliphatic or substituted aliphatic. In some embodiments, the linker is C(O), C(O)CH$_2$CH$_2$C(O), or C(O)NH(CH$_2$)$_2$NHC(O)(CH$_2$)$_2$C(O).

In some embodiments, the chemotherapeutic agent is a PI3K inhibitor. In some embodiments, the PI3K inhibitor is selected from the group consisting of PI103; PI828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136. In some embodiments, the PI3K inhibitor is selected from the group consisting of PI103 and PI828. In some embodiments, the conjugate can have the structure of Formula I:

FORMULA I
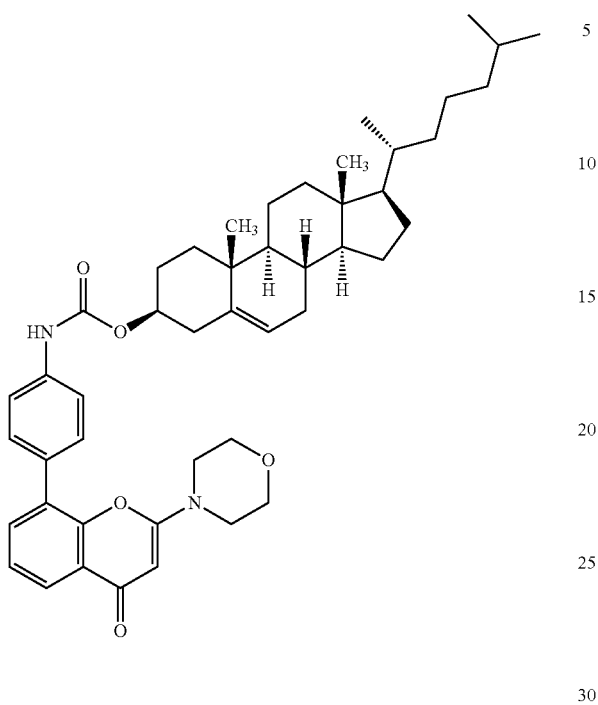
In some embodiments, the conjugate can have the structure of Formula II:
FORMULA II
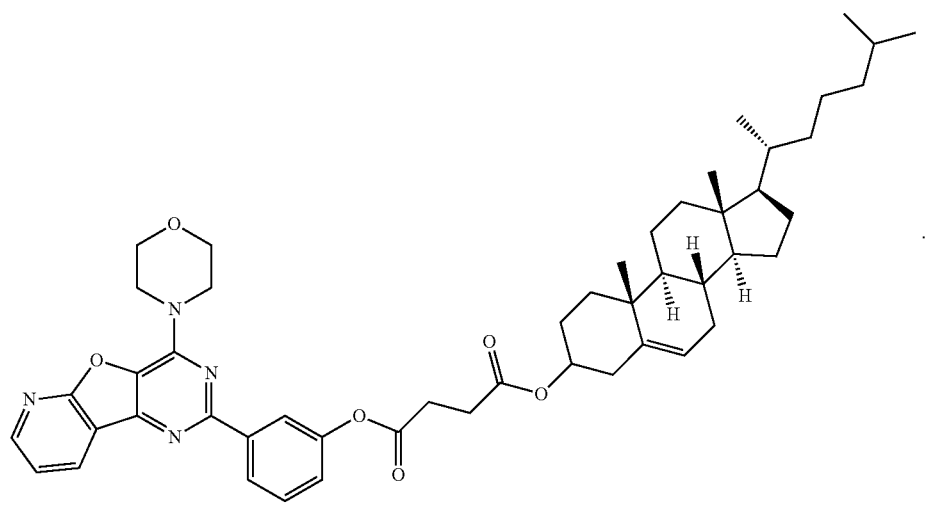
In some embodiments, the chemotherapeutic agent is a taxane. In some embodiments, the taxane is paclitaxel or docetaxel. In some embodiments, the conjugate can have the structure of Formula III:

FORMULA III

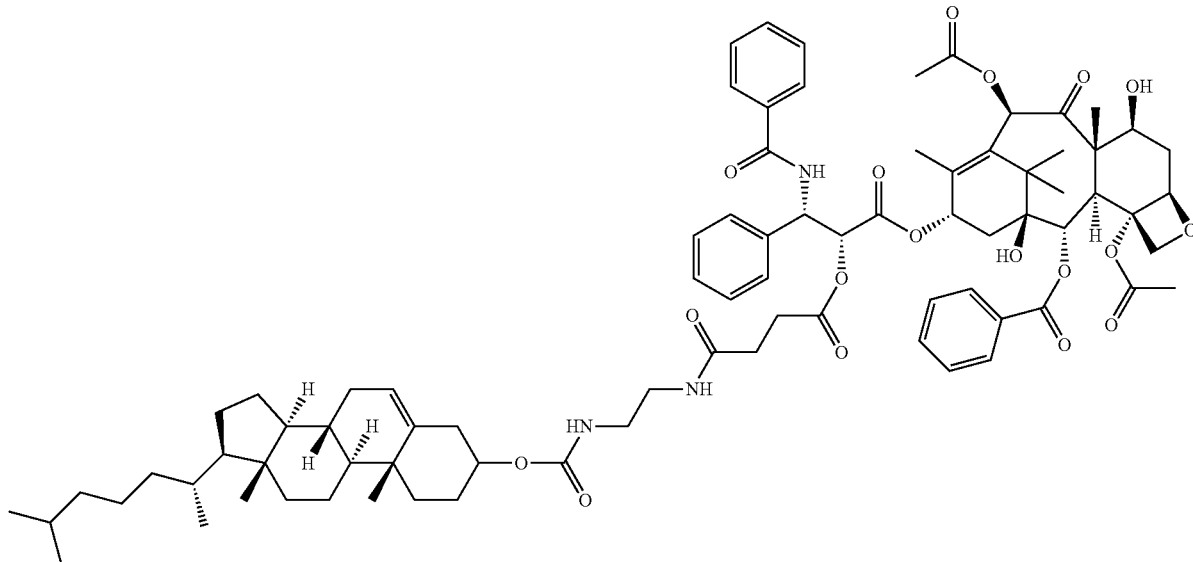

In one aspect, described herein is a composition comprising a conjugate as described herein. In some embodiments, the composition comprises about 1% to about 99% (w/w) of the conjugate. In some embodiments, the composition further comprises a lipid in addition to the conjugate. In some embodiments, the composition comprises about 1% to about 99% (w/w) of the lipid. In some embodiments, the composition comprises the conjugate and the lipid in about 10:1 to about 1:10 ratio. In some embodiments, the lipid is a lipid conjugated with polyethylene glycol (PEG). In some embodiments, the PEG conjugated lipid is selected from the group consisting of PEG conjugated diacylglycerols and dialkylglycerols, PEG-conjugated phosphatidyletha-nolamine and phosphatidic acid, PEG conjugated ceramides, PEG conjugated dialkylamines, PEG conjugated 1,2-diacy-loxypropan-3-amines, and any combinations thereof. In some embodiments, the PEG conjugated lipid is 1,2-dis-tearoyl-sn-glycem-3-phosphoethanolamine-N-[amino(poly-ethylene glycol)-2000] (DSPE-PEG2000).

In some embodiments, the composition further comprises a phospholipid. In some embodiments, the composition comprises about 1% to about 99% (w/w) of the phospholipid. In some embodiments, the composition comprises the conjugate and the phospholipid in about 10:1 to about 1:10 ratio. In some embodiments, the composition comprises the phospholipid and the lipid in about 10:1 to about 1:10 ratio. In some embodiments, the phospholipid is selected from phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, and any combinations thereof. In some embodiments, the phospholipid is selected from the group consisting of phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and any combinations thereof. In some embodiments, the phosphatidylcholine is L-a-phosphatidylcholine.

In some embodiments, the composition can further comprise a targeting agent. In some embodiments, the targeting agent is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof. In some embodiments, the targeting agent is iRGD.

In some embodiments, the composition comprises two or more different conjugates of any of claims 1-13. In some embodiments, the composition further comprises an anticancer agent in addition to the conjugate. In some embodiments, the anticancer agent is a platinum compound, paclitaxel; carboplatin; bortezomib; vorinostat; rituximab; temozolomide; rapamycin; an alkylating agent; cyclophosphamide; an alkyl sulfonate; busulfan; improsulfan; pipo-sulfan; an aziridine; an ethylenimine; a methylamelamine;

an acetogenin; a camptothecin; a cryptophycin; a nitrogen mustard; a nitrosurea; an antibiotic; a enediyne antibiotic; a bisphosphonate; doxorubicin; a mitomycin; an anti-metabolite; a folic acid analogue; a purine analog; a pyrimidine analog; an androgen; an anti-adrenal; an epothilone; a maytansinoid; a trichothecene; gemcitabine; 6-thioguanine; mercaptopurine; methotrexate; vinblastine; etoposide; ifosfamide; mitoxantrone; vincristine; vinorelbine; novantrone; teniposide; edatrexate; daunomycin; aminopterin; xeloda; ibandronate; irinotecan; a topoisomerase inhibitor; a retinoid; capecitabine; combretastatin; leucovorin; lapatinib; and erlotinib. In some embodiments, the platinum compound is of formula (IV):

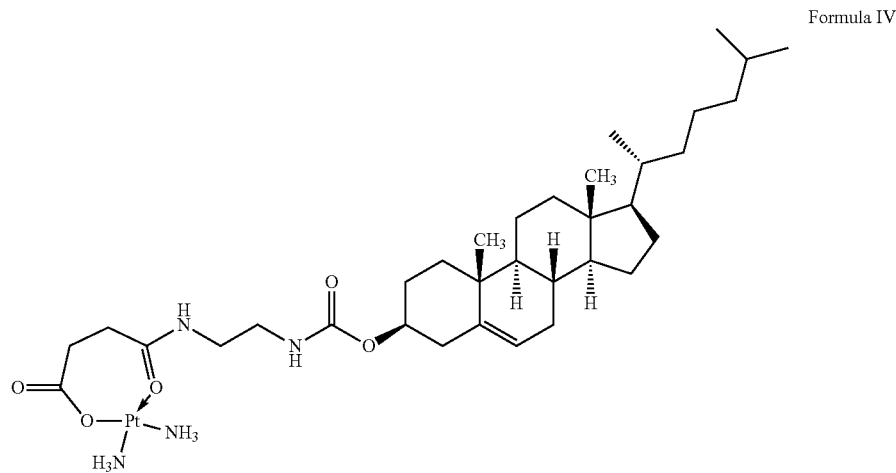

Formula IV

In some embodiments, the composition further comprises a neutral lipid, a cationic lipid, an anionic lipid, an amphiphilic lipid, a sterol, or a programmable fusion lipid. In some embodiments, the composition comprises the conjugate, a PEG conjugated lipid, and a phospholipid. In some embodiments, the PEG conjugated lipid is DSPE-PEG2000 and the phospholipid is phosphatidylcholine. In some embodiments, the composition comprises the conjugate, the PEG conjugated lipid, and the phospholipid in ratio from about 10-0.1:10-0.1:10-0.1. In some embodiments, the ratio is about 1.4:1:3 or about 10:5:1. In some embodiments, the composition is a nanoparticle. In some embodiments, the nanoparticle is about 5 nm to about 500 nm in diameter. In some embodiments, the nanoparticle is less than about 200 nm in diameter.

In one aspect, described herein is a pharmaceutical composition comprising the composition as described herein, and optionally, a pharmaceutically acceptable carrier.

In one aspect, described herein is a method of treating cancer, comprising, administering a composition as described herein to a patient in need of treatment for cancer. In some embodiments, the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer. In some embodiments, the subject has been determined to have tumor cells with aberrant PI3K, e.g. aberrant activity and/or levels of PI3K or PI3K signaling. In some embodiments, the method further comprises co-administering one or more additional anti-cancer therapy to the patient. In some embodiments, the additional therapy is selected from the group consisting of surgery, chemotherapy, radiation therapy, thermotherapy, immunotherapy, hormone therapy, laser therapy, anti-angiogenic therapy, and any combinations thereof. In some embodiments, the additional therapy comprises administering an anti-cancer agent to the patient.

In one aspect, described herein is a method of reducing blood glucose levels, comprising administering a composition as described herein to a subject in need of a reduction of blood glucose levels.

BRIEF DESCRIPTION OF THE DRAWINGS

FIGS. 1A-1I: Synthetic scheme showing conjugation of (FIG. 1A) PI-828 and (FIG. 1B) PI103 to cholesterol via carbamate and ester linkages respectively; (FIG. 1C) Schematic representation shows assembly of supramolecular nanoparticles (SNPs) from phosphatidylcholine (PC), PI103/PI828-cholesterol conjugate and DSPE-PEG; Distribution of hydrodynamic diameter of (FIG. 1D) PI828-SNPs and (FIG. 1E) PI103-SNPs measured using dynamic light scattering; (FIG. 1F) High resolution cryo-transmission electron microscopy image of PI103-SNPs (Scale Bar=100 nm); (FIG. 1G) Physical stability of PI103-SNPs during storage condition at 4° C. as measured by changes in size. Inset shows changes in Zeta potential of nanoparticles at 4° C.; (FIG. 1H) Release kinetics of PI103 from SNPs in PBS, pH 7.4, and in 4T1 breast cancer cell lysate. (FIG. 1I) Release kinetics of PI828 from SNPs in PBS, pH 7.4 (blue line), and in lysates from 4T1 cells (red line) and PI3K-overexpressing 4306 ovarian cancer cells (green line). Data shown are mean±SEM (at least triplicates at each condition).

(FIG. 2O) Effect of treatment with PI828 or PI828-SNPs (5.0 and 7.0 μM) on phosphoAkt levels at 36 hours post-treatment.

(FIG. 3A) In Vivo efficacy of PI103 or PI103-SNP in syngenic 4T1 breast cancer mouse model. The mice were given 3 injections every other day of PBS (control group), of free PI013, PI103-SNP or iRGD-coated PI103-SNP all 5 mg/kg dose equivalent of PI103. The first day of treatment was considered as Day 1. Tumor volumes were measured every other day for 11 days. The endpoint was tumor size >2000 cm3, or tumor ulceration or necrosis, or death of the animal. (FIG. 3B) Distribution of tumor volume increment in different groups at day 11 after the 1 injection. Treatment with PI103-SNP and iRGD-coated PI103-SNP was statistically more effective than treatment with free PI103; (FIG. 3C) Pictorial representation of tumor volume from each group; (FIG. 3D) Graph showing the effect of PI103 on insulin tolerance. The mice were injected with a single dose of empty SNPs, Free PI-103 (5 mg/kg) and PI103-SNP (5 mg/kg). One hour later, the mice were injected with insulin (0.75 units/kg). Blood glucose levels were measured before and 45 min after the insulin injection. Results are mean±SEM (n=5). Statistical significance was determined by student t-test. **p<0.01 (FIG. 3E) Expression of phospho mTOR, total mTOR, phospho AKT, total AKT, actin, phospho 4EBP and total 4EBP in tumors 72 hours after single dose injection of free PI103 or PI103-SNP at 5 mg/kg dose in the 4T1 model.

(FIG. 4A) Bioluminescence quantification indicates a significantly decreased tumor luciferase signal in mice treated with free PI103, PI103-SNP, and iRGD-PI103-SNP compared to the vehicle-treated group (p<0.05, one-way ANOVA analysis) after 3 treatments. Following 5 treatments, bioluminescence quantification indicates that the response to PI103-SNP was significantly higher than to free PI103 (p<0.01, one-way ANOVA analysis); (FIG. 4B) Representative K-ras$^{LSL/+}$/Pten$^{fl/fl}$ tumors excised from animals treated with free PI-103, PI103-SNP, and iRGD-PI103-SNP; (FIG. 4C) Drug toxicity assessed by measuring body weight. Daily recordings after 5 treatments indicate no difference in body weight of the treatment groups; (FIG. 4D) PI3K/mTOR pathway markers were assessed western blotting in K-ras$^{LSL/+}$/Pten$^{fl/fl}$ tumors treated with vehicle, or with free PI103, PI103-SNP, and iRGD-PI103-SNP, each at 5 mg/kg of PI103. Inhibition of mTOR substrates by PI103-SNP and iRGD-PI103-SNP was much stronger than in the free drug group.

FIGS. 8A-8F (FIG. 8A) Representation shows PI103 encapsulated nanoparticles synthesized by self-assembly from phosphatidylcholine (PC), cholesterol conjugate and DSPE-PEG; (FIG. 8B) Table shows effect of different nanoparticle formulations on size and incorporation efficiency of PI-103; (FIG. 8C) Release kinetics studies of PI103 as a free drug and from PI103 encapsulated nanoparticle; MTS assay showing the effect of free PI-103 or PI103 encapsulated nanoparticle at different concentrations on cell viability of 4T1 cells (FIG. 8D) at 48 h; (FIG. 8E) Expression of phospho AKT and Total AKT in 4T1 cells at 48 hours after treatment with either 5 μM of Free PI103 or PI-103 encapsulated nanoparticle; (FIG. 8F) Physical stability of PI103 encapsulated nanoparticles at different time intervals as shown by DLS graphs.

(FIG. 9B) Expression of piAKT in tumor after 72 hours of treatment with either free or nanoparticle of PI828 in 5 mg/Kg dose.

FIG. 10A depicts a scheme for synthesis of cholesterol-cisplatin conjugate from cholesteryl chloroformate. Schematic representation shows synthesis of SACNs by self-assembly from PC, cholesterol-cisplatin conjugate, and DSPE-PEG. FIG. 10B depicts high-resolution cryo-TEM image of SACNs at lower magnification (Upper) and magnified image (Lower). (Scale bar, Upper, 500 nm). FIG. 10C depicts a graph of the distribution of hydrodynamic diameter of SACNs measured using dynamic light scattering. FIG. 10D depicts a graph of the pH-dependent release of platinum from SACNs as quantified over a 120-h period.

FIGS. 11A-11C depict graphs of cell viability of (11A) LLC, (11B) 4T1, and (11C) 7404-CP20 cell lines, respectively, after 48-h incubation with increasing concentrations of cisplatin, carboplatin, and SACNs. FIG. 11D depicts FACS analysis results demonstrating that treatment with SACNs induces cell death by apoptosis. Representative FACS distribution of 4T1 cells treated with carboplatin, cisplatin, and SACNs at 1 μM Pt concentration. The cells were incubated for 24 h, following which they were labeled with Annexin-V FITC and counter-stained with propidium iodide. Each quadrant represents the percentage of cells in early apoptosis (Lower Right), late apoptosis (Upper Right), necrosis (Upper Left), and healthy cells (Lower Left). Data shown are mean±SE from n=3 independent experiments. FIG. 11E depicts a graph of Pt levels in 7404-CP20 cells treated with cisplatin or SACNs (20 μM Pt concentration). Cells incubated with similar concentration of SACNs at 4° C. to inhibit energy-dependent endocytosis exhibit lower intracellular Pt concentrations (*P<0.05, **P<0.01, ANOVA, Newman-Keuls post hoc test).

FIG. 12A depicts a graph of body weight loss of animals with increasing doses of cisplatin or SACNs (Cisplatin NP). Maximum tolerated dose is calculated at 20% body weight loss. FIG. 12B depicts a graph demonstrating that the change in tumor volume in different treatment groups in 4T1 murine breast cancer model following a single dose of platinum chemotherapy at the MTD platinum dose of cisplatin. FIG. 12C depicts a graph of Kaplan-Meier curve of the effect of different treatments on survival at MTD platinum dose of cisplatin (P=0.0189 Logrank test for trend). FIGS. 12D-12F depict the multiple-dose effects of treatment on 4T1 breast cancer growth. Cells were implanted subcutaneously on day 0. Mice were treated with PBS, carboplatin (3 mg/kg), cisplatin (3 mg/kg and 1 mg/kg), and SACNs (3 mg/kg and 1 mg/kg) (n=4, doses are Pt equivalent) on days 9, 11, and 13 posttumor implantation. Upper row shows representative images of excised tumors, and Lower row shows tumor cross sections processed for TUNEL as marker for apoptosis. Images were captured using a Nikon Ti epifluorescence microscope at 20× magnification to capture a large view field. FIG. 12D depicts a graph of growth curves of the effect of the different multiple-dose treatments on tumor volume. FIG. 12E depicts a graph of the change in body weight of animals in different treatment groups. FIG. 12F depicts a graph of Kaplan-Meier curves of the effect of different treatments on survival (P=0.0022, Logrank Mantel-Cox test).

FIG. 13A depicts a bar graph of the weight of excised kidney in different treatment groups. FIG. 13B depicts a graph of tissue distribution of platinum in different treatment groups as determined by inductively coupled plasma-MS. *P<0.05, **P<0.01 vs. cisplatin (3 mg/kg)-treated group (ANOVA followed by Newman-Keuls post hoc test).

FIG. 19A depicts a graph of bioluminescence quantification indicating a significantly decreased tumor luciferase signal in mice treated with SACNs compared with vehicle or cisplatin. Quantification of bioluminescence was achieved by using the Living Image Software 3.1™. Data shown are mean±SE of n=minimum of three animals per group. *P<0.05 (ANOVA followed by Newman-Keuls post hoc test). FIG. 19B depicts a graph of representative tissue distribution of platinum in different treatment groups as determined by ICP-MS shows preferential accumulation of SACNs in tumor vs. kidney.

FIGS. 21A-21G depict the synthesis and characterization of Pacli-chol nanoparticles. FIG. 21A depicts a scheme for synthesis of paclitaxel cholesterol conjugate with acid labile linker. FIG. 21B depicts a schematic representation shows synthesis of Pacli-chol nanoparticles by self-assembly from phosphatidylcholine. Paclitaxel cholesterol conjugate and DSPE-PEG. FIG. 21C depicts a table of optimization of size and loading of the nanoparticles by using different molar ratios of Paclitaxel cholesterol conjugate, phosphatidylcholine and DSPE-PEG. The change in size, loading, Polydispersity Index and Zeta potential is shown. FIG. 21D depicts a high resolution cryo-transmission electron microscopy image of Pacli-chol nanoparticles; FIG. 21E depicts a graph of distribution of hydrodynamic diameter of nanoparticles measured using dynamic light scattering (DLS). FIG. 21F depicts a graph of in vitro release of paclitaxel or paclitaxel cholesterol from (1) free paclitaxel nanoparticles in PBS, pH 7.4 (Triangles), (2) Nanoparticles synthesized using 1% DSPE-PEG (Triangles), (3) Nanoparticles with 30% DSEP-PEG in PBS, pH 7.4 (squares) and (4) Nanoparticles with 30% DSPE-PEG in 4T1 cell lysate (Circles). Data represents the mean±SE (n=3). FIG. 21G depicts a graph of physical stability of Pacli-chol nanoparticles during storage at 4° C. Mead particle size changes were measured using DLS.

FIGS. 22A-22B depict graphs of cell viability of (FIG. 22A) 4T1 and (FIG. 22BB) MDA-MB-231 cell lines respectively after 72 h incubation with increasing concentrations of free paclitaxel and pacli-chol nanoparticles with 1% DSPE-PEG, 10% DSPE-PEG, 20% DSPE-PEG and 30% DSPE-PEG. FIG. 22C depicts the results of western blot analysis showing cleaved caspase-3 and 0-actin expression levels after 6 h of treatment with control, Pacli-chol nanoparticles with 1% DSPE-PEG and 30% DSPE-PEG. FIGS. 22D-22F depict graphs of cell viability of (FIG. 22D) 411, (FIG. 22E) MDA-MB-431 and (FIG. 22F) 4306 cell lines respectively after 72 h incubation with increasing concentrations of free paclitaxel and Pacli-chol nanoparticles with 30% DSPE-PEG.

FIGS. 23A-23H demonstrate the in vitro characterization of Pacli-chol nanoparticles in combination with PI3K inhibitor PI103. FIG. 23A depicts the results of western blot analysis showing Phospho-Akt, Total-Akt and 13-actin expression levels at different time intervals after treatment with 50 nM Pacli-chol nanoparticles in 4T1 cell lines. FIG. 23B depicts changes in expression levels of Phospho-Akt in 411 cells after treatment with 50 nM of Pacli-chol nanoparticles in absence and presence of 50 nM of PI-103. FIGS. 23C-23D depict graphs of in vitro cell viability assay of Pacli-chol nanoparticles and PI-103 alone and in combination in 4T1 cell lines at (FIG. 23C) 1:1 and (FIG. 23D) 1:2 molar ratios. FIG. 23E depicts the formula of combination index to determine the effect of two drugs in combination. FIG. 23F depicts four parameter Hills Equation used to obtain the EC50 of individual drugs and in combination. Bliss independence model is used to predict the additive effect of two drugs in combination treatment. FIG. 23G depicts a graph comparison of predicted additive effect of drugs in combination to the experimental data. The experimental data is below the additive curve showing the drugs have synergistic effect. FIG. 23H depicts a table of the four parameter in Hill's equation obtained the experimental result using Graph pad prism.

FIGS. 24A-24C demonstrate the in vivo antitumor activity of Pacli-chol nanoparticles in combination with PI-103 in 411 breast cancer model. FIGS. 24A-24B depict the multiple-dose effects of treatment on 4T1 breast cancer growth. Cells were implanted subcutaneously on day zero. Mice were treated with PBS, Paclitaxel (3 mg/kg and 10 mg/kg), PI-103 (3 mg/kg), Pacli-Chol Nanoparticles (3 mg/kg and 10 mg/kg), Paclitaxel+PI-103 (3 mg/kg each), Pacli-chol nanoparticles+PI-103 (3 mg/kg each), iRGD Pacli-chol nanoparticles (3 mg/kg) and iRGD Pacli-chol nanoparticles+PI-103 (3 mg/kg each) (n=5, doses are Paclitaxel equivalent) on days 10th, 14th and 18th posttumor implantation. FIG. 24A depicts images of excised tumors, FIG. 24B presents a graph of tumor volumes. FIG. 24C depicts a graph of the change in body weight of animals in different treatment groups. Statistical analysis were performed with ANOVA. Error bars denote mean±SEM. *P<0.05, P<0.01, *P<0.001. ***—iRGD Pacli-Chol nanoparticles+PI103 versus free Paclitaxel (3 mg/kg) or free PI-103 (3 mg/kg).

DETAILED DESCRIPTION

Figure 1A:
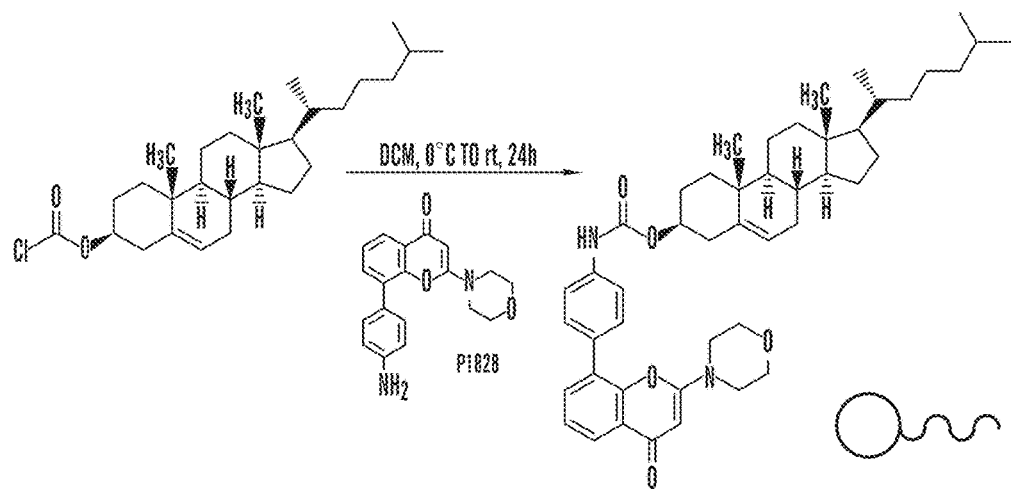

In one aspect, the disclosure provides a conjugate comprising a chemotherapeutic agent covalently linked with a lipid. The term "lipid" as used herein means a substance that is soluble in organic solvents and includes, but is not limited to, oils, fats, sterols, triglycerides, fatty acids, phospholipids, and the like. The chemotherapeutic agent and the lipid can be covalently conjugated with each other using a reactive functional group present in their respective structures. The term "reactive functional group" refers to a functional group that is capable of reacting with another functional group. Exemplary reactive functional groups include, but are not limited to, hydroxyls, amines, thiols, thials, sulfinos, carboxylic acids, amides, and the like. The reactive functional group on the lipid and the chemotherapeutic agent can be the same or different. In some embodiments, the reactive group on the lipid is a hydroxyl, an amine, a thiol, or a carboxylic acid. In some embodiments, the reactive group on the chemotherapeutic agent is a hydroxyl, an amine, a thiol, or a carboxylic acid.

Without limitations the lipid can be selected from the group consisting of sterol lipids, fatty acids, fatty alcohols, glycerolipids (e.g., monoglycerides, diglycerides, and tri-glycerides), phospholipids, glycerophospholipids, sphingolipids, prenol lipids, saccharolipids, polyketides, and any combination thereof. The lipid can be a polyunsaturated fatty acid or alcohol. The term "polyunsaturated fatty acid" or "polyunsaturated fatty alcohol" as used herein means a fatty acid or alcohol with two or more carbon-carbon double bonds in its hydrocarbon chain. The lipid can also be a highly unsaturated fatty acid or alcohol. The term "highly polyunsaturated fatty acid" or "highly polyunsaturated fatty alcohol" as used herein means a fatty acid or alcohol having at least 18 carbon atoms and at least 3 double bonds. The lipid can be an omega-3 fatty acid. The term "omega-3 fatty acid" as used herein means a polyunsaturated fatty acid whose first double bond occurs at the third carbon-carbon bond from the end opposite the acid group.

In some embodiments, the lipid can be selected from the group consisting of cholesterol; 1,3-Propanediol Dicapry-late/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; Capmul MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (Capmul MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; and γ-Linolenic acid.

In some embodiments, the lipid is cholesterol. In some embodiments, the cholesterol can further comprise succinate and/or succinic acid for conjugating with the chemotherapeutic agent.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term chemotherapeutic agent is a broad one covering many chemotherapeutic agents having different mechanisms of action. Generally, chemotherapeutic agents are classified according to the mechanism of action. Many of the available agents are anti-metabolites of development pathways of various tumors, or react with the DNA of the tumor cells. There are also agents which inhibit enzymes, such as topoisomerase I and topoisomerase II, or which are antimiotic agents.

Chemotherapeutic agents include, but are not limited to, an aromatase inhibitor; an antiestrogen, an anti-androgen (especially in the case of prostate cancer) or a gonadorelin agonist; a topoisomerase I inhibitor or a topoisomerase II inhibitor; a microtubule active agent, an alkylating agent, an anti-neoplastic anti-metabolite or a platin compound; a compound targeting/decreasing a protein or lipid kinase activity or a protein or lipid phosphatase activity, a further anti-angiogenic compound or a compound which induces cell differentiation processes; a bradykinin 1 receptor or an angiotensin II antagonist; a cyclooxygenase inhibitor, a bisphosphonate, a heparanase inhibitor (prevents heparan sulphate degradation), e.g., PI-88, a biological response modifier, preferably a lymphokine or interferons, e.g. interferon $\gamma$, an ubiquitination inhibitor or an inhibitor which blocks anti-apoptotic pathways; an inhibitor of Ras oncogenic isoforms or a farnesyl transferase inhibitor; a telomerase inhibitor, e.g., telomestatin; a protease inhibitor, a matrix metalloproteinase inhibitor, a methionine aminopeptidase inhibitor, e.g., bengamide or a derivative thereof; a proteasome inhibitor, e.g., PS-341 (bortezomib/Velcade); agents used in the treatment of hematologic malignancies or FMS-like tyrosine kinase inhibitors; an HSP90 inhibitors; histone deacetylase (HDAC) inhibitors; mTOR inhibitors; somatostatin receptor antagonists; integrin antagonists; anti-leukemic compounds; tumor cell damaging approaches, such as ionizing radiation; EDG binders; anthranilic acid amide class of kinase inhibitors; ribonucleotide reductase inhibitors; S-adenosylmethionine decarboxylase inhibitors; antibodies against VEGF or VEGFR; photodynamic therapy; angiostatic steroids; ATI receptor antagonists; ACE inhibitors; and the like.

Other chemotherapeutic agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

In some embodiments, the chemotherapeutic agent can be a Phosphoinositide 3-kinase (PI 3-kinase or PI3K) inhibitor. Phosphoinositide 3-kinases are a family of related enzymes that are capable of phosphorylating the 3 position hydroxyl group of the inositol ring of phosphatidylinositol. They are also known as phosphatidylinositol-3-kinases. PI3Ks interact with the IRS (Insulin receptor substrate) in order to regulate glucose uptake through a series of phosphorylation events. The phosphoinositol-3-kinase family is composed of Class I, II and Class III, with Class I the only ones able to convert PI(4,5)P2 to PI(3,4,5)P3 on the inner leaflet of the plasma membrane.

Class I PI3K are heterodimeric molecules composed of a regulatory and a catalytic subunit; they are further divided between IA and IB subsets on sequence similarity. Class IA PI3K are composed of one of five regulatory p85α, p55α, p50α, p85β or p55γ subunit attached to a p110α, β or δ catalytic subunit. The first three regulatory subunits are all splice variants of the same gene (Pik3r1), the other two being expressed by other genes (Pik3r2 and Pik3r3, p85β and p55γ, respectively). The most highly expressed regulatory subunit is p85α, all three catalytic subunits are expressed by separate genes (Pik3ca, Pik3cb and Pik3cd for p110α, p110β and p110δ, respectively). The first two p110 isoforms (a and f) are expressed in all cells, but p110δ is primarily expressed in leukocytes and it has been suggested it evolved in parallel with the adaptive immune system. The regulatory p101 and catalytic p110γ subunits comprise the type IB PI3K and are encoded by a single gene each.

Class II comprises three catalytic isoforms (C2α, C2β, and C2γ), but unlike Classes I and III, no regulatory proteins. These enzymes catalyse the production of PI(3)P from PI (may also produce PI(3,4)P2 from PI(4)P). C2α and C2β are expressed throughout the body, however expression of C2γ is limited to hepatocytes. The distinct feature of Class II PI3Ks is the C-terminal C2 domain. This domain lacks critical Asp residues to coordinate binding of Ca2+, which suggests class II PI3Ks bind lipids in a Ca2+ independent manner. Class III are similar to II in that they bias the production of PI(3)P from PI, but are more similar to Class I in structure, as they exist as a heterodimers of a catalytic (Vps34) and a regulatory (p150) subunits. Class III seems to be primarily involved in the trafficking of proteins and vesicles.

As used herein, a "PI3K inhibitor" refers to an agent that inhibits the activity of PI3K, as measured by the level of phosphorylation of the 3 position hydroxyl group of the inositol ring of phosphatidylinositol, or as measured by the activity and/or phosphorylation (where increased phosphorylation indicates PI3K activity) of molecules downstream of PI3K. Examples of such downstream molecules are known in the art and can include, but are not limited to AKT, SGK, mTOR, GSK3β, PSD-95, S6, and 4EBP1. Methods of measuring the activity of PI3K, directly or indirectly are well known in the art, and include, by way of non-limiting example determining the level of phosphorylation of a molecule downstream of PI3K using phospho-isoform specific antibodies, which are commercially available (e.g. anti-phospho-AKT antibody, Cat No. ab66138 Abcam, Cambridge, Mass.).

In some embodiments, a PI3K inhibitor can be LY294002, PI103, and/or PI828. Further non-limiting examples of PI3K inhibitors can include wortmannin, demethoxyviridin, IC486068, IC87114, GDC-0941, perifosine, CAL101, PX-866, IPI-145, BAY 80-6946, BEZ235, P6503, TGR1202, SF1126, INK1117, BKM120, IL147, XL765, Palomid 529, GSK1059615, ZSTK474, PWT33597, TG100-115, CAL263, GNE-447, CUDC-907, and AEZS-136.

In some embodiments, the conjugate comprises a PI3K inhibitor covalently linked with cholesterol.

In some embodiments, the conjugate is of formula I or formula II:

FORMULA I

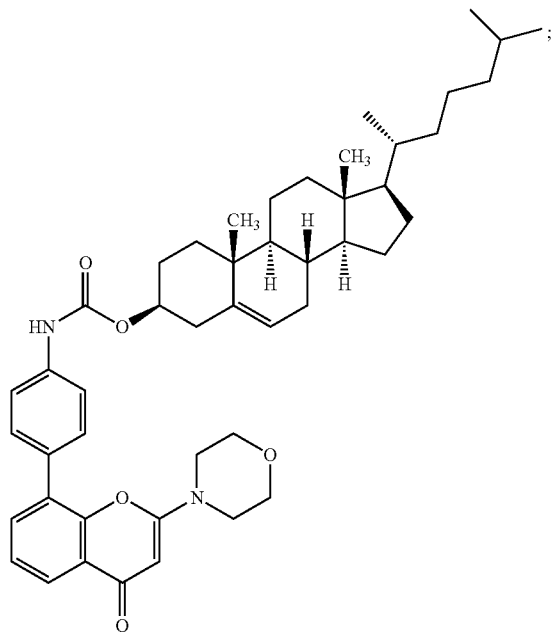

FORMULA II

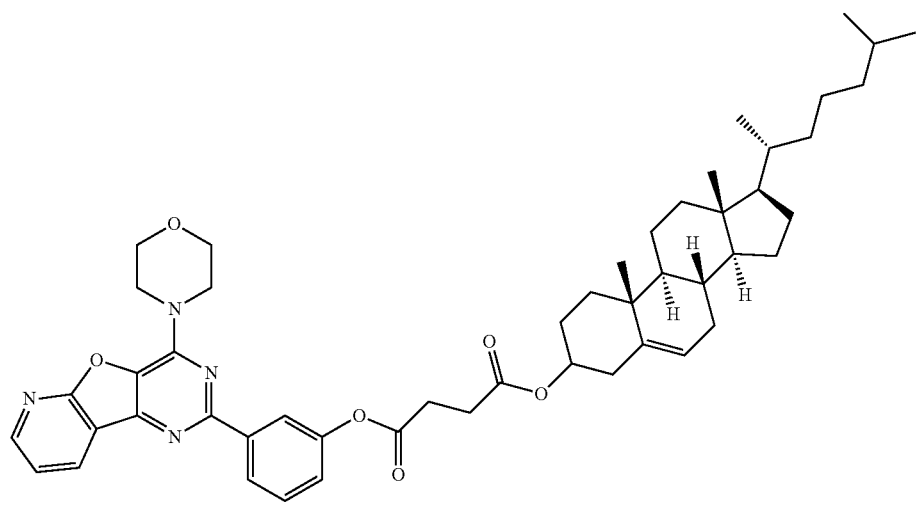

In some embodiments, the chemotherapeutic agent is a taxane. The term "Taxane" is generally referred to diterpene-containing compounds produced by the plants of the genus *Taxus* (e.g., yews, such as, but not limited to, *Taxus baccata, Taxus brevifolia, Taxus canadensis, Taxus chinensis, Taxus cuspidata, Taxus floridana, Taxus globosa, Taxus sumatrana, Taxus walUchiana*), and synthetic and semisynthetic forms thereof. The term denotes a compound containing the core structure.

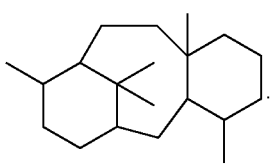 [SMILES: CC1CCCC2(C)CCC3C(C)CCC(CC12)C3(C)C]

The basic taxane core structure may further be substituted or may contain unsaturations in the ring to yield a number of compounds, generically known as taxanes. Generally, such compounds may block cell growth by stopping mitosis by interfering with microtubules. The term "diterpene," as used herein, means chemical compounds having a carbon skeleton derived from four isoprene units. The taxane group of compounds includes paclitaxel and docetaxel.

Taxanes can be isolated from natural sources, and can also be prepared synthetically from naturally occumng precursors. Paclitaxel (TAXOL®, Bnstol-Myers Squibb), for example, can be prepared from baccatin by attachment of protecting groups to the hydroxyl groups of baccatin that are to become the hydroxyl groups of paclitaxel, converting the precursor baccatin to paclitaxel, and then removing the protecting groups from the hydroxyl groups to obtain paclitaxel (see, e.g., WO93/10076. int. pub. date May 27, 1993; K. V. Rao, U.S. Pat. No. 5,200,534; R. A. Holton, U.S. Pat. No. 5,015,744; PCT US92/07990; V. J. Stella and A. E.

Mathew, U.S. Pat. No. 4,960,790; K. C. Nicolau, Nature 3j54 (1993), pp. 464-466; Nicolau, K. C. et al. Nature 367 (1994) pp. 630-634; Holton, R. A., et al. J. Am. Chem. Soc. H6 (1994) pp. 1597-1600; WO93/16059, int. pub. date Aug. 19, 1993; EP 528.729, published Feb. 24, 1993; EP 522,958, published Jan. 13, 1993; WO91/13053, int. pub. date Sep. 5, 1991; EP 414,610, int. pub. date Feb. 27, 1991; the contents of these documents are incorporated herein by reference). Non-limiting examples of taxanes can include paclitaxel and docetaxel, derivatives thereof, and mixtures thereof.

Taxanes can be used effectively to treat a variety of cancers. Paclitaxel, for example, has been found to have activity against ovarian and breast cancers, as well as against malignant melanoma, colon cancer, leukemias and lung cancer (see, e.g., Borman, Chemical & Engineering News, Sep. 2, 1991, pp. 11-18; The Pharmacological Basis of Therapeutics (Goodman Gilman et al., eds.), Pergamon Press, New York (1990), p. 1239; Suffness, Antrtumor Alkaloids, in: "The Alkaloids, Vol. XXV," Academic Press, Inc. (1985), Chapter 1, pp. 6-18; Rizzo et al., J. Pharm. & Biomed. Anal. § (2):159-164 (1990); and Biotechnology 9:933-938 (October. 1991). Paclitaxel acts against cancer cells by binding to tubulin in the cells nuclei, thereby blocking the disassembly of microtubules and consequently, inhibiting cell division (Schiff et al., Nature 277:665 (1979). In one embodiment, the taxane is paclitaxel.

In some embodiments, the conjugate comprises a taxane covalently linked with cholesterol. In some embodiments, the conjugate is of formula III:

In some embodiments, the chemotherapeutic agent is a platinate. Any platinum compound can be used in the methods and compositions described herein. In some embodiments, the platinum compound is a platinum (II) or platinum (IV) compound. The platinum can be dissociably linked to the lipid via at least one coordination bond. In some embodiments, the coordination bond is Pt→O. In some other embodiments, the coordination bond is Pt→N.

In some embodiments, the platinum (II) compound is selected from the group consisting of cisplatin, oxaliplatin, carboplatin, paraplatin, sartraplatin, and combinations thereof. In a preferred embodiment, the platinate is cisplatin or oxalipaltin. Cisplatin [cis-dichlorodiammineplatinum(II)] (CDDP) has emerged as an important class of antitumor agents, and is widely used for the treatment of many malignancies including testicular, ovarian, cervical, head and neck, and non-small cell lung cancer (Jamieson, et al, Chem. Rev. (1999), 99(9): 2467-2498). It was also shown to be active in triple negative breast cancer (Leong, et al., J. Clin. Invest. (2007), 117(5): 1370-80). Its use is however dose-limited mainly because of nephrotoxicity or toxicity to the kidney (Madias, N E and Harrington, J T, Am. J. (1978), 65(2): 307-14).

In some embodiments, the conjugate comprises a platinum dissociably linked with a cholesterol via at least one coordination bond. In some embodiments, the conjugate is of formula IV:

FORMULA III

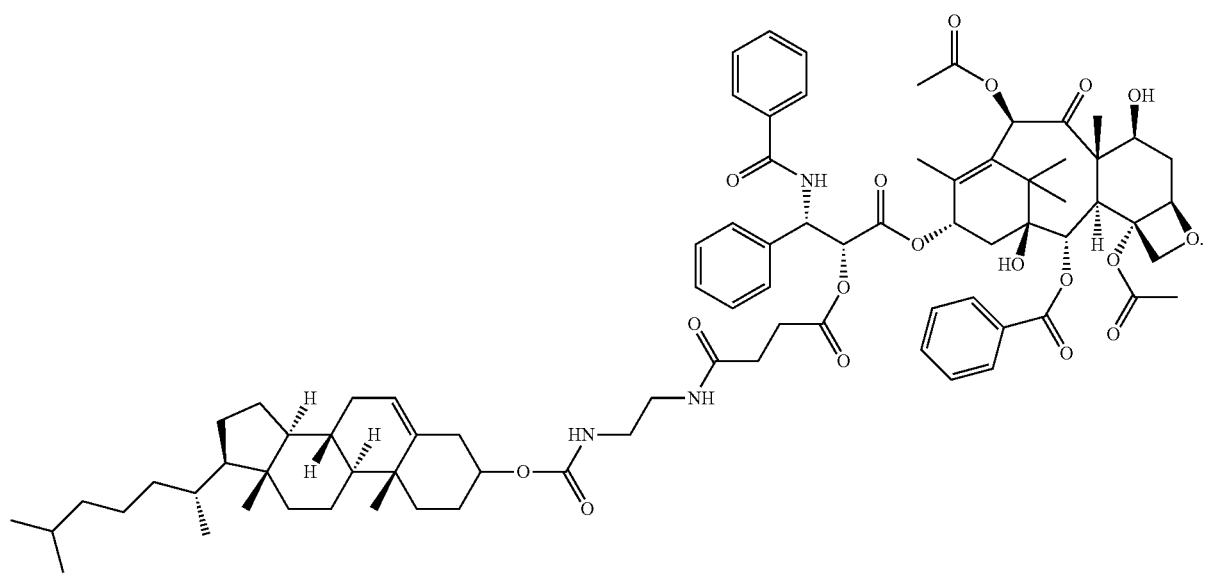

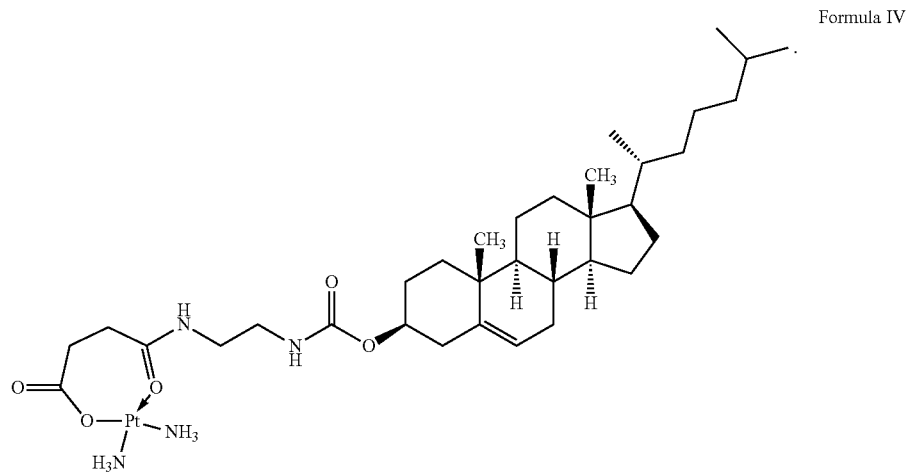

Formula IV

Additional conjugates comprising a platinate (or platinum-containing chemotherapeutic agent) are described in e.g., US Patent Publication 2012/0189571, and International Patent Publication WO 2010/091192; each of which is incorporated by reference herein in its entirety.

The chemotherapeutic agent and the lipid (e.g., cholesterol) can be linked together by a bond or via a linker. This linker can be cleavable or non-cleavable, depending on the application. In certain embodiments, a cleavable linker can be used to release the chemotherapeutic agent after transport to the desired target. The intended nature of the conjugation or coupling interaction, or the desired biological effect, will determine the choice of linker group.

The term "linker" means an organic moiety that connects two parts of a compound. Linkers typically comprise a direct bond or an atom such as oxygen or sulfur, a unit such as $NR^1$, $C(O)$, $C(O)O$, $C(O)NR^1$, $SO$, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, $N(R^1)_2$, C(O), cleavable linking group, substituted or unsubstituted aryl, substituted or unsubstituted heteroaryl, substituted or unsubstituted heterocyclic; where $R^1$ is hydrogen, acyl, aliphatic or substituted aliphatic.

In certain embodiments, the linker is a branched linker. The branch-point of the branched linker can be at least trivalent, but can be a tetravalent, pentavalent or hexavalent atom, or a group presenting such multiple valencies. In certain embodiments, the branch-point can be, —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branch-point can be glycerol or a glycerol derivative.

In some embodiments, the linker comprises at least one cleavable linking group. A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood or serum of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the cell (or under in vitro conditions selected to mimic intracellular conditions) as compared to blood or serum (or under in vitro conditions selected to mimic extracellular conditions). In some embodiments, the cleavable linking group is cleaved by less than 90%, 80%, 70%, 60%, 50%, 40%, 30%, 20%, 10%, 5%, or 1% in the blood (or in vitro conditions selected to mimic extracellular conditions) as compared to in the cell (or under in vitro conditions selected to mimic intracellular conditions).

Exemplary cleavable linking groups include, but are not limited to, redox cleavable linking groups (e.g., —S—S— and —C(R)$_2$—S—S—, wherein R is H or C$_1$-C$_6$ alkyl and at least one R is C$_1$-C$_6$ alkyl such as CH$_3$ or CH$_2$CH$_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched C$_1$-C$_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, the linker comprises an acid labile group. Generally, an acid cleavable linking group is cleaveable in an acidic environment with a pH of about 6.5 or lower (e.g., about 6.5, 6.0, 5.5, 5.0, 4.5, 4.0, 3.5, 3.0, or lower), or by agents such as enzymes that can act as a general acid.

In some embodiments, the linker is C(O), C(O)CH$_2$CH$_2$C(O), or C(O)NH(CH$_2$)$_2$NHC(O)(CH$_2$)$_2$C(O).

Generally, the composition can comprise any amount of the conjugate. For example, the composition can comprise from about 1% to about 99% (w/w) of the conjugate. In some embodiments, the composition can comprise two or more different conjugates disclosed herein. Further, the different conjugates can be present in any desired ratio. For example, the different conjugates can be in a ratio ranging from about 100:1 to 1:100.

In addition to the conjugate, the composition (e.g., a particle comprising the conjugate) can further include one or more additional lipids and/or other components such as cholesterol. Without wishing to be bound by a theory, other lipids can be included in the compositions for a variety of purposes, such as to prevent lipid oxidation, to stabilize bilayer, to reduce aggregation during formation or to attach ligands onto the particle surface. Any of a number of lipids can be present, including but not limited to, amphipathic, neutral, cationic, anionic lipids, sterols, and phospholipids. Further, such lipids can be used alone or in any combination with each other. In some embodiments, the composition further comprises a lipoprotein particle, e.g., HDL or LDL. The composition can comprise from about 1% to about 99% (w/w) of the additional lipid or component. Further the additional lipid or component can be present in 10:1 to 1:10 ratio with the conjugate. If two or more different additional lipids are present in the composition, each lipid can be independently in 10:1 to 1:10 ratio with the conjugate. Further, if two or more different additional lipids are present in the composition, the two lipids can be in 10:1 to 1:10 ratio. Without limitations, two different components (conjugate and lipid or two different lipids) of the composition can be in ratio 10:1 to 1:10, 5:1 to 1:5, or 2.5:1 to 1:2.5. In some embodiments, two different components in the composition can be in ratio of about 1:1, about 1:1.2, about 1:1.5, about 1:1.7, about 1:2, about 1:2.5, about 1:3, about 1:3.5, about 1:4, about 1:4.5, about 1:5, about 1:5.5, about 1:6, about 1:6.5, about 1:7, about 1:7.5, about 1:8, about 1:8.5, about 1:9, about 1:9.5, or about 1:10. If the composition comprises more than two components ratio between any two components can be independent of ratio between any other two components.

Additional components that can be present in the particle composition can include bilayer stabilizing components such as polyamide oligomers (see, e.g., U.S. Pat. No. 6,320,017), peptides, proteins, detergents, lipid-derivatives, such as PEG conjugated to phosphatidylethanolamine, PEG conjugated to phosphatidic acid, PEG conjugated to ceramides (see, U.S. Pat. No. 5,885,613), PEG conjugated dialkylamines, PEG conjugated 1,2-diacyloxypropan-3-amines, and PEG conjugated to 1,2-distearoyl-sn-glycem-3-phosphoethanolamine (DSPE). In some embodiments, the bilayer stabilizing component is DSPE-PEG2000.

The composition can also include components selected to reduce aggregation of particles during formation, which can result from steric stabilization of particles which prevents charge-induced aggregation during formation. Suitable components that reduce aggregation include, but are not limited to, polyethylene glycol (PEG)-modified lipids (i.e., PEG conjugated lipids), monosialoganglioside Gm1, and polyamide oligomers ("PAO") such as (described in U.S. Pat. No. 6,320,017). Exemplary suitable PEG-modified lipids include, but are not limited to, PEG-modified diacylglycerols and dialkylglycerols, PEG-modified phosphatidylethanolamine and phosphatidic acid, PEG-ceramide conjugates (e.g., PEG-CerC14 or PEG-CerC20), PEG-modified dialkylamines, PEG-modified 1,2-diacyloxypropan-3-amines, and PEG conjugated DSPE (e.g., DSPE-PEG2000). Other compounds with uncharged, hydrophilic, steric-barrier moieties, which prevent aggregation during formation, like PEG, Gm1, or ATTA, can also be coupled to lipids to reduce aggregation during formation. ATTA-lipids are described, e.g., in U.S. Pat. No. 6,320,017, and PEG-lipid conjugates are described, e.g., in U.S. Pat. Nos. 5,820,873, 5,534,499 and 5,885,613. Typically, the concentration of the lipid component selected to reduce aggregation is about 0.1 to 15% (by mole percent of lipids). It should be noted that aggregation preventing compounds do not necessarily require lipid conjugation to function properly. Free PEG or free ATTA in solution can be sufficient to prevent aggregation. If the liposomes are stable after formulation, the PEG or ATTA can be dialyzed away before administration to a subject.

Neutral lipids, when present in the composition, can be any of a number of lipid species which exist either in an uncharged or neutral zwitterionic form at physiological pH. Such lipids include, but are not limited to, diacylphosphatidylcholine, diacylphosphatidylethanolamine, ceramide, sphingomyelin, dihydrosphingomyelin, cephalin, and cerebrosides. The selection of neutral lipids for use in liposomes described herein is generally guided by consideration of, e.g., liposome size and stability of the liposomes in the bloodstream. Preferably, the neutral lipid component is a lipid having two acyl groups, (i.e., diacylphosphatidylcholine and diacylphosphatidylethanolamine). Lipids having a variety of acyl chain groups of varying chain length and degree of saturation are available or can be isolated or synthesized by well-known techniques. In one group of embodiments, lipids containing saturated or unsaturated fatty acids with carbon chain lengths in the range of $C_6$ to $C_{22}$ (e.g., $C_6$, $C_8$, $C_{10}$, $C_{12}$, $C_{14}$, $C_{16}$, $C_{18}$, $C_{22}$, or $C_{22}$) are preferred. Additionally, lipids having mixtures of saturated and unsaturated fatty acid chains can be used. In some embodiments, the neutral lipids can be phosphatidylcholine, DOPE, DSPC, POPC, DMPC, DPPC or any related phosphatidylcholine. The neutral lipids useful in the present invention can also be composed of sphingomyelin, dihydrosphingomyeline, or phospholipids with other head groups, such as serine and inositol.

When present in the composition, the sterol component can be any of those sterols conventionally used in the field of liposome, lipid vesicle or lipid particle preparation. A preferred sterol is cholesterol.

When present in the composition, the cationic lipids can be any of a number of lipid species which carry a net positive charge at about physiological pH. Such lipids include, but are not limited to, N,N-dioleyl-N,N-dimethylammonium chloride ("DODAC"); N-(2,3-dioleyloxy)propyl-N,N—N-triethylammonium chloride ("DOTMA"); N,N-distearyl-N,N-dimethylammonium bromide ("DDAB"); N-(2,3-dioleoyloxy)propyl)-N,N,N-trimethylammonium chloride ("DOTAP"); 1,2-Dioleyloxy-3-trimethylaminopropane chloride salt ("DOTAP.Cl"); 3β-(N—(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleyloxy)propylamine ("DODMA"), N-(1,2-dimyristyloxyprop-3-yl)-N,N-dimethyl-N-hydroxyethyl ammonium bromide ("DMRIE"), 5-carboxyspermylglycine diocaoleyamide ("DOGS"), and dipalmitoylphosphatidylethanolamine 5-carboxyspermyl-amide ("DPPES"). Additionally, a number of commercial preparations of cationic lipids can be used, such as, e.g., LIPOFECTIN (including DOTMA and DOPE, available from GIBCO/BRL), and LIPOFECTAMINE (comprising DOSPA and DOPE, available from GIBCO/BRL). Other cationic lipids suitable for lipid particle formation are described in WO98/39359, WO96/37194. Other suitable cationic lipids are described, for example in US Patent Application Publication No. 2011/0997720 and PCT Patent Application Publication No. WO 2009/132131 and No. WO 2009/132131, content of all of which is incorporated herein by reference in its entirety.

When present in the composition, the anionic lipid can be any of a number of lipid species which carry a net negative charge at about physiological pH. Such lipids include, but are not limited to, phosphatidylglycerol, cardiolipin, diacylphosphatidylserine, diacylphosphatidic acid, N-dodecanoyl phosphatidyletholoamine, N-succinyl phosphatidylethanolamine, N-glutaryl phosphatidylethanolamine, lysylphosphatidylglycerol, and other anionic modifying groups joined to neutral lipids.

As used herein, the term "amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids.

In some embodiments, the composition further comprises a phospholipid. Without limitations, the phospholipids can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl cholines with defined acyl groups having 6 to 22 carbon atoms, phosphatidyl ethanolamines, phosphatidyl inositols, phosphatidic acids, phosphatidyl serines, sphingomyelin or phosphatidyl glycerols. Suitable phospholipids include, but are not limited to, phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoyl-phosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and the like. Non-phosphorus containing lipids can also be used. These include, e.g., stearylamine, docecylamine, acetyl palmitate, fatty acid amides, and the like. Other phosphorus-lacking compounds, such as sphingolipids, glycosphingolipid families, diacylglycerols, and β-acyloxyacids, can also be used Also suitable for inclusion in the compositions described herein are programmable fusion lipids. Particles containing programmable fusion lipids have little tendency to fuse with cell membranes and deliver their payload until a given signal event occurs. This allows the composition to distribute more evenly after administration into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the particle membrane over time. By the time the particle is suitably distributed in the body, it has lost sufficient cloaking agent so as to be fusogenic. With other signal events, it is desirable to choose a signal that is associated with the disease site or target cell, such as lower pH at a site of tumor.

One or more complementary surface active agent can be added to the compositions, for example as complements to the characteristics of an amphiphilic agent or to improve particle stabilizing capacity or enable an improved solubilization. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of PLURONIC®, POLOXAMER®, SPAN®, TWEEN®, POLYSORBATE®, TYLOXAPOL®, EMULPHOR® or CREMOPHOR® and the like. The complementary surface active agents can also be of an ionic nature, such as bile duct agents, cholic acid or deoxycholic their salts and derivatives or free fatty acids, such as oleic acid, linoleic acid and others. Other ionic surface active agents are found among cationic lipids like $C_6$-$C_{24}$ alkylamines or alkanolamine and cationic cholesterol esters.

In some embodiments, the composition comprises a PEG conjugated lipid and a phospholipid.

The composition can also include a targeting moiety, e.g., a targeting moiety that is specific to a cell type or tissue. The targeting moiety is also referred to as a targeting ligand or targeting agent herein. Targeting of particles with a surface coating of hydrophilic polymer chains, such as polyethylene glycol (PEG) chains, for targeting has been proposed (Allen, et al., *Biochimica et Biophysica Acta* 1237: 99-108 (1995); DeFrees, et al., *Journal of the American Chemistry Society* 118: 6101-6104 (1996); Blume, et al., *Biochimica et Biophysica Acta* 1149: 180-184 (1993); Klibanov, et al., *Journal of Liposome Research* 2: 321-334 (1992); U.S. Pat. No. 5,013,556; Zalipsky, *Bioconjugate Chemistry* 4: 296-299 (1993); Zalipsky, *FEBS Letters* 353: 71-74 (1994); Zalipsky, in Stealth Liposomes Chapter 9 (Lasic and Martin, Eds) CRC Press, Boca Raton Fla. (1995). Other targeting moieties, such as ligands, cell surface receptors, glycoproteins, vitamins (e.g., riboflavin), aptamers and monoclonal antibodies, can also be used. The targeting moieties can include the entire protein or fragments thereof. Targeting mechanisms generally require that the targeting agents be positioned on the surface of the liposome in such a manner that the targeting moiety is available for interaction with the target, for example, a cell surface receptor.

In one approach, a targeting moiety, such as receptor binding ligand, can be linked to a component (e.g., a lipid) of the composition. In some embodiments, the ligand can be conjugated with PEG. A variety of different targeting agents and methods are known and available in the art, including those described, e.g., in Sapra, P. and Allen, T M, *Prog. Lipid Res.* 42(5):439-62 (2003); and Abra, R M et al., *J. Liposome Res.* 12:1-3, (2002). Other lipids conjugated with targeting moieties are described in US Patent Application Publication No. US2009/0247608 and No. US2012/0046478, content of both of which is incorporated herein by reference in its entirety.

Without limitation, a ligand can be selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof.

In some embodiments, the targeting ligand can be selected from the group consisting of polylysine (PLL), poly L-aspartic acid, poly L-glutamic acid, styrene-maleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacrylic acid), N-isopropylacrylamide polymers, polyphosphazine, polyethylenimine, cspermine, spermidine, polyamine, pseudopeptide-polyamine, peptidomimetic polyamine, dendrimer polyamine, arginine, amidine, protamine, thyrotropin, melanotropin, lectin, surfactant protein A, mucin, transferrin, bisphosphonate, polyglutamate, polyaspartate, an aptamer, asialofetuin, hyaluronan, procollagen, insulin, transferrin, albumin, acridines, cross-psoralen, mitomycin C, TPPC4, texaphyrin, Sapphyrin, polycyclic aromatic hydrocarbons (e.g., phenazine, dihydrophenazine), bile acids, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine), RGD peptide, radiolabeled markers, haptens, naproxen, aspirin, dinitrophenyl, HRP, AP, lectins, vitamin A, vitamin E, vitamin K, vitamin B, folic acid, B12, riboflavin, biotin, pyridoxal, taxon, vincristine, vinblastine, cytochalasin, nocodazole, japlakinolide, latrunculin A, phalloidin, swinholide A, indanocine, myoservin, tumor necrosis factor alpha (TNFalpha), interleukin-1 beta, gamma interferon, GalNAc, galactose, mannose, mannose-6P, clusters of sugars such as GalNAc cluster, mannose cluster, galactose cluster, an aptamer, integrin receptor ligands, chemokine receptor ligands, serotonin receptor ligands, PSMA, endothelin, GCPII, somatostatin, cellular adhesion molecules (CAMS), and any combinations thereof.

A targeting agent can bind to and/or penetrate a specific cell type(s) at a greater rate than to other cell types, e.g. cancer cells as compared to healthy cells. A targeting agent can be selected from the group consisting of peptides, polypeptides, proteins, peptidomimetics, glycoproteins, lectins, nucleosides, nucleotides, nucleic acids, monosaccharides, disaccharides, trisaccharides, oligosaccharides, polysaccharides, lipopolysaccharides, vitamins, steroids, hormones, cofactors, receptors, receptor ligands, antibodies, antigen binding fragments of antibodies, and analogs and derivatives thereof. Targeting agents that preferentially bind to and/or cross the membrane of cancer cells are known in the art, e.g. iRGD, RGD, Lyp-1 peptide (CGNKRTRGC; SEQ ID NO:3), NGR peptide, iNGR, RGR peptide, CAR peptide, tCAR peptide (CARSKNK; SEQ ID NO: 2); FSH-33, Allatostatin 1, the pentapeptide CREKA (SEQ ID NO: 4), Hepatocarcinoma targeting peptide, Peptide GFE, anti-EGFR antibodies and/or antibody fragments, in particular Cetuximab, CendR, iRGD peptide (RGD-CendR hybrid peptide), small molecules, antibodies and/or antibody fragments binding to cancer-specific epitopes like e.g. CEA, Gastrin-releasing peptide receptors, Somatostatin receptors, Galanin receptors, Follicle-stimulating hormone receptors, p32 protein, Fibroblast growth factor receptors, HepG2, Epidermal growth factor receptors, Integrin αvβ6, Neuropilin-1 receptor and VEGF receptors and variants or combinations thereof. In some embodiments, a targeting agent can be iRGD, e.g. a peptide having the sequence CRGDKGPDC (SEQ ID NO: 1).

A targeting agent can be present, e.g. on the surface of a nanoparticle described herein and/or partially embedded in the membrane or lipid layer of a nanoparticle described herein. Methods of incorporating a targeting agent are known in the art and non-limiting examples are described elsewhere herein. In some embodiments, a composition described herein can comprise a two or more targeting agents, e.g. a composition can comprise a combination of nanoparticles, each comprising a different targeting agent and/or a composition can comprise nanoparticles which each comprise multiple targeting agents. In some embodiments, a composition described herein can comprise one targeting agent, two targeting agents, three targeting agents, or more targeting agents.

The composition comprising the conjugate can be in the form of a particle. Generally, the particle can be of any shape or form, e.g., spherical, rod, elliptical, cylindrical, capsule, or disc; and these particles can be part of a network or an aggregate. In some embodiments, the particle is a microparticle or a nanoparticle. As used herein, the term "microparticle" refers to a particle having a particle size of about 1 μm to about 1000 μm. As used herein, the term "nanoparticle" refers to particle having a particle size of about 0.1 nm to about 1000 nm. As used herein, the term "particle" encompasses liposomes, emulsions, vesicles and lipid particles. Without limitations, the particle can have any size from nm to millimeters.

Generally, the particles disclosed herein are nanoparticles and have an average diameter of from about 5 nm to about 500 nm. In some embodiments, the particles have an average diameter of from about 75 nm to about 500 nm, from about 25 nm to about 250 nm, from about 50 nm to about 150 nm, from about 75 nm to about 125 nm, from about 50 nm to about 500 nm, from about 75 nm to about 200 nm, from about 100 to about 175 nm, from about 125 nm to about 175 nm, from about 40 nm to about 90 nm, or from about 50 nm to about 80 nm.

In some embodiments a nanoparticle can be less than about 1 um in diameter, e.g., about 1 um or less in diameter, about 500 nm or less in diameter, about 400 nm or less in diameter, about 300 nm or less in diameter, about 200 nm or less in diameter, about 100 nm or less in diameter, about 50 nm or less in diameter, or about 10 nm or less in diameter. In some embodiments a nanoparticle can be less than 1 um in diameter, e.g., 1 um or less in diameter, 500 nm or less in diameter, 400 nm or less in diameter, 300 nm or less in diameter, 200 nm or less in diameter, 100 nm or less in diameter, 50 nm or less in diameter, or 10 nm or less in diameter. In some embodiments, the nanoparticles in a composition can be from about 1 nm to about 1 um in diameter, e.g. from about 1 nm to about 500 nm in diameter, from about 1 nm to about 200 nm in diameter, from about 10 nm to about 200 nm in diameter, from about 100 nm to about 200 nm in diameter, or from about 10 nm to about 100 nm in diameter. In some embodiments, the nanoparticles in a composition can be from 1 nm to 1 um in diameter, e.g. from 1 nm to 500 nm in diameter, from 1 nm to 200 nm in diameter, from 10 nm to 200 nm in diameter, from 100 nm to 200 nm in diameter, or from 10 nm to 100 nm in diameter.

In some embodiments, nanoparticles can be selected to be of specific sizes, e.g. less than about 200 nm in diameter. Methods of selecting nanoparticles of a particular size and/or range of sizes are known in the art and can include, by way of non-limiting example, filtration, sedimentation, centrifugation, and/or chromatographic methods, e.g. SEC.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

The particles can be, e.g., monodisperse or polydisperse and the variation in diameter of the particles of a given dispersion can vary. In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

In some embodiments, the composition is in the form of a liposome. As used herein, the term "liposome" encompasses any compartment enclosed by a lipid layer. Liposomes can have one or more lipid membranes. Liposomes can be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1 µm. Liposomes with several non-concentric membranes, i.e., several smaller vesicles contained within a larger vesicle, are termed multivesicular vesicles.

In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane.

A liposome composition can be prepared by a variety of methods that are known in the art. See e.g., U.S. Pat. Nos. 4,235,871, 4,897,355 and 5,171,678; published PCT applications WO 96/14057 and WO 96/37194; Felgner, P. L. et al., Proc. Natl. Acad. Sci., USA (1987) 8:7413-7417, Bangham, et al. M. Mol. Biol. (1965) 23:238, Olson, et al. Biochim. Biophys. Acta (1979) 557:9, Szoka, et al. Proc. Natl. Acad. Sci. (1978) 75: 4194, Mayhew, et al. Biochim. Biophys. Acta (1984) 775:169, Kim, et al. Biochim. Biophys. Acta (1983) 728:339, and Fukunaga, et al. Endocrinol. (1984) 115:757, content of all of which is incorporated herein by reference in its entirety.

The liposomes can be prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323, content of which is incorporated herein by reference in its entirety.

The compositions described herein can also be in the form of an emulsion. Emulsions are typically heterogenous systems of one liquid dispersed in another in the form of droplets (Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the conjugate disclosed herein can be present as a solution in either the aqueous phase or the oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers can broadly be classified into four categories: synthetic surfactants, naturally occurring emulsifiers, absorption bases, and finely dispersed solids (Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials can also be included in emulsion formulations and contribute to the properties of emulsions. These include, but are not limited to, fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The applications of emulsion formulations via dermatological, oral and parenteral routes and methods for their manufacture have been reviewed in the literature (Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199).

In some embodiments, a composition described herein can comprise two or more conjugates disclosed herein. For example the composition can comprise two or more conjugates selected from conjugate of formula I, II, III, and IV. In some embodiments, the composition can comprise conjugate of formula I and conjugate of formula II, conjugate of formula I and conjugate of formula III, conjugate of formula I and conjugate of formula IV, conjugate of formula II and conjugate of formula III, conjugate of formula II and conjugate of formula IV, or conjugate of formula III and conjugate of formula IV. In some embodiments, the two or more conjugates can be present on the same nanoparticle, e.g. a single nanoparticle can comprise two or more types of conjugates. In some embodiments, a composition can comprise multiple types of nanoparticles, each of which comprises a different conjugate (or different suites of two or more conjugates). In some embodiments, a composition can comprise two or more conjugates as described herein, e.g. two conjugates, three conjugates, four conjugates, or more conjugates. In some embodiments, the two or more conjugates comprise two or more types of chemotherapeutic agents, e.g. a PI3K inhibitor and a platinate; a PI3K inhibitor and a taxane; a platinate and a taxane; and/or a PI3K inhibitor, a taxane, and a platinate.

In some embodiments, the methods described herein relate to treating a subject having or diagnosed as having cancer. Subjects having cancer can be identified by a physician using current methods of diagnosing cancer. Symptoms and/or complications of cancer which characterize these conditions and aid in diagnosis are well known in the art and include but are not limited to, growth of a tumor, impaired function of the organ or tissue harboring cancer cells, etc. Tests that may aid in a diagnosis of, e.g. cancer include, but are not limited to, tissue biopsies and histological examination. A family history of cancer, or exposure to risk factors for cancer (e.g. tobacco products, radiation, etc.) can also aid in determining if a subject is likely to have cancer or in making a diagnosis of cancer.

Cancer can include, but is not limited to, carcinoma, including adenocarcinoma, lymphoma, blastoma, melanoma, sarcoma, leukemia, squamous cell cancer, small-cell lung cancer, non-small cell lung cancer, gastrointestinal cancer, Hodgkin's and non Hodgkin's lymphoma, pancreatic cancer, glioblastoma, basal cell carcinoma, biliary tract cancer, bladder cancer, brain cancer including glioblastomas and medulloblastomas; breast cancer, cervical cancer, choriocarcinoma; colon cancer, colorectal cancer, endometrial carcinoma, endometrial cancer; esophageal cancer, gastric cancer; various types of head and neck cancers, intraepithelial neoplasms including Bowen's disease and Paget's disease; hematological neoplasms including acute lymphocytic and myelogenous leukemia; Kaposi's sarcoma, hairy cell leukemia; chromic myelogenous leukemia, AIDS-associated leukemias and adult T-cell leukemia lymphoma; kidney cancer such as renal cell carcinoma, T-cell acute lymphoblastic leukemia/lymphoma, lymphomas including Hodgkin's disease and lymphocytic lymphomas; liver cancer such as hepatic carcinoma and hepatoma, Merkel cell carcinoma, melanoma, multiple myeloma; neuroblastomas; oral cancer including squamous cell carcinoma; ovarian cancer including those arising from epithelial cells, sarcomas including leiomyosarcoma, rhabdomyosarcoma, liposarcoma, fibROS1arcoma, and osteosarcoma; pancreatic cancer; skin cancer including melanoma, stromal cells, germ cells and mesenchymal cells; pROS1tate cancer, rectal cancer; vulval cancer, renal cancer including adenocarcinoma; testicular cancer including germinal tumors such as seminoma, non-seminoma (teratomas, choriocarcinomas), stromal tumors, and germ cell tumors; thyroid cancer including thyroid adenocarcinoma and medullar carcinoma; esophageal cancer, salivary gland carcinoma, and Wilms' tumors.

In some embodiments, the methods described herein can relate to treating a subject determined to have a cancer with aberrant PI3K signaling. Aberrant PI3K signaling can be increased or decreased signaling relative to a reference level, e.g. the level in the non-cancerous cells of the subject, or the level in a population of healthy subjects. PI3K signaling levels can be determined by examining the level of activity of PI3K directly, or indirectly (e.g. by measuring the level and/or activity of a downstream molecule) as described elsewhere herein. In some embodiments, a cancer with aberrant PI3K signaling can be a cancer with a decreased level of PTEN, increased level and/or activity of PIK3CA, mutations and/or increased levels or activity of tyrosine receptor kinases, AKT, or RAS, and/or increased phosphorylation of PI3K pathway members (e.g. AKT, S6, 4EBP1 and mTOR). In some embodiments, a subject having a cancer with aberrant PI3K signaling can be a subject with decreased glucose tolerance.

The compositions and methods described herein can be administered to a subject having or diagnosed as having cancer. In some embodiments, the methods described herein comprise administering an effective amount of compositions described herein to a subject in order to alleviate a symptom of a cancer. As used herein, "alleviating a symptom of a cancer" is ameliorating any condition or symptom associated with the cancer. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, or intratumoral administration. Administration can be local or systemic.

In some embodiments, a composition described herein (e.g. a composition comprising a PI3K inhibitor) can be administered to a subject in need of a decrease in blood glucose levels. As demonstrated in the Examples herein, the compositions comprising PI3K inhibitors can induce a decrease in blood glucose. Accordingly, described herein are methods of lowering the blood glucose in a subject in need thereof, e.g. improving glucose tolerance. Subject in need of a decrease of blood glucose levels can be subjects with a cancer having aberrant PI3K signaling or subjects otherwise diagnosed as having high blood glucose, e.g. subjects with diabetes or metabolic syndrome.

The term "effective amount" as used herein refers to the amount of a composition described herein needed to alleviate at least one or more symptom of the disease or disorder, and relates to a sufficient amount of pharmacological composition to provide the desired effect. The term "therapeutically effective amount" therefore refers to an amount of a composition described herein that is sufficient to provide a particular anti-tumor effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of a composition described herein, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for tumor size and/or growth, among others. The dosage can be determined by a physician and adjusted, as necessary, to suit observed effects of the treatment.

In some embodiments, the technology described herein relates to a pharmaceutical composition as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a composition as described herein.

In some embodiments, the pharmaceutical composition comprising a composition described herein, e.g. a nanoparticle as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of a composition as described herein are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt can also be incorporated into the parenteral dosage forms of the disclosure, including conventional and controlled-release parenteral dosage forms.

Pharmaceutical compositions a composition as described herein can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a composition as described herein can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the method of treatment disclosed herein comprises co-administering one or more additional anti-cancer therapies to the patient in addition to administering the conjugate or composition comprising the conjugate. Exemplary anti-cancer therapies include, but are not limited to, surgery, chemotherapy, radiation therapy, thermotherapy, immunotherapy, hormone therapy, laser therapy, anti-angiogenic therapy, and any combinations thereof.

In some embodiments, the method comprises co-administering the conjugate and an anti-cancer agent or chemotherapeutic agent to the subject. As used herein, the term "anti-cancer agent" is refers to any compound (including its analogs, derivatives, prodrugs and pharmaceutically salts) or composition which can be used to treat cancer. Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel; germicitibine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; platinate; carmustine; carmustine with Polifeprosan Implant; celecoxib; chlorambucil; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide;

teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and any mixtures thereof. In some embodiments, the anti-cancer agent is a paclitaxel-carbohydrate conjugate, e.g., a paclitaxel-glucose conjugate, as described in U.S. Pat. No. 6,218,367, content of which is herein incorporated by reference in its entirety.

In some embodiments, the anti-cancer agent is a platinate selected from the group consisting of cisplatin, oxaliplatin, carboplatin, paraplatin, sartraplatin, and any combinations thereof.

In addition, the methods of treatment can further include the use of radiation or radiation therapy. Further, the methods of treatment can further include the use of surgical treatments.

In some embodiments, a method of treating cancer described herein can comprise administering a combination of any two of the combinations described herein, e.g. a composition comprising nanoparticles comprising molecules having the structure of Formula I and a composition comprising nanoparticles comprising molecules having the structure of Formula IV. In some embodiments, a method of treating cancer as described herein can comprise administering a combination of a composition described herein and a second agent and/or treatment. In some embodiments, the composition described herein can be a composition comprising a taxane, e.g. a composition of nanoparticles comprising a molecule having the structure of Formula IV and a PI3K inhibitor, e.g. PI103.

In certain embodiments, an effective dose of a composition as described herein can be administered to a patient once. In certain embodiments, an effective dose of a composition as described herein can be administered to a patient repeatedly. For systemic administration, subjects can be administered a therapeutic amount of a composition as described herein, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. tumor size and/or growth by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity a composition as described herein. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition as described herein can be administered over a period of time, such as over a 5 minute, 10 minute, 15 minute, 20 minute, or 25 minute period.

The dosage ranges for the administration of a composition as described herein, according to the methods described herein depend upon, for example, the form of a composition as described herein, its potency, and the extent to which symptoms, markers, or indicators of a condition described herein are desired to be reduced, for example the percentage reduction desired for tumor growth. The dosage should not be so large as to cause adverse side effects. Generally, the dosage will vary with the age, condition, and sex of the patient and can be determined by one of skill in the art. The dosage can also be adjusted by the individual physician in the event of any complication.

The efficacy of a composition as described herein in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. tumor size and/or growth. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. tumor size and/or growth). It is well within the ability of one skilled in the art to monitor efficacy of administration and/or treatment by measuring any one of such parameters, or any combination of parameters. Efficacy can be assessed in animal models of a condition described herein, for example treatment of cancer. When using an experimental animal model, efficacy of treatment is evidenced when a statistically significant change in a marker is observed, e.g. a decreased in tumor size and/or growth.

In vitro and animal model assays are provided herein which allow the assessment of a given dose of a composition as described herein. By way of non-limiting example, the effects of a dose of a composition can be assessed by an in vitro cell viability assay. A non-limiting example of a protocol for such an assay is as follows: cells, e.g. cancer cell lines, are contacted with compositions described herein and viability determined at one or more timepoints using a cell viability reagent, e.g. CellTiter 96 Aqueous One Solution reagents (PROMEGA, WI).

The efficacy of a given dosage can also be assessed in an animal model, e.g. the murine model of ovarian cancer described in the Examples herein. Briefly, ovarian adenocarcinomas can be induced in K-Ras$^{LSL/+}$/Pten$^{fl/fl}$ mice via intrabursal delivery of adenovirus-carrying Cre recombinase. Once mice develop medium to large tumors, they can be administered a composition as described herein, e.g. via tail vein injection. Tumor imaging can be performed and/or mice can be sacrificed.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of cancer. A subject can be male or female.

A subject can be one who has been previously diagnosed with or identified as suffering from or having a condition in need of treatment (e.g. cancer) or one or more complications related to such a condition, and optionally, have already undergone treatment for cancer or the one or more complications related to cancer. Alternatively, a subject can also be one who has not been previously diagnosed as having cancer or one or more complications related to cancer. For example, a subject can be one who exhibits one or more risk factors for cancer or one or more complications related to cancer or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

As used herein, the term "inhibitor" refers to an agent which can decrease the expression and/or activity of the targeted expression product (e.g. mRNA encoding the target or a target polypeptide), e.g. by at least 10% or more, e.g. by 10% or more, 50% or more, 70% or more, 80% or more, 90% or more, 95% or more, or 98% or more. The efficacy of an inhibitor of, for example, PI3K, e.g. its ability to decrease the level and/or activity of PI3K can be determined, e.g. by measuring the level of a PI3K polypeptide (and/or mRNA encoding such a polypeptide) and/or the activity of PI3K. Methods for measuring the level of a given mRNA and/or polypeptide are known to one of skill in the art, e.g. RTPCR with primers can be used to determine the level of RNA and Western blotting with an antibody can be used to determine the level of a polypeptide. The activity of, e.g. PI3K can be determined using methods known in the art and described above herein.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer. The term "treating" includes reducing or alleviating at least one adverse effect or symptom of a condition, disease or disorder associated with a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

As used herein, the term "amphiphilic" refers to a molecule that has both a hydrophobic portion and a lipophobic portion, i.e. at least one a polar, water-soluble group and at least one a nonpolar, water-insoluble group. Typically, in a two phase system having a polar, aqueous phase and a non-polar, non-aqueous phase, an amphiphilic molecule will partition to the interface of the two phases. In simpler non limiting terms, an amphiphile is a molecule that is soluble in both an aqueous environment and a non-aqueous environment. The term "amphiphile" refers to an amphiphilic molecule.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

The term "aromatase inhibitor", as used herein, relates to a compound which inhibits the estrogen production, i.e., the conversion of the substrates androstenedione and testosterone to estrone and estradiol, respectively. The term includes, but is not limited to, steroids, especially atamestane, exemestane and formestane; and, in particular, non-steroids, especially aminoglutethimide, roglethimide, pyridoglutethimide, trilostane, testolactone, ketoconazole, vorozole, fadrozole, anastrozole and letrozole.

The term "anti-estrogen", as used herein, relates to a compound which antagonizes the effect of estrogens at the estrogen receptor level. The term includes, but is not limited to, tamoxifen, fulvestrant, raloxifene and raloxifene hydrochloride.

The term "anti-androgen", as used herein, relates to any substance which is capable of inhibiting the biological effects of androgenic hormones and includes, but is not limited to, bicalutamide.

The term "gonadorelin agonist", as used herein, includes, but is not limited to, abarelix, goserelin and goserelin acetate. Goserelin is disclosed in U.S. Pat. No. 4,100,274 and is marketed as ZOLADEX. Abarelix can be formulated, e.g., as disclosed in U.S. Pat. No. 5,843,901. The term "topoisomerase I inhibitor", as used herein, includes, but is not limited to, topotecan, irinotecan, gimatecan, camptothecin and its analogues, 9-nitrocamptot ecin and the macromolecular camptothecin conjugate PNU-166148 (compound A1 in WO 99/17804).

The term "topoisomerase II inhibitor", as used herein, includes, but is not limited to, the anthracyclines, such as doxorubicin, daunorubicin, epirubicin, idarubicin and nemorubicin; the anthraquinones mitoxantrone and losoxantrone; and the podophillotoxines etoposide and teniposide.

The term "microtubule active agent" relates to microtubule stabilizing, microtubule destabilizing agents and microtublin polymerization inhibitors including, but not limited to, taxanes, e.g., paclitaxel and docetaxel; *vinca* alkaloids, e.g., vinblastine, especially vinblastine sulfate; vincristine, especially vincristine sulfate and vinorelbine; discodermolides; colchicines; and epothilones and derivatives thereof, e.g., epothilone B or D or a derivative thereof. Also included are Epotholine derivatives which are disclosed in U.S. Pat. No. 6,194,181, WO 98/10121, WO 98/25929, WO 98/08849, WO 99/43653, WO 98/22461 and WO 00/31247. Especially preferred are Epotholine A and/or B.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin, BCNU, Gliadel), temozolomide, nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death.

The terms "anti-neoplastic" and "anti-metabolite" agents refers to the group of compounds that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, 5-fluorouracil (5-FU); asparaginase; capecitabine; cladribine (2-CDA); cytarabine; DNA de-methylating agents, such as 5-azacytidine and decitabine; edatrexate; floxuridine (5-FUdR); fludarabine phosphate; folic acid antagonists such as pemetrexed; gemcitabine; hydroxyurea; leucovorin; mercaptopurine (6-MP); methotrexate; pentostatin; and thioguanine (6-TG).

The term "compound targeting/decreasing a protein or lipid kinase activity", as used herein, includes, but is not limited to: protein tyrosine kinase and/or serine and/or threonine kinase inhibitors or lipid kinase inhibitors, e.g., i) compounds targeting, decreasing or inhibiting the activity of the platelet-derived growth factor-receptors (PDGFR), especially compounds which inhibit the PDGF receptor, e.g., a/V-phenyl-2-pyrimidine-amine derivative, e.g., imatinib, SU101, SU6668 and GFB-111; ii) compounds targeting, decreasing or inhibiting the activity of the fibroblast growth factor-receptors (FGFR); iii) compounds targeting, decreasing or inhibiting the activity of the insulin-like growth factor I receptor (IGF-IR), especially compounds which inhibit the IGF-IR, such as those compounds disclosed in WO 02/092599, in particular trans-5-(3-benzyloxy-phenyl)-7-(3-pyrrolidin-1-ylmethyl-cyclobutyl)-7H-pyrrolo[2,3-d]pyrimidin-4-ylamine and cis-7-(3-azetidin-1-ylmethyl-cyclobutyl)-5-(3-benzyloxy-phenyl)-7H-pyrrolo[2,3-d] pyrimidin-4-ylamine or pharmaceutically acceptable salts of these compounds; iv) compounds targeting, decreasing or inhibiting the activity of the Trk receptor tyrosine kinase family; v) compounds targeting, decreasing or inhibiting the activity of the Axl receptor tyrosine kinase family; vi) compounds targeting, decreasing or inhibiting the activity of the RET receptor tyrosine kinase; vii) compounds targeting, decreasing or inhibiting the activity of the c-kit receptor tyrosine kinases, especially compounds which inhibit the c-Kit receptor, e.g., imatinib; viii) compounds targeting, decreasing or inhibiting the activity of members of the c-Abl family and their gene-fusion products, e.g., Bcr-Abl kinase, such as especially compounds which inhibit the activity of c-Abl family members and their gene fusion products, e.g., a/V-phenyl-2-pyrimidine-amine derivative, e.g., imatinib, PD180970, AG957, NSC 680410 or PD173955 from Parke-Davis; ix) compounds targeting, decreasing or inhibiting the activity of members of the protein kinase C (PKC) and Raf family of serine/threonine kinases, members of the MEK, SRC, JAK, FAK, PDK and Ras/MAPK family members, or PI3 kinase (PI3K) family, or of the PI3-kinase-related kinase family, and/or members of the cyclin-dependent kinase family (CDK) and are especially those staurosporine derivatives disclosed in U.S. Pat. No. 5,093,330, e.g., midostaurin;

examples of further compounds include, e.g., UCN-01; safingol; BAY 43-9006; Bryostatin 1; Perifosine; llmofosine; RO 318220 and RO 320432; GO 6976; Isis 3521; LY333531/LY379196; isochinoline compounds, such as those disclosed in WO 00/09495; FTIs; PD184352 or QAN697 (a PI3K inhibitor); x) compounds targeting, decreasing or inhibiting the activity of protein tyrosine kinase inhibitors include imatinib mesylate (GLEEVEC/ GLIVEC) or a tyrphostin. A tyrphostin is preferably a low molecular weight ($M_r$<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556 and AG957 and adaphostin (4-{[(2,5-dihydroxyphenyl)methyl]amino}-benzoic acid adamantyl ester, NSC 680410); and xi) compounds targeting, decreasing or inhibiting the activity of the epidermal growth factor family of receptor tyrosine kinases (EGFR, ErbB2, ErbB3, ErbB4 as homo- or heterodimers), such as compounds which target, decrease or inhibit the activity of the epidermal growth factor receptor family are especially compounds, proteins or antibodies which inhibit members of the EGF receptor tyrosine kinase family, e.g., EGF receptor, ErbB2, ErbB3 and ErbB4 or bind to EGF or EGF-related ligands, and are in particular those compounds, proteins or antibodies generically and specifically disclosed in WO 97/02266, e.g., the compound of Example 39, or in EP 0 564409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347, e.g., compound known as CP 358774, WO 96/33980, e.g., compound ZD 1839; and WO 95/03283, e.g., compound ZM105180, e.g., trastuzumab (Herceptin®), cetuximab, gefitinib (Iressa), erlotinib (Tarceva™), CI-1033, EKB-569, GW-2016, E1.1, E2.4, E2.5, E6.2, E6.4, E2.11, E6.3 or E7.6.3, and 7H-pyrrolo-[2,3-pyrimidine derivatives which are disclosed in WO 03/013541.

Further anti-angiogenic compounds include compounds having another mechanism for their activity, e.g., unrelated to protein or lipid kinase inhibition, e.g., thalidomide (THALOMID) and TNP-470.

The term "cyclooxygenase inhibitor" as used herein includes, but is not limited to, e.g., Cox-2 inhibitors, 5-alkyl substituted 2-arylaminophenylacetic acid and derivatives, such as celecoxib (CELEBREX), rofecoxib (VIOXX), etoricoxib, valdecoxib (BEXTRA) or a 5-alkyl-2-arylaminophenylacetic acid, e.g., 5-methyl-2-(2'-chloro-6'-fluoroanilino) phenyl acetic acid (lumiracoxib, PREXIGE).

The term "bisphosphonate", as used herein, includes, but is not limited to, etridonic, clodronic, tiludronic, pamidronic, alendronic, ibandronic, risedronic and zoledronic acid.

The term "heparanase inhibitor", as used herein, refers to compounds which target, decrease or inhibit heparin sulphate degradation. The term includes, but is not limited to, PI-88.

The term "telomerase inhibitor", as used herein, refers to compounds which target, decrease or inhibit the activity of telomerase. Compounds which target, decrease or inhibit the activity of telomerase are especially compounds which inhibit the telomerase receptor, e.g., telomestatin.

The term "methionine aminopeptidase inhibitor", as used herein, refers to compounds which target, decrease or inhibit the activity of methionine aminopeptidase. Compounds which target, decrease or inhibit the activity of methionine aminopeptidase are, e.g., bengamide or a derivative thereof.

The term "proteasome inhibitor", as used herein, refers to compounds which target, decrease or inhibit the activity of the proteasome. Compounds which target, decrease or inhibit the activity of the proteasome include, e.g., PS-341 and MLN 341.

The term "matrix metalloproteinase inhibitor" or "MMP inhibitor", as used herein, includes, but is not limited to, collagen peptidomimetic and non-peptidomimetic inhibitors; tetracycline derivatives, e.g., hydroxamate peptidomimetic inhibitor batimastat; and its orally-bioavailable analogue marimastat (BB-2516), prinomastat (AG3340), metastat (NSC 683551) BMS-279251, BAY 12-9566, TAA211, MMI270B or AAJ996.

The term "agents used in the treatment of hematologic malignancies", as used herein, includes, but is not limited to, FMS-like tyrosine kinase inhibitors, e.g., compounds targeting, decreasing or inhibiting the activity of Flt-3; interferons; cytosine arabinoside (Ara-C); bisulfan; and ALK inhibitors, i.e. compounds which target, decrease or especially inhibit anaplastic lymphoma kinase (ALK).

The term "FMS-like tyrosine kinase inhibitors", as used herein, includes, but is not limited to, compounds which target, decrease or inhibit the activity of FMS-like tyrosine kinase receptors such as especially compounds, proteins or antibodies which inhibit Flt-3, e.g., PKC412, midostaurin, a staurosporine derivative, SU 11248 and MLN518.

The term "HSP90 inhibitors", as used herein, includes, but is not limited to, compounds targeting, decreasing or inhibiting the intrinsic ATPase activity of HSP90; degrading, targeting, decreasing or inhibiting the HSP90 client proteins via the ubiquitin proteasome pathway. Compounds targeting, decreasing or inhibiting the intrinsic ATPase activity of HSP90 are especially compounds, proteins or antibodies which inhibit the ATPase activity of HSP90, e.g., 17-allylamino,17-demethoxygeldanamycin (17-AAG), a geldanamycin derivative; other geldanamycin-related compounds; radicicol and HDAC inhibitors.

The term "histone deacetylase inhibitors" or "HDAC inhibitors" relates to compounds which target, decrease or especially inhibit the activity of histone deacetylase (HDAC), such as sodium butyrate and suberoylanilide hydroxamic acid (SAHA). Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-7H-indol-3-yl)-ethyl]-amino]methyl]phenyl]-2E-2-propenamide, or a pharmaceutically acceptable salt thereof and/ V-hydroxy-3-[4-[(2-hydroxyethyl) {2-(7H-indol-3-yl) ethyl]-amino]methyl]phenyl]-2E-2-propenamide, or a pharmaceutically acceptable salt thereof, especially the lactate salt.

The term "mTOR inhibitors" relates to compounds which target, decrease or inhibit the activity/function of the serine/ threonine mTOR kinase family and are especially compounds, proteins or antibodies which inhibit members of the mTOR kinase family, e.g., CCI-779, ABT578, SAR543, rapamycin and derivatives/analogs thereof, AP23573 and AP23841 from Ariad, everolimus (CERTICAN, RAD001) and sirolimus (RAPAMUNE).

"Somatostatin receptor antagonists", as used herein, refers to agents which target, treat or inhibit the somatostatin receptor, such as octreotide and SOM230. The term "integrin antagonists", as used herein, includes, but is not limited to, e.g. αvβ3 antagonists and αvβ5 antagonists.

"Tumor cell damaging approaches" refers to approaches, such as ionizing radiation. The term "ionizing radiation", referred to above and hereinafter, means ionizing radiation that occurs as either electromagnetic rays, such as X-rays and gamma rays; or particles, such as alpha and beta particles. Ionizing radiation is provided in, but not limited to, radiation therapy and is known in the art. See Hellman, Cancer, 4$^{th}$ Edition, Vol. 1, Devita et al., Eds., pp. 248-275 (1993).

The term "anti-leukemic compounds" includes, e.g., Ara-C, a pyrimidine analog, which is the 2'-α-hydroxy ribose (arabinoside) derivative of deoxycytidine. Also included is the purine analog of hypoxanthine, 6-mercaptopurine (6-MP) and fludarabine phosphate.

The term "EDG binders" as used herein refers to a class of immunosuppressants that modulates lymphocyte recirculation, such as FTY720.

The term "ribonucleotide reductase inhibitors" refers to pyrimidine or purine nucleoside analogs including, but not limited to, fludarabine and/or Ara-C; 6-thioguanine; 5-FU; cladribine; 6-mercaptopurine, especially in combination with Ara-C against ALL; and/or pentostatin. Ribonucleotide reductase inhibitors are especially hydroxyurea or 2-hydroxy-7H-isoindole-1,3-dione derivatives, such as PL-1, PL-2, PL-3, PL-4, PL-5, PL-6, PL-7 or PL-8. See Nandy et al., Ada Oncologica, Vol. 33, No. 8, pp. 953-961 (1994).

The term "S-adenosylmethionine decarboxylase inhibitors", as used herein, includes, but is not limited to, the compounds disclosed in U.S. Pat. No. 5,461,076.

ACE inhibitors include benazepril (CIBACEN), enazepril (LOTENSIN), captopril, enalapril, fosinopril, lisinopril, moexipril, quinapril, ramipril, perindopril and trandolapril.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A conjugate comprising a chemotherapeutic agent conjugated to cholesterol.
2. The conjugate of paragraph 1, wherein the conjugate is an amphiphile.
3. The conjugate of any of paragraphs 1-2, wherein the agent is conjugated to cholesterol via a linker.
4. The conjugate of paragraph 3, wherein the linker is selected from the group consisting of: —O—, —S—, —S—S—, —NR$^1$, —C(O)—, —C(O)O—, —C(O)NR$^1$, —SO—, —SO$_2$—, —SO$_2$NR$^1$—, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl; wherein one or more methylenes can be interrupted or terminated by O, S, S(O), $SO_2$, $N(R^1)_2$, C(O), C(O)O, $C(O)NR^1$, cleavable linking group, substituted or unsubstituted aryl, substituted or unsubstituted heteroaryl, substituted or unsubstituted heterocyclic, and wherein $R^1$ is hydrogen, acyl, aliphatic or substituted aliphatic.

5. The conjugate of paragraph 4, wherein the linker is C(O), $C(O)CH_2CH_2C(O)$, or $C(O)NH(CH_2)_2NHC(O)(CH_2)_2C(O)$.

6. The conjugate of any of paragraphs 1-5, wherein the chemotherapeutic agent is a PI3K inhibitor.

7. The conjugate of paragraph 6, wherein the PI3K inhibitor is selected from the group consisting of:
PI103; PI828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136.

8. The conjugate of paragraph 7, wherein the PI3K inhibitor is selected from the group consisting of:
PI103 and PI828.

9. The conjugate of any of paragraphs 6-8, having the structure of Formula I:

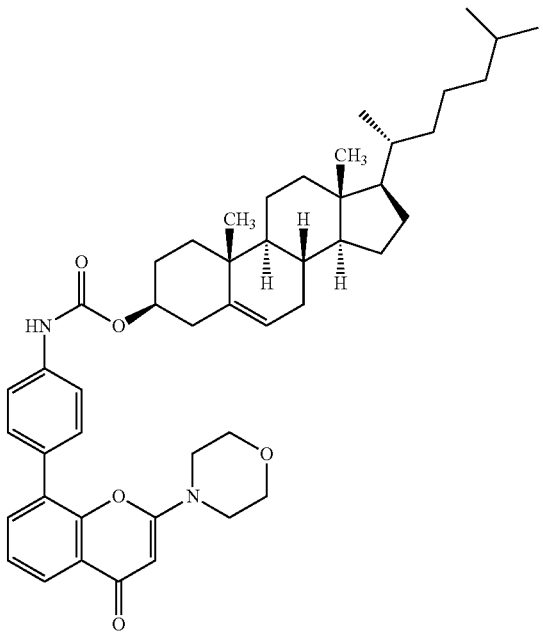

FORMULA I

10. The conjugate of any of paragraphs 6-8, having the structure of Formula II:

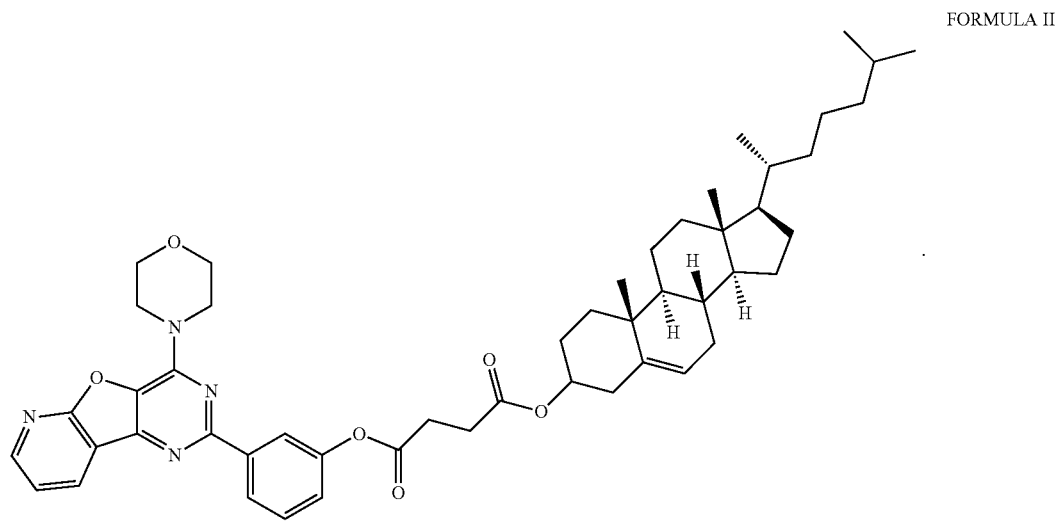

FORMULA II

11. The conjugate of any of paragraphs 1-5, wherein the chemotherapeutic agent is a taxane.

12. The conjugate of paragraph 11, wherein the taxane is paclitaxel or docetaxel.

13. The conjugate of paragraph 12, having the structure of Formula III:

FORMULA III

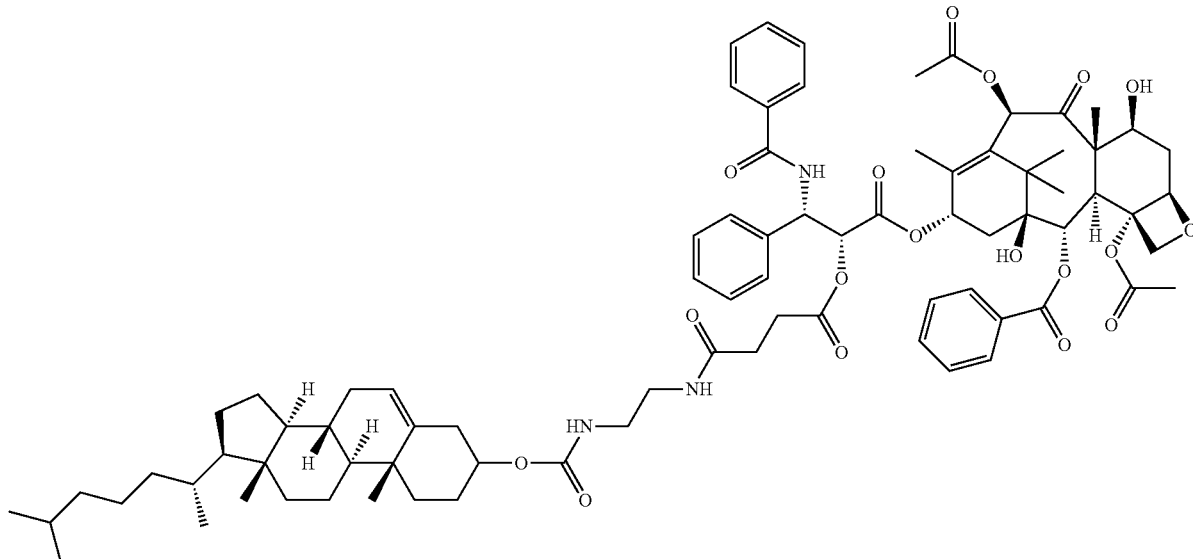

14. A composition comprising a conjugate of any of paragraphs 1-13.
15. The composition of paragraph 14, wherein the composition comprises about 1% to about 99% (w/w) of the conjugate.
16. The composition paragraph 14 or 15, wherein the composition further comprises a lipid in addition to the conjugate.
17. The composition of paragraph 16, wherein the composition comprises about 1% to about 99% (w/w) of the lipid.
18. The composition of paragraph 16 or 17, wherein the composition comprises the conjugate and the lipid in about 10:1 to about 1:10 ratio.
19. The composition of any of paragraphs 16-18, wherein the lipid is a lipid conjugated with polyethylene glycol (PEG).
20. The composition of paragraph 19, wherein the PEG conjugated lipid is selected from the group consisting of PEG conjugated diacylglycerols and dialkylglycerols, PEG-conjugated phosphatidylethanolamine and phosphatidic acid, PEG conjugated ceramides, PEG conjugated dialkylamines, PEG conjugated 1,2-diacyloxypropan-3-amines, and any combinations thereof.
21. The composition of paragraph 20, wherein the PEG conjugated lipid is 1,2-distearoyl-sn-glycem-3-phosphoethanolamine-N-[amino(polyethylene glycol)-2000] (DSPE-PEG2000).
22. The composition of any of paragraphs 14-21, wherein the composition further comprises a phospholipid.
23. The composition of paragraph 14, wherein the composition comprises about 1% to about 99% (w/w) of the phospholipid.
24. The composition of paragraph 22 or 23, wherein the composition comprises the conjugate and the phospholipid in about 10:1 to about 1:10 ratio.
25. The composition of any of paragraphs 22-24, wherein the composition comprises the phospholipid and the lipid in about 10:1 to about 1:10 ratio.
26. The composition of paragraph 25, wherein the phospholipid is selected from phosphatidyl cholines, phosphatidyl cholines with acyl groups having 6 to 22 carbon atoms, phosphatidyl ethanolamines, phosphatidyl inositols, phosphatidic acids, phosphatidyl serines, sphingomyelin, phosphatidyl glycerols, and any combinations thereof.
27. The composition of paragraph 26, wherein the phospholipid is selected from the group consisting of phosphatidylcholine, phosphatidylglycerol, lecithin, β,γ-dipalmitoyl-α-lecithin, sphingomyelin, phosphatidylserine, phosphatidic acid, N-(2,3-di(9-(Z)-octadecenyloxy))-prop-1-yl-N,N,N-trimethylammonium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, dimyristoyl phosphatidyl choline (DMPC), dioleoylphosphatidylethanolamine (DOPE), palmitoyloleoylphosphatidylcholine (POPC), egg phosphatidylcholine (EPC), distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), -phosphatidylethanolamine (POPE), dioleoyl-phosphatidylethanolamine 4-(N-maleimidomethyl)-cyclohexane-1-carboxylate (DOPE-mal), and any combinations thereof.
28. The composition of paragraph 27, wherein the phosphatidylcholine is L-a-phosphatidylcholine.
29. The composition of any of paragraphs 14-28, further comprising a targeting agent.
30. The composition of paragraph 29, wherein the targeting agent is selected from the group consisting of peptides, polypeptides, proteins, enzymes, peptidomimetics, glycoproteins, antibodies (monoclonal or polyclonal) and portions and fragments thereof, lectins, nucleosides, nucleotides, nucleoside and nucleotide analogues, nucleic acids, monosaccharides, disaccharides, trisaccharides, oligosaccharides, polysaccharides, lipopolysaccharides, vitamins, steroids, hormones, cofactors, receptors, receptor ligands, and analogs and derivatives thereof 31. The composition of paragraph 30, wherein the targeting agent is iRGD.
32. The composition of any of paragraphs 14-31, wherein the composition comprises two or more different conjugates of any of paragraphs 1-13.
33. The composition of any of paragraphs 14-32, wherein the composition further comprises an anticancer agent in addition to the conjugate.
34. The composition of paragraph 33, wherein the anticancer agent is a platinum compound, paclitaxel; carboplatin; bortezomib; vorinostat; rituximab; temozolomide; rapamycin; an alkylating agent; cyclophosphamide; an alkyl sulfonate; busulfan; improsulfan; piposulfan; an aziridine; an ethylenimine; a methylamelamine; an acetogenin; a camptothecin; a cryptophycin; a nitrogen mustard; a nitrosurea; an antibiotic; a enediyne antibiotic; a bisphosphonate; doxorubicin; a mitomycin; an anti-metabolite; a folic acid analogue; a purine analog; a pyrimidine analog; an androgen; an anti-adrenal; an epothilone; a maytansinoid; a trichothecene; gemcitabine; 6-thioguanine; mercaptopurine; methotrexate; vinblastine; etoposide; ifosfamide; mitoxantrone; vincristine; vinorelbine; novantrone; teniposide; edatrexate; daunomycin; aminopterin; xeloda; ibandronate; irinotecan; a topoisomerase inhibitor; a retinoid; capecitabine; combretastatin; leucovorin; lapatinib; and erlotinib.
35. The composition of paragraph 34, wherein the platinum compound is of formula (IV):

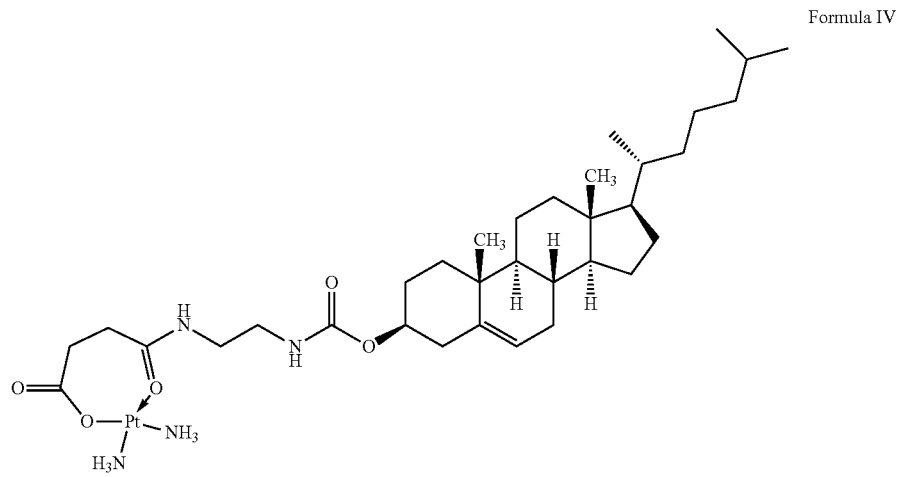

Formula IV

36. The composition of any of paragraphs 14-35, wherein the composition further comprises a neutral lipid, a cationic lipid, an anionic lipid, an amphiphilic lipid, a sterol, or a programmable fusion lipid.
37. The composition of any of paragraphs 14-36, wherein the composition comprises the conjugate, a PEG conjugated lipid, and a phospholipid.
38. The composition of paragraph 37, wherein the PEG conjugated lipid is DSPE-PEG2000 and the phospholipid is phosphatidylcholine.
39. The composition of paragraph 37 or 38, wherein the composition comprises the conjugate, the PEG conjugated lipid, and the phospholipid in ratio from about 10-0.1:10-0.1:10-0.1.
40. The composition of paragraph 39, wherein the ratio is about 1.4:1:3 or about 10:5:1.
41. The composition of any of paragraph 14-38, wherein the composition is a nanoparticle.
42. The composition of paragraph 41, wherein the nanoparticle is about 5 nm to about 500 nm in diameter.
43. The composition of paragraph 41, wherein the nanoparticle is less than about 200 nm in diameter.
44. A pharmaceutical composition comprising the composition of any of paragraphs 1-43, and optionally, a pharmaceutically acceptable carrier.
45. A method of treating cancer, comprising, administering a composition of any of paragraphs 1-43 to a patient in need of treatment for cancer.
46. The method of paragraph 45, wherein the cancer is selected from the group consisting of:
    breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.
47. The method of any of paragraphs 45-46, wherein the subject has been determined to have tumor cells with aberrant PI3K.
48. The method of any of paragraphs 45-47, further comprising co-administering one or more additional anticancer therapy to the patient.
49. The method of paragraph 48, wherein the additional therapy is selected from the group consisting of surgery, chemotherapy, radiation therapy, thermotherapy, immunotherapy, hormone therapy, laser therapy, anti-angiogenic therapy, and any combinations thereof.
50. The method of paragraph 48 wherein the additional therapy comprises administering an anti-cancer agent to the patient.
51. A method of reducing blood glucose levels, comprising administering a composition of any of paragraphs 1-43, to a subject in need of a reduction of blood glucose levels.

52. The use of a composition of any of paragraphs 1-43 to treat cancer, the method comprising administering a composition of any of paragraphs 1-43 to a patient in need of treatment for cancer.
53. The use of paragraph 52, wherein the cancer is selected from the group consisting of:
breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.
54. The use of any of paragraphs 52-53, wherein the subject has been determined to have tumor cells with aberrant PI3K.
55. The use of any of paragraphs 52-54, further comprising co-administering one or more additional anti-cancer therapy to the patient.
56. The use of paragraph 55, wherein the additional therapy is selected from the group consisting of surgery, chemotherapy, radiation therapy, thermotherapy, immunotherapy, hormone therapy, laser therapy, anti-angiogenic therapy, and any combinations thereof.
57. The use of paragraph 55, wherein the additional therapy comprises administering an anti-cancer agent to the patient.
58. The use of a composition of any of paragraphs 1-43 to reduce blood glucose levels, comprising administering a composition of any of paragraphs 1-43, to a subject in need of a reduction of blood glucose levels.

EXAMPLES

Example 1: Enhancing Anti-Tumor Efficacy Via Temporal Inhibition of Phosphatidylinositol 3 Kinase Using a Supramolecular Nanoparticle In this study, we demonstrate the potential advantages of the rational design of supramolecular nanoparticles that target the phosphatidylinositol 3 kinase (PI3K) pathway. Since its discovery 20 years ago, studies have established the centrality of the PI3K family of lipid kinases in the etiology of cancer (6). Of the three classes of PI3K, Class IA PI3K is the one most implicated in driving human cancers (7).

PIK3CA, which encodes the p110α catalytic subunit of PI3K, and PIK3R1, which codes for the regulatory p85a subunit, are somatically mutated or amplified in multiple primary tumors, including in breast, gliomas, gastrointestinal, prostate and gynecological cancers (7). Additional modulators of the PI3K signaling pathway are also commonly deregulated in multiple malignancies. For example, the lipid phosphatase PTEN, an inhibitor of PI3K signaling, is a commonly inactivated tumor suppressor (8). Activation of this pathway can also occur at the level of mutated or amplified tyrosine receptor kinases or through mutations of AKT and RAS (7). Consequently, small molecule inhibitors that target PI3K pathway have emerged as an exciting area of research, and several molecules that either inhibit specific catalytic subunits (a,13.8,y) of p110 or act as pan-PI3K inhibitors are currently in development (9).

However, recent studies have implicated p110α as also playing a predominant role in glucose homeostasis (10). Indeed, recent data from a Phase I clinical study with a pan-class I selective PI3K inhibitor (NVP-BKM120) indicates dose-dependent hyperglycemia, possibly an example of a class effect consistent with PI3K inhibition (11). Furthermore, studies have reported that approximately 10-fold higher concentration of PI3K inhibitors might be required to block phosphorylation of downstream pathway proteins such as ribosomal protein S6 than that needed for inhibiting more proximal AKT phosphorylation (12). We rationalized that a natural approach to overcome these challenges associated with targeting the PI3K pathway is through the use of nanotechnology.

Nanostructures can capitalize on the unique leaky angiogenic tumor vasculature coupled with impaired intratumoral lymphatic drainage, resulting in increased intratumoral drug concentrations arising from the enhanced permeation and retention (EPR) effect (13). However, traditional processes for nanoformulation are often incompatible with physicochemical properties of many chemotherapeutic agents, which can limit the entrapment efficiency or introduce sub-optimal release kinetics. Indeed, our early attempts in entrapping LY294002, one of the earliest and still widely used PI3K inhibitors, resulted in sub-optimal loading efficiencies that prevented translation to in vivo tumor efficacy studies (14). Similarly, in a recent study, wortmannin-encapsulated polymeric nanoparticles were shown to act as a radiosensitizer (15), but such formulations are limited by total release within a short time period, which would complicate clinical translation.

In a recent study, we demonstrated a new paradigm moving beyond traditional encapsulation strategies to the rational re-design of molecules to facilitate supramolecular assembly in the nanoscale dimension (16). This concept of supramolecular nanochemistry was first envisioned by Jean Marie Lehn, who postulated that complex nanostructures could evolve from molecular building blocks that interact via non-covalent intermolecular forces (17, 18). Here we report that rational modification of PI3K inhibitors following conjugation with cholesterol enables supramolecular assembly into a nanoparticle. Such PI3K-targeting supramolecular nanoparticles (SNPs) exhibit the desired pharmacodynamic profile with enhanced antitumor efficacy, and can emerge as a new paradigm in targeted molecular therapeutics development.

Synthesis and Characterization of PI3K-Inhibiting SNPs.

Figure 1B:
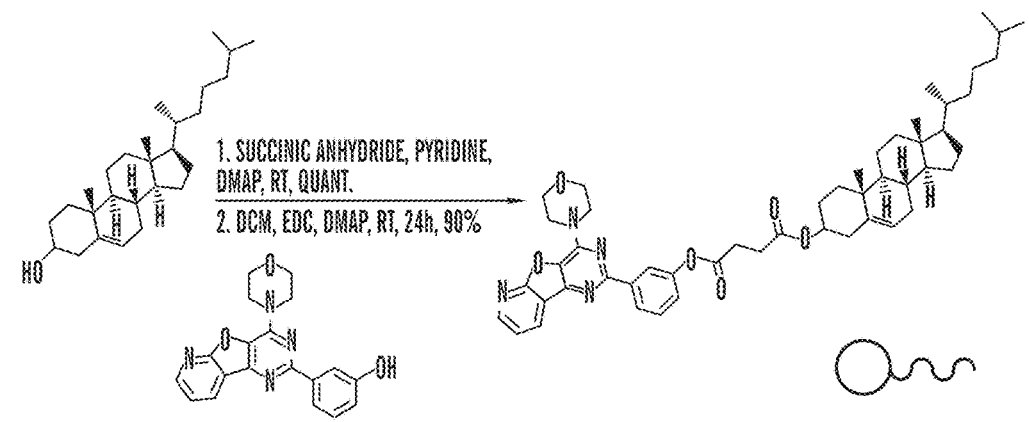
Figure 5:
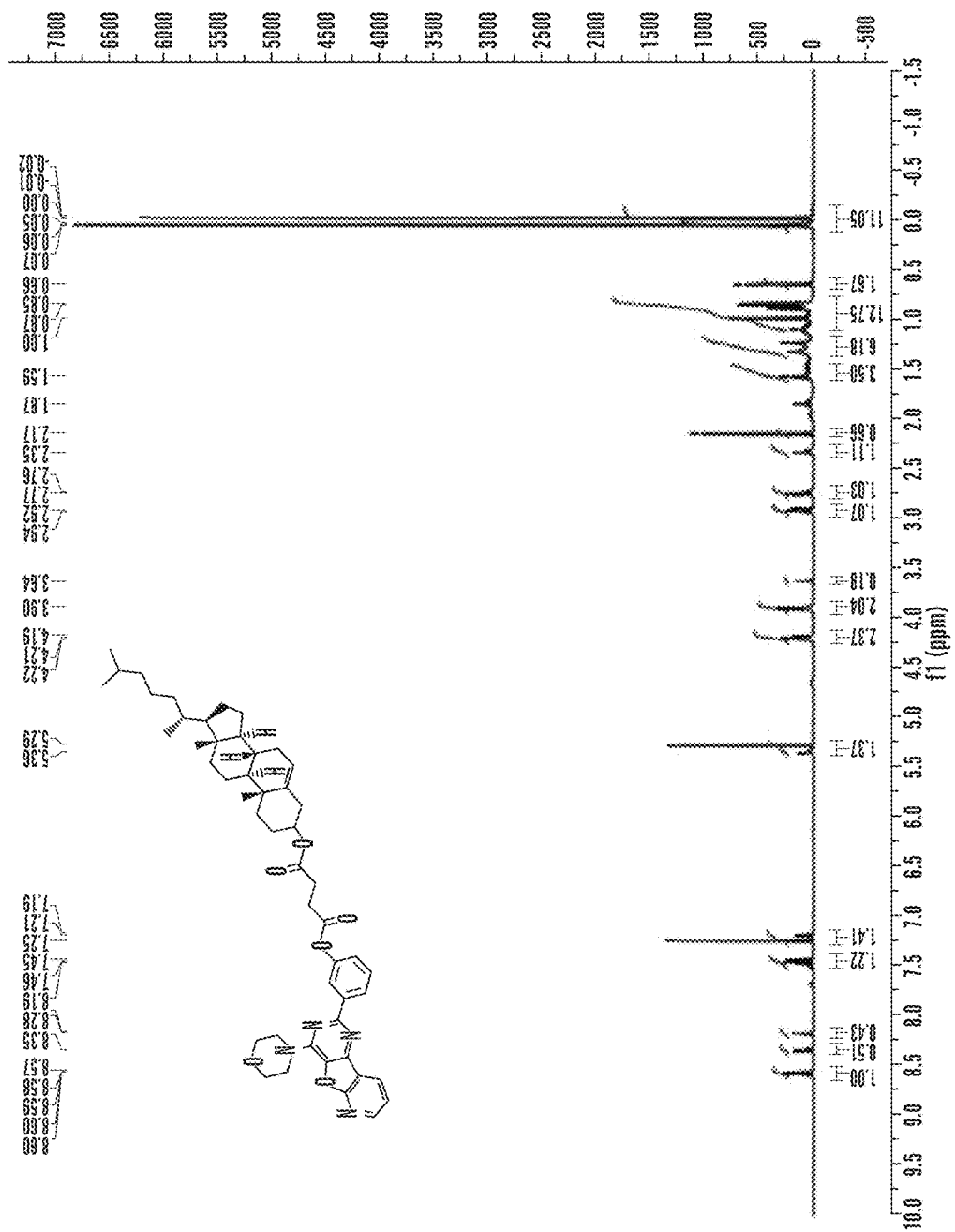
FIG. 5 depicts the $^1$H NMR spectra of PI103-cholesterol conjugate
Figure 6:
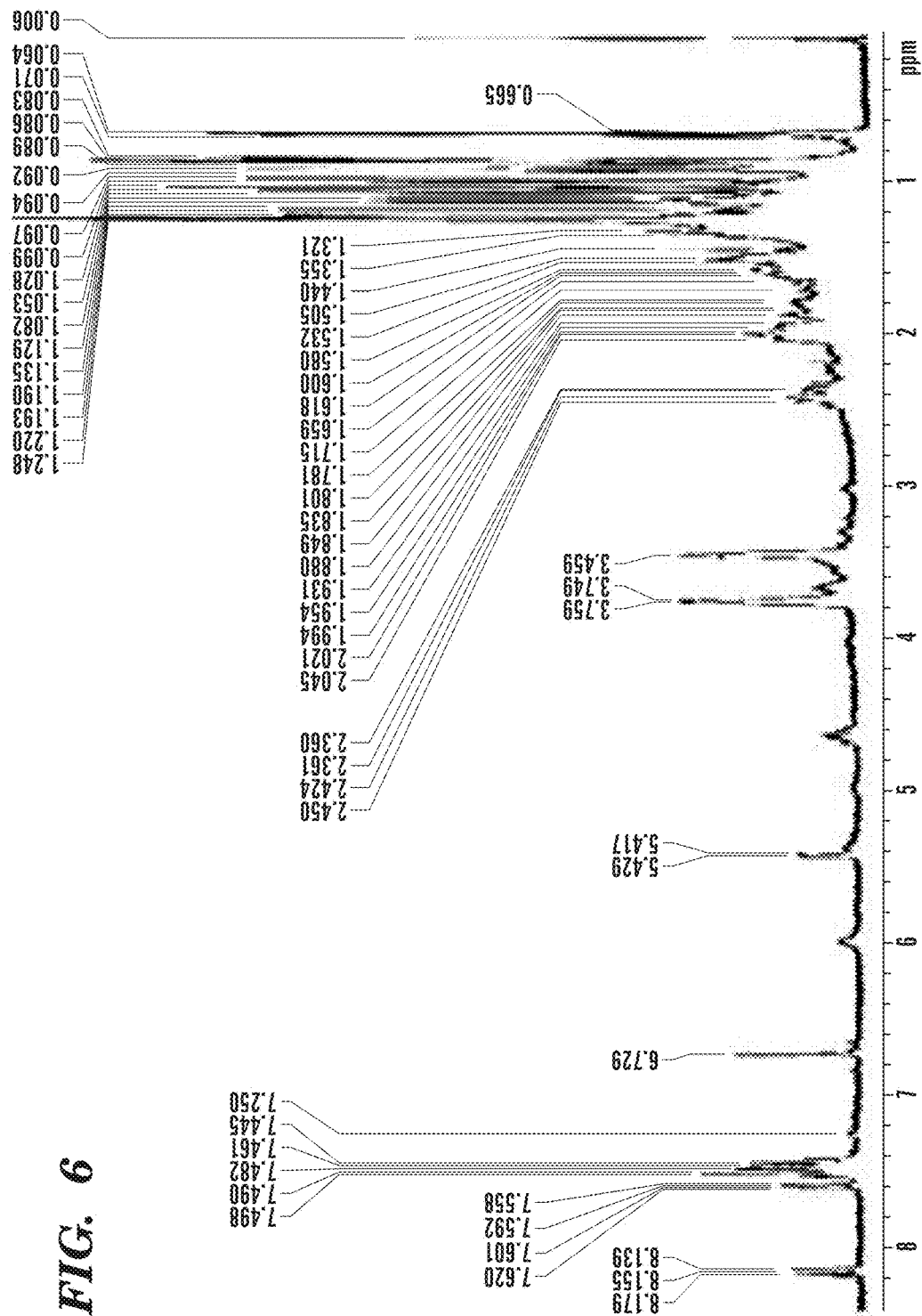
FIG. 6 depicts the $^1$H NMR spectra of PI828-cholesterol conjugate
Figure 7:
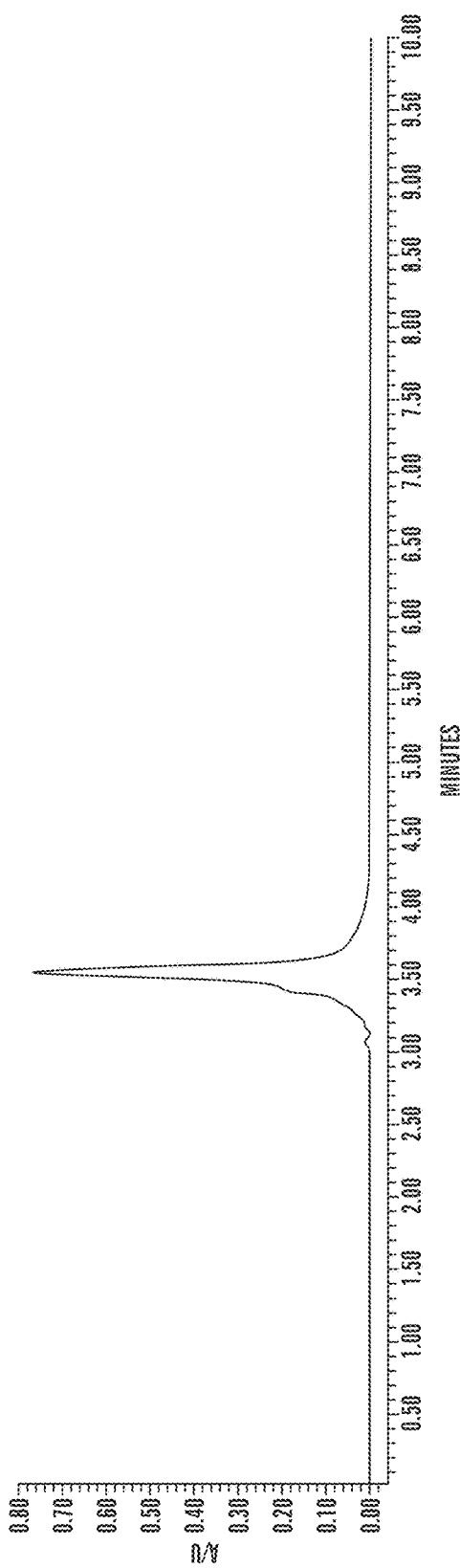
FIG. 7 depicts the HPLC graph of PI103-cholesterol conjugate.

In the current study, we used two different PI3K inhibitors, the pyridofuropyrimidine PI103, and PI828 (8-bromo-2-morpholin-4-yl-chromen-4-one) to engineer the supramolecular nanoparticles. PI828 is a derivative of the earlier generation and widely used PI3K inhibitor LY294002, where an amine linker has been inserted in 4-position hydrogen of the exocyclic phenyl substituent, enabling conjugation to cholesterol via a carbamate bond (FIG. 1A). Previous studies have demonstrated that conjugation via this linker maintains affinity for the catalytic site of PI3K class I isoforms (19). However, PI828, like LY294002, is a weak inhibitor (19). We therefore included, PI103, which has been reported to exhibit excellent potency in the low nanomolar range and selectivity for class IA PI3Ks as well as mTOR (12). However, PI103 was not found suitable for clinical development as the planar tricyclic structure resulted in limited aqueous solubility and the phenolic hydroxyl group is rapidly glucoronidated (12). These traits, however, made PI103 a perfect molecule to engineer the supramolecular nanoparticles. As shown in FIG. 1B, the phenolic hydroxyl group was conjugated via an ester linkage to cholesterol-succinate complex. The intermediate and products were characterized by 1H, 13C NMR spectroscopy and mass spectrometry (FIGS. 5-7).

We engineered the SNPs from the cholesterol-PI828 or cholesterol-PI103 conjugates, phosphatidylcholine (PC) and 1,2-distearoyl-sn-glycem-3-phosphoethanolamine-N-

Figure 1F:
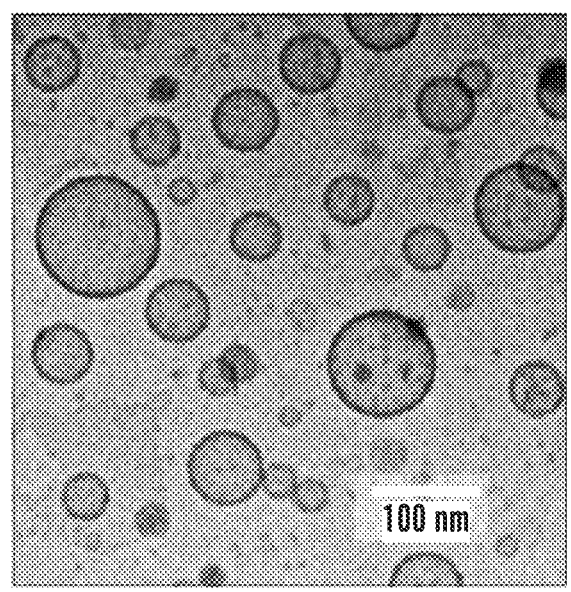
Figure 1G:
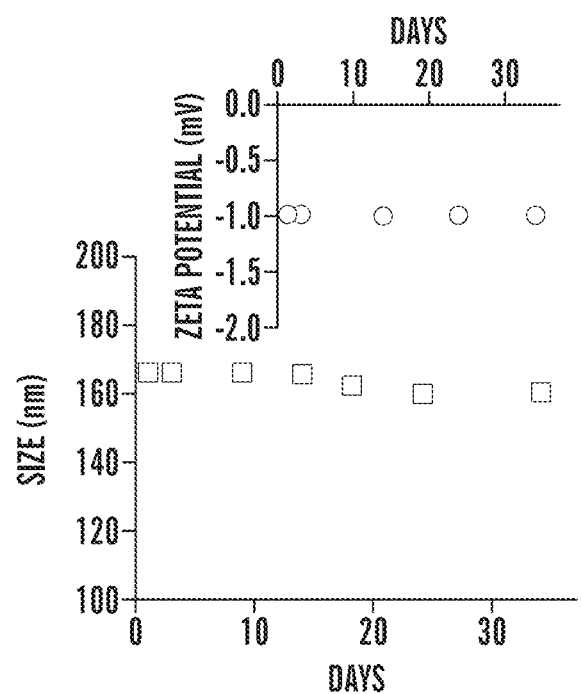

[amino(polyethylene glycol)-2000] (DSPE-PEG2000) at optimized weight ratios using a lipid-film hydration self assembly method (20)(FIG. 1C). The incorporation efficiency for the cholesterol-PI828 SNPs was 43%, and 60±5% for PI103-cholesterol conjugate SNPs. As shown in FIG. 1D, cholesterol-PI828 conjugates resulted in the formation of SNPs with hydrodynamic diameter of 108±8.9 nm as determined by dynamic light scattering (FIG. 1D). PI103-SNPs showed a mean particle diameter of 172±1.8 nm (FIG. 1E). Ultrastructure analysis using cryo-transmission electron microscopy (cryo-TEM) (FIG. 1F) revealed the formation of predominantly unilamellar structures 100 nm or less in diameter. The size difference between TEM and DLS measurements can be attributed to the hydration sphere arising from the PEG coating, which can facilitate the masking from the reticuloendothelial system (21). Additionally, aliquots of the PI103-SNPs were stored for a period of over a month, and the size and zeta potential was measured periodically as a measure of stability of the nanostructure. As show in FIG. 1G, no significant temporal variation was observed in either size or zeta potential during this period, indicating that the formulations were stable.

Figure 1H:
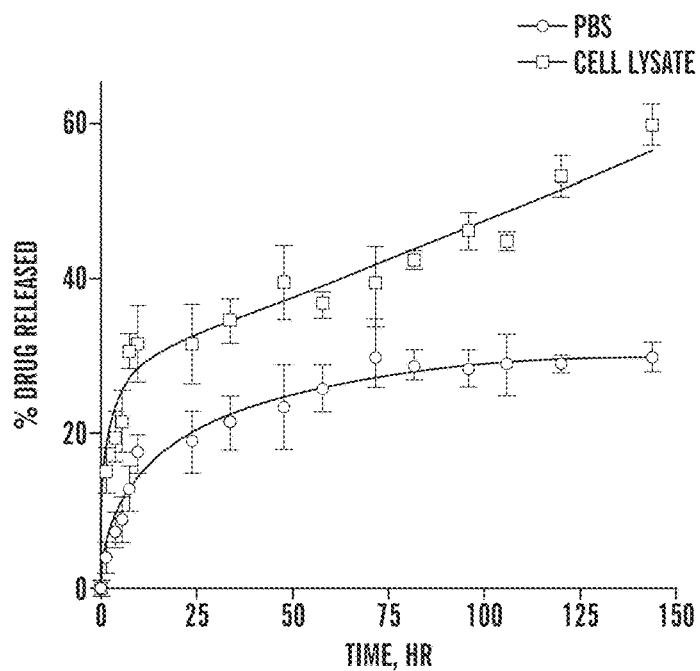
Figure 1I:
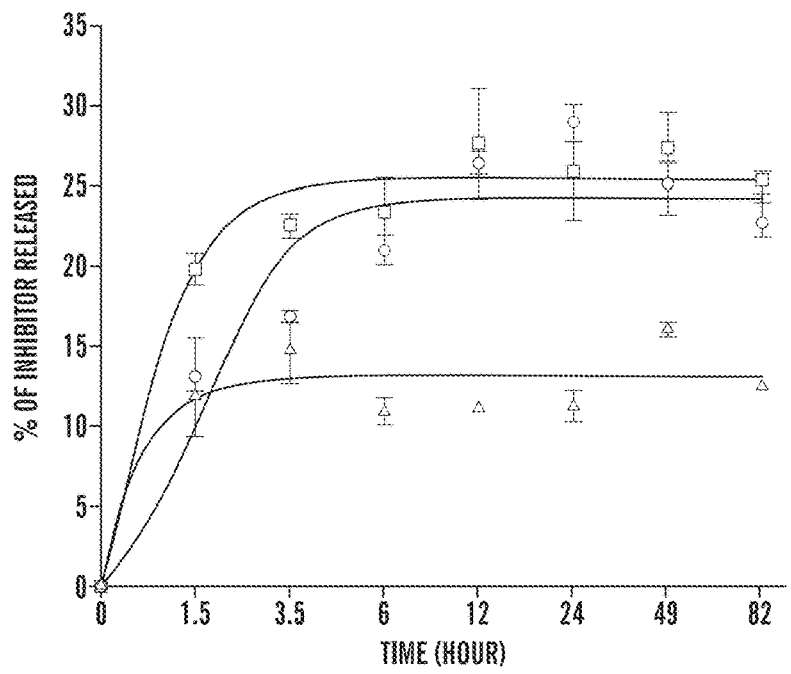

To study the temporal kinetics of PI3K inhibitor release, the SNPs were incubated either in phosphate buffer saline or in cell lysate. While the amount of drug released in PBS was saturated at ~20%, a sustained release of drug was observed in cell lysate (FIGS. 1H, 1I), consistent with the cleavage of the linkers in acidic and enzymatic (esterase) conditions. Interestingly, while a sustained and increasing drug release was observed with PI103-SNP, the rate of release of PI828 was significantly lower. This is consistent with the carbamate linker between the drug and cholesterol, which is more stable than the ester linkage in the PI103-SNPs.

Figure 8D:
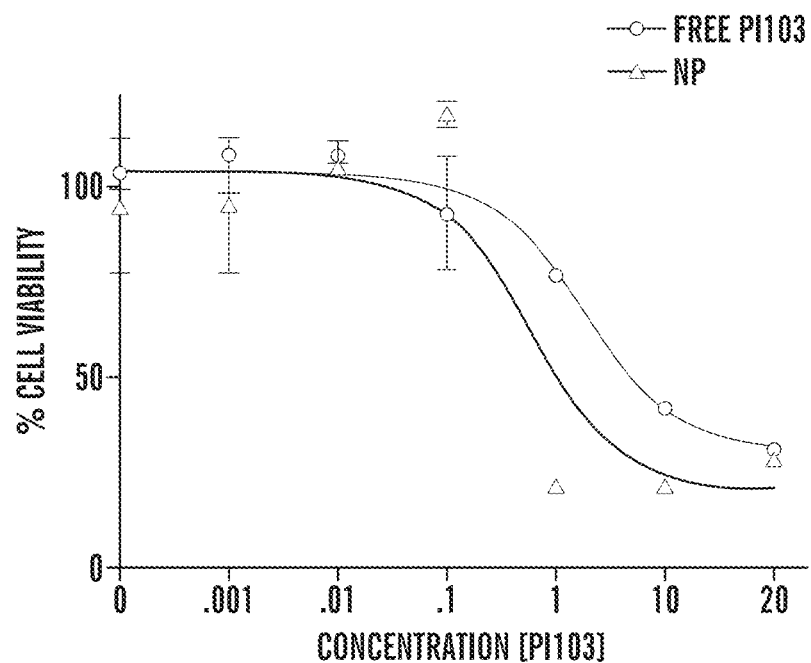
Figure 8E:
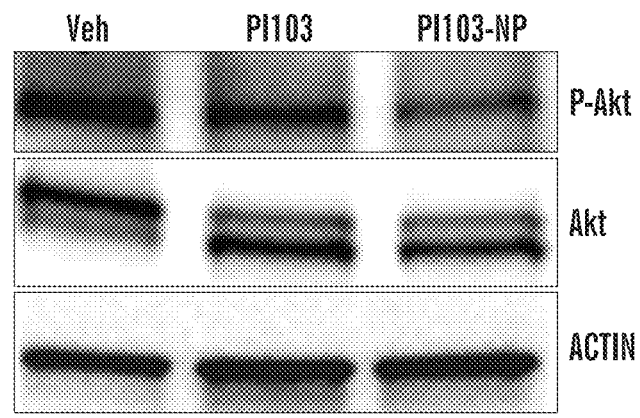
Figure 8F:
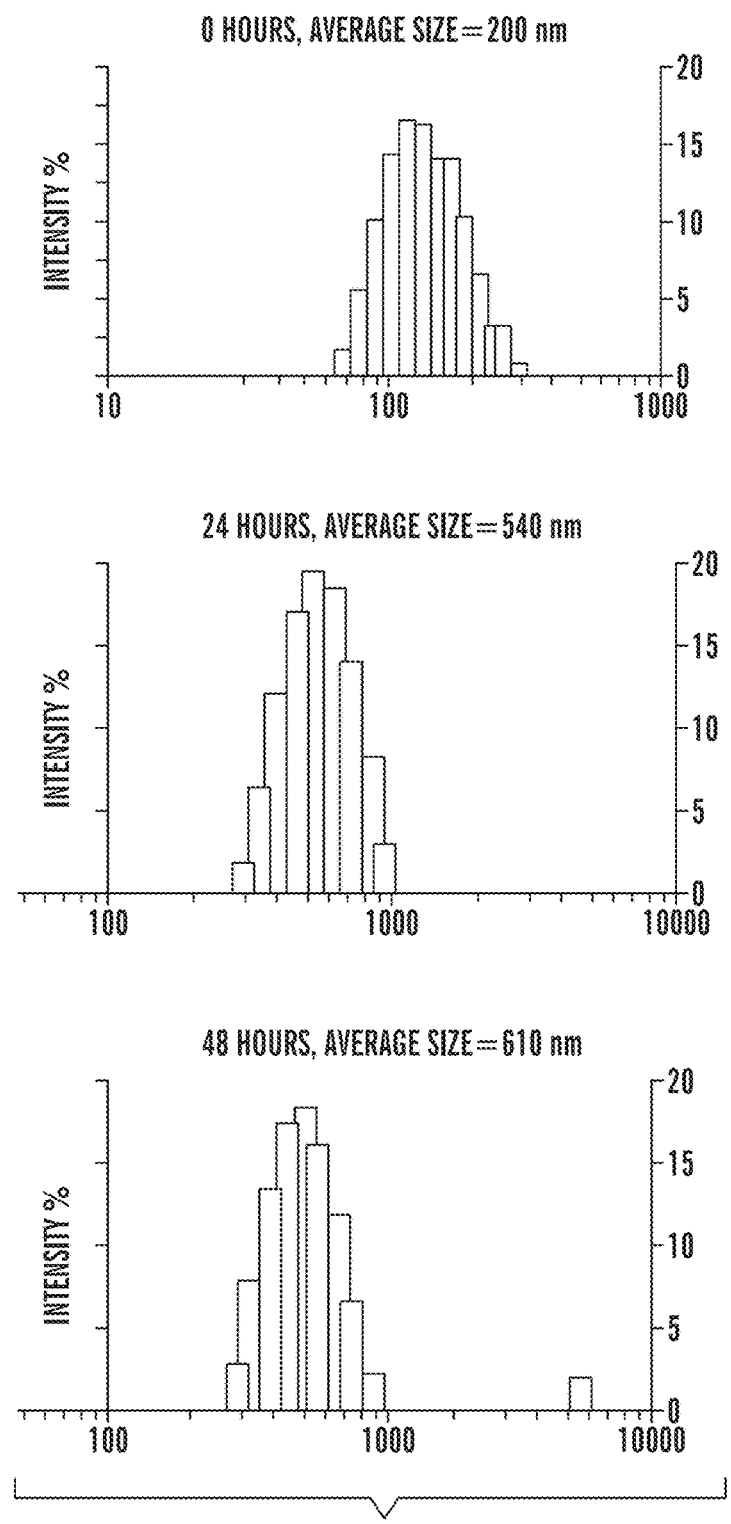

As a control experiment, we also engineered nanoparticles, in which we encapsulated PI103 in the lipid bilayer (FIG. 8A). Using the lipid ratio employed with the SNPs, however, resulted in minimal incorporation efficiency of 2% PI103, which could be optimized to 30% by changing the compositional ratio (FIG. 8B). As shown in FIG. 8C, a sustained release of PI103 was observed from the formulation. While the PI103-encapsulated nanoparticles exhibited similar effects on cell viability (FIG. 8D) and inhibition of Akt phosphorylation in vitro (FIG. 8E), temporal light scattering studies revealed an increase in the size of the nanoparticles with time (FIG. 8F), which indicated that these nanoparticles are unstable and precipitate out (data not shown). As a result, further studies with this nanoparticle design were not pursued.

Figure 2A:
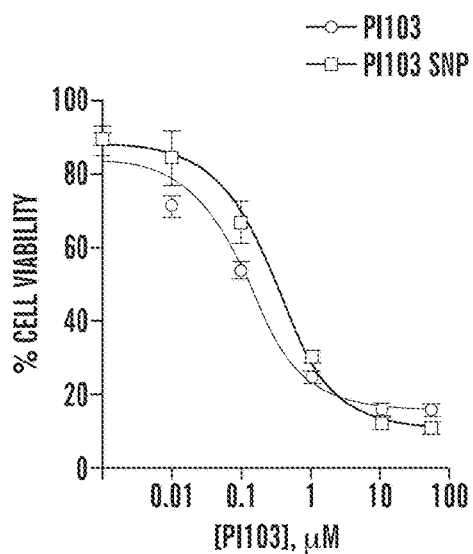
FIGS. 2A-2O demonstrate the in vitro characterization of PI3K-inhibiting SNPs. MTS assay showing the effect of free PI103 or PI103-SNPs at different concentrations on 4T1 cells at 48 h (FIG. 2A) and 72 h (FIG. 2B), 468 cells at 48 h (FIG. 2C) and 72 h (FIG. 2D) and 4306 cells at 48 h (FIG. 2E) and 72 h (FIG. 2F), (FIG. 2G) Expression of phospho-AKT and total AKT in 4T1 cells at 3, 9, 24 and 48 hours after treatment with either 5 μM free PI103 or PI103-SNP. Effect of acute treatment (4-hour incubation) with (FIG. 2H, 2I) free PI103 or (FIG. 2J, 2K) PI103-SNP on temporal PI3K activity. After 4 hours of exposure to the drug, the cells were washed thrice with cold PBS to remove drug remaining outside the cells. The cells were then incubated with fresh media containing 1% FBS and collected at 0, 12, 24, 36 and 48 hours for analysis. PI103-SNPs expressed sustained inhibition of AKT activation continuing even at 48 hours.
Figure 2B:
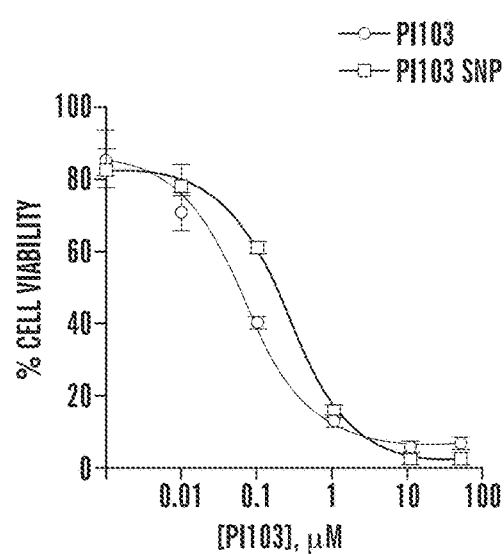
(FIG. 2L) Graph showing internalization of free PI103 and PI103 nanoparticles at 4 h and 18 h. The amount of drug internalized was measured by UV-vis spectroscopy; Statistical analysis was performed with student t-test. Error bars, Mean±SEM; n.s., not significant;*p<0.05; **p<0.01. Graphs show the effect of treatment with PI828 or PI828-SNPs on viability of (FIG. 2M) 4T1 breast cancer cells or (FIG. 2N) 4306 cells.
Figure 2C:
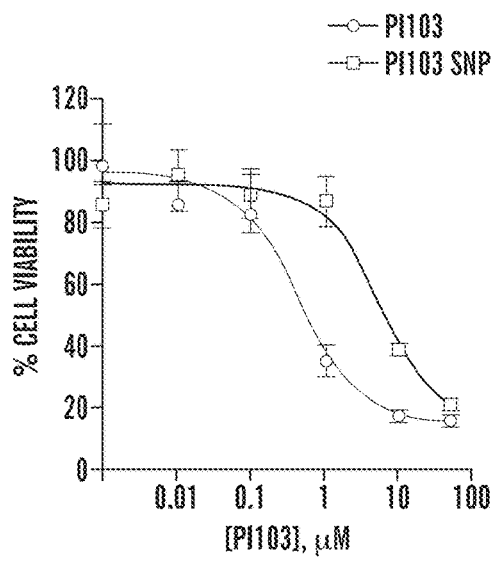
Figure 2D:
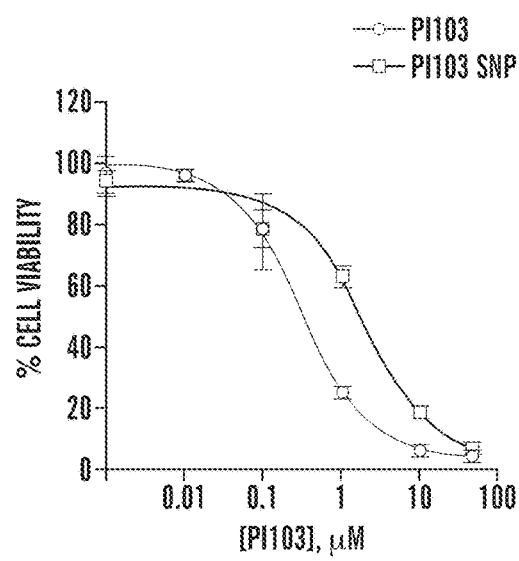
Figure 2E:
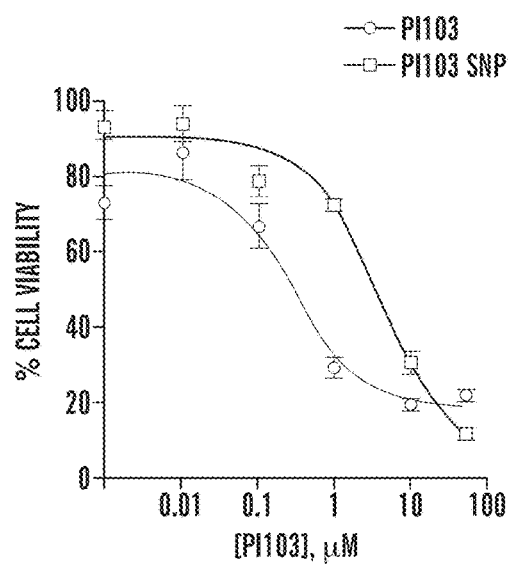
Figure 2F:
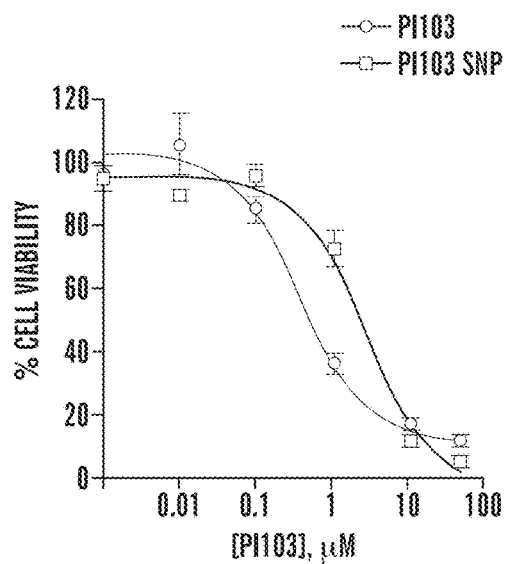
Figure 2G:
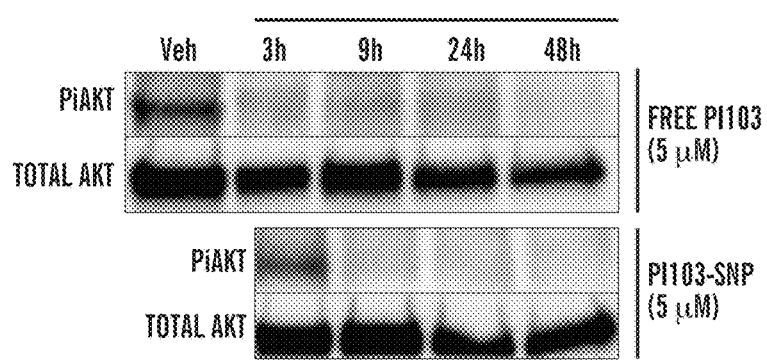
Figure 2H:
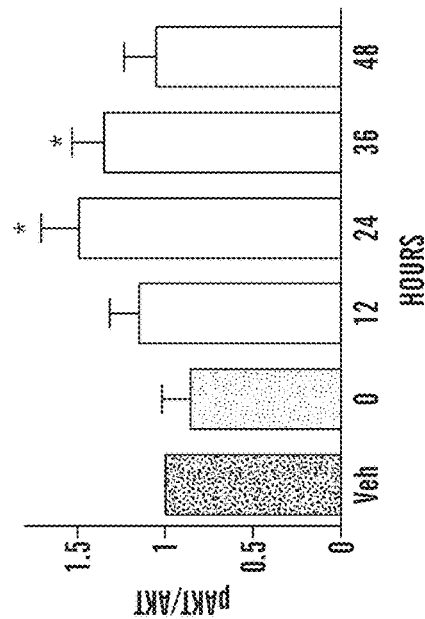
Figure 2I:
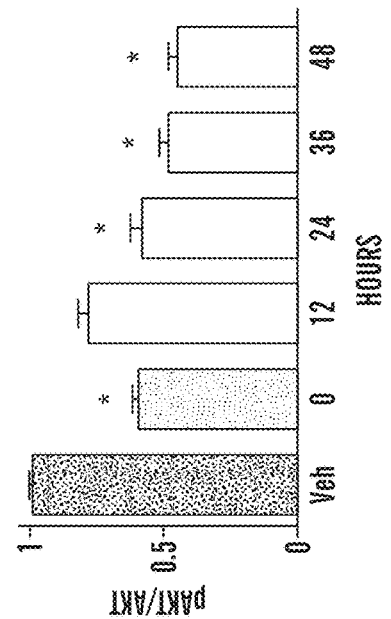
Figure 2J:
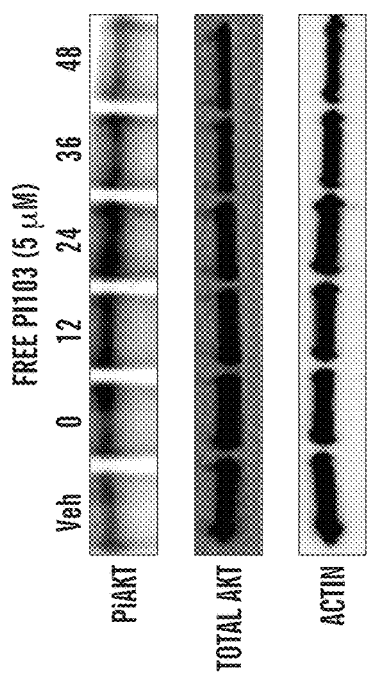
Figure 2K:
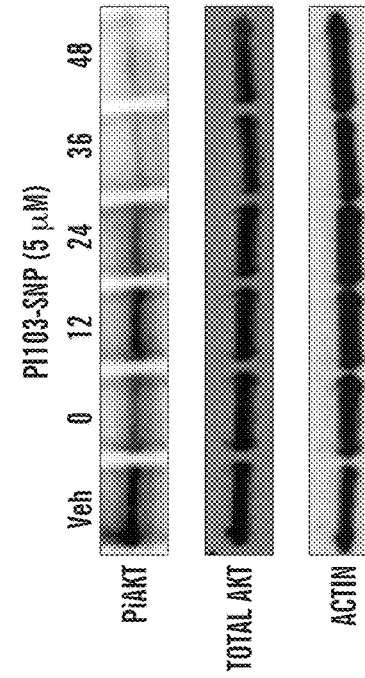
Figure 2M:
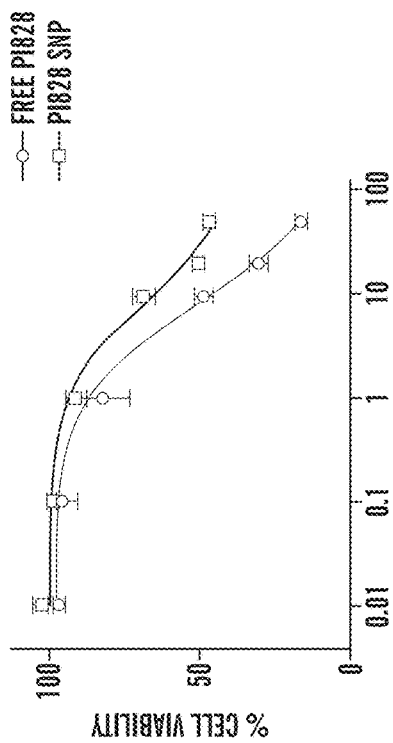
Figure 2O:
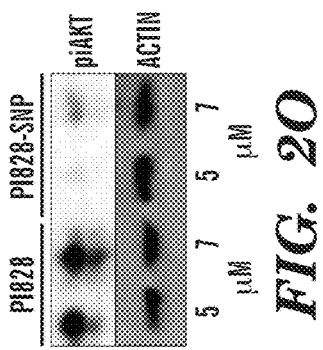
Figure 2L:
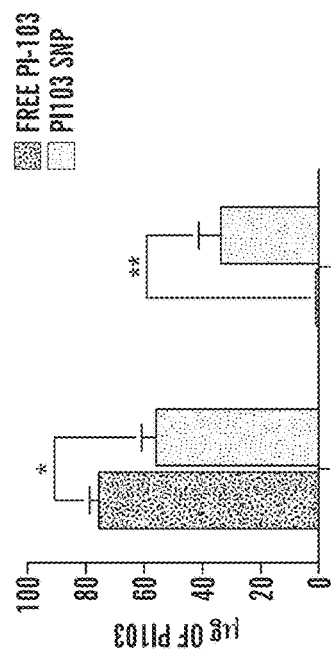
Figure 2N:
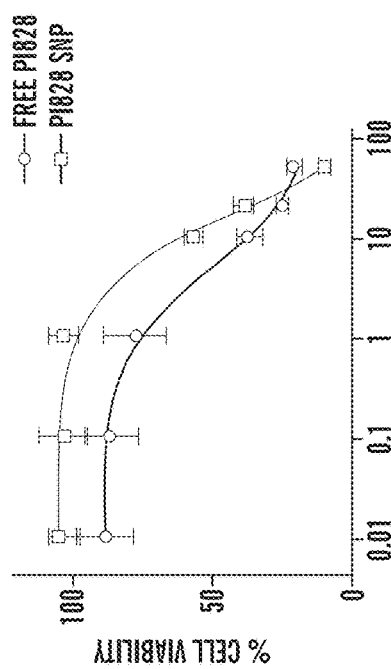

In Vitro Efficacy of Supramolecular Nanoparticles:

We evaluated the efficacy of the SNP in vitro using a 4T1 murine breast cancer, MDA-MB-468 human breast cancer cells and a PI3K-overexpressing 4306-ovarian cancer cell line. As shown in FIGS. 2A and 2B, IC50 values for free PI103 and PI103-SNP against 4T1 murine breast cancer cell line were 121.5±3.15 nM and 297.7±3.57 nM at 48 hours and 67.26±3.4 nM and 243.6±3.4 nM at 72 hours respectively. The IC50 values in MDA-MB-468 human breast cancer cell line treated with free PI103 and PI103-SNP were 0.445±0.067 pM and 6.686±0.0108 pM at 48 hours and 0.3121±0.049 pM and 2.049±0.044 pM at 72 hours respectively (FIGS. 2C and 2D). For 4306 ovarian cancer cell line, the IC50 values for free PI103 and PI103-SNPs were 0.2863±0.045 pM and 3.698±0.050 pM at 48 hours and 0.3916±0.0493 pM and 2.846±0.045 pM at 72 hours respectively (FIGS. 2E and 2F). Western blot analysis showed that at equimolar concentrations of PI103 (5 pM), both the free drug as well the SNP inhibited basal phosphorylation of Akt even at 48 hours of continuous incubation (FIG. 2G). Interestingly, on the other hand, a transient exposure of 4 hours resulted in a rebound increase in phosphorylation of AKT in the case of free PI103, while SNP-PI103 inhibited Akt phosphorylation in a more sustained manner (FIGS. 2H-2K). The intracellular concentration of PI103 at 4 hours was higher in the cells treated with the free drug than in SNP-PI103, but at 18 hours the PI103 concentration remained high in the PI103-SNP-treated cells, whereas only traces of the drug were detected in the cells treated with the free drug (FIG. 2L). Consistent with the above observations, PI828-SNPs and free PI828 exhibited similar cytotoxic effect on the 4T1 cells (FIG. 2M) and 4306 cells (FIG. 2N). The cells treated with PI103-SNPs and PI828-SN exhibited similar inhibition of Akt phosphorylation after 36 hours of treatment (FIG. 2O).

Efficacy of SNP in an In Vivo 4T1 Breast Cancer Model:

We next investigated the anti-tumor efficacy of PI103-SNPs in the 4T1 cell line, which is negative for ER and PR, and expresses a low level of the mouse Her2/neu equivalent (22). Transplanted into syngeneic mice, the 4T1 form aggressive, highly metastatic breast cancers. Mutations in genes that constitute the PI3K pathway occur in >70% of breast cancers (23). We have previously demonstrated that the 4T1 cells mount a survival response to standard chemotherapy via an upregulation of PI3K signaling (24).

Figure 3A:
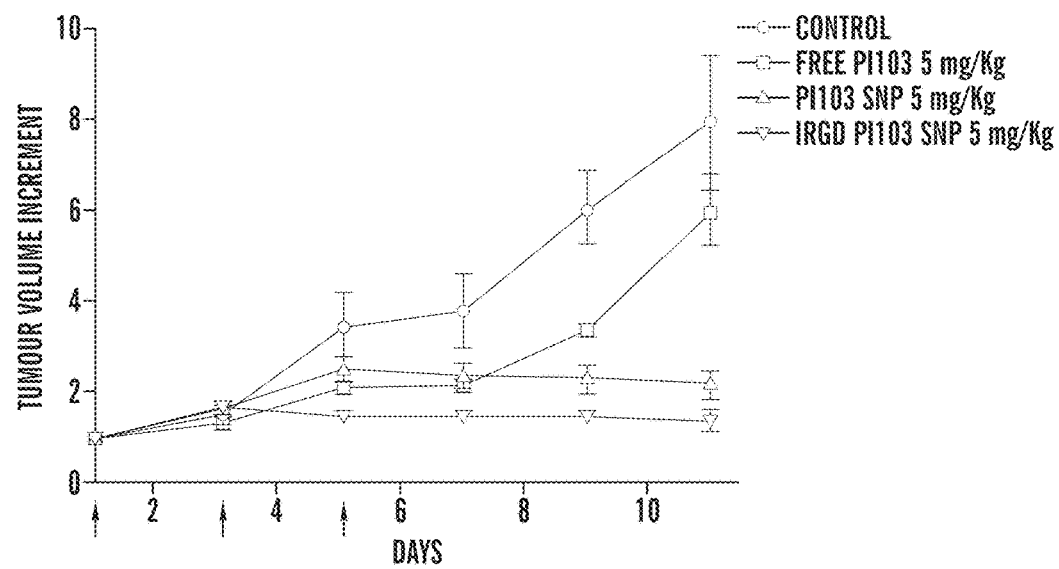
FIGS. 3A-3E.
Figure 3B:
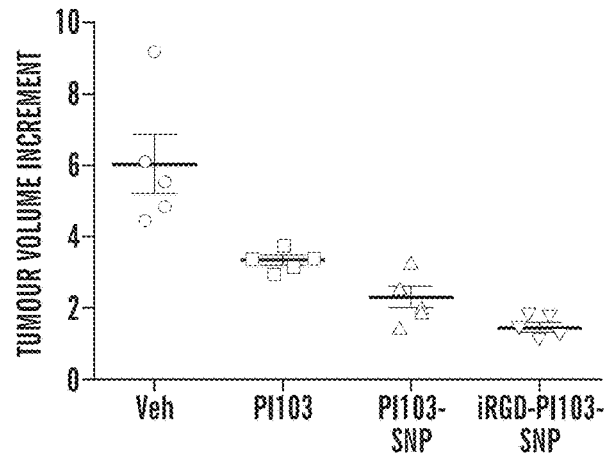
Figure 3C:
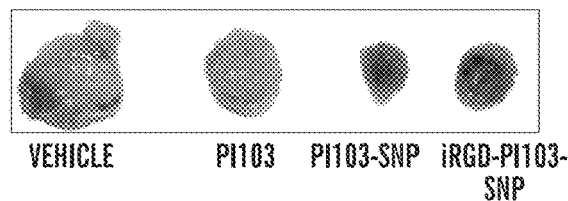
Figure 3D:
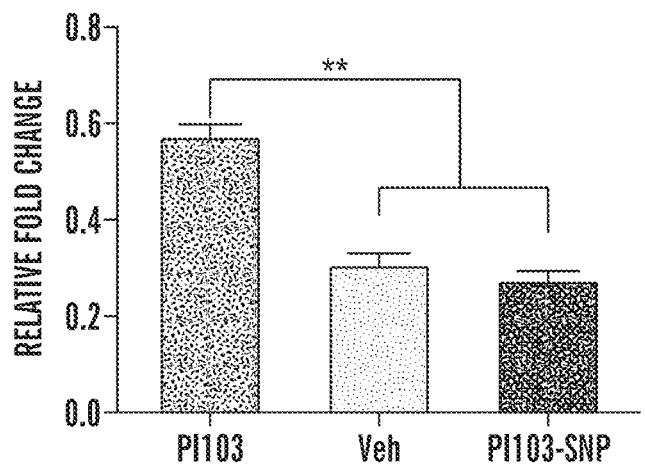
Figure 3E:
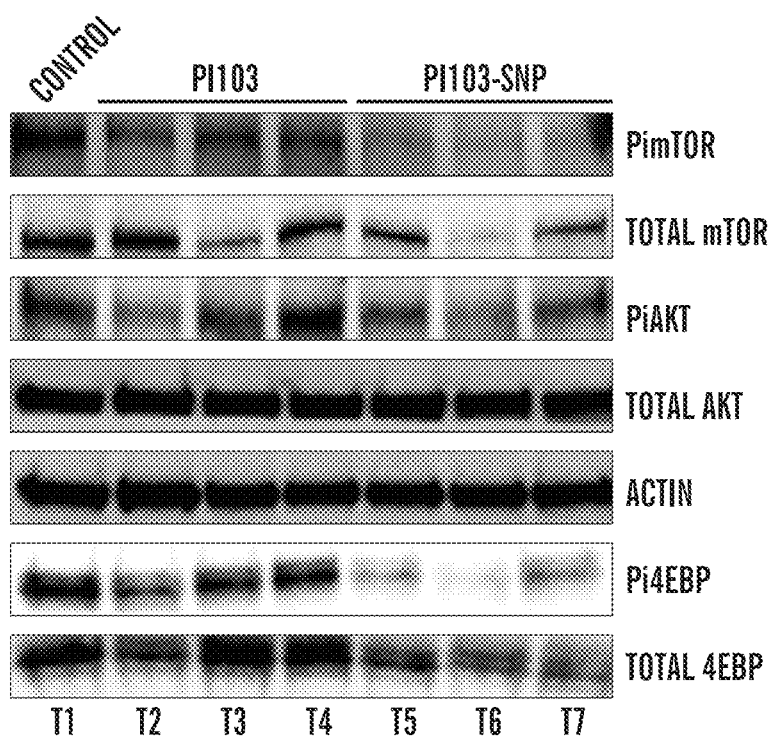

We treated mice with 4T1 tumors with a dose equivalent to 5 mg/kg of PI103 as free drug or as PI103-SNP. The treatment was started when the mean tumor volume had reached 100 mm³, As shown in FIGS. 3A-3C, treatment with PI103 resulted in tumor growth inhibition relative to PBS-treated controls, but tumor rebound was observed after the treatment was stopped. In contrast, treatment with PI103-SNP resulted in sustained tumor growth inhibition over the study period. This was consistent with the sustained level of the drug in the SNP group. After a single injection, intratumoral Akt phosphorylation was inhibited by both the free drug and PI103-SNP compared to the vehicle-treated group (FIG. 3E). PI103 seemed more efficient, but the difference was not statistically significant. Interestingly, the phosphorylated forms of downstream signaling molecules, mTOR and 4EBP, were more strongly inhibited in the PI103-SNP-treated group than in the PI103-treated tumors (P<0.05, t test).

To test whether targeting the nanoparticles to the tumor using 'homing' peptides increases antitumor efficacy, a separate group of tumor mice were treated with PI103-SNPs that were surface-decorated with iRGD peptide. As shown in FIGS. 3A-3C, such a treatment resulted in greater tumor inhibition than what was obtained with SNPs that accumulate via passive uptake. Indeed, previous observations have shown that iRGD-coated nanostructures exhibit increased extravasation and tissue penetration in a tumor-specific and neuropilin-1-dependent manner (25). Epifluorescence imaging of tumor cross-sections revealed significant intra-tumoral localization of FAM-labeled iRGD coated PI103-SNPs (data not shown). To elucidate the mechanism underlying the increased in vivo efficacy, the tumors were excised post-treatment, and processed for terminal deoxynucleotidyl transferase dUTP nick end labeling (TUNEL) as a marker for apoptosis. Treatment with PI103-SNPs resulted in greater apoptosis than treatment with free PI103. iRGD-coated PI103-SNPs induced highest level of apoptosis, followed by PI103 nanoparticles and free PI103, consistent with the tumor inhibition result (data not shown).

Figure 9A:
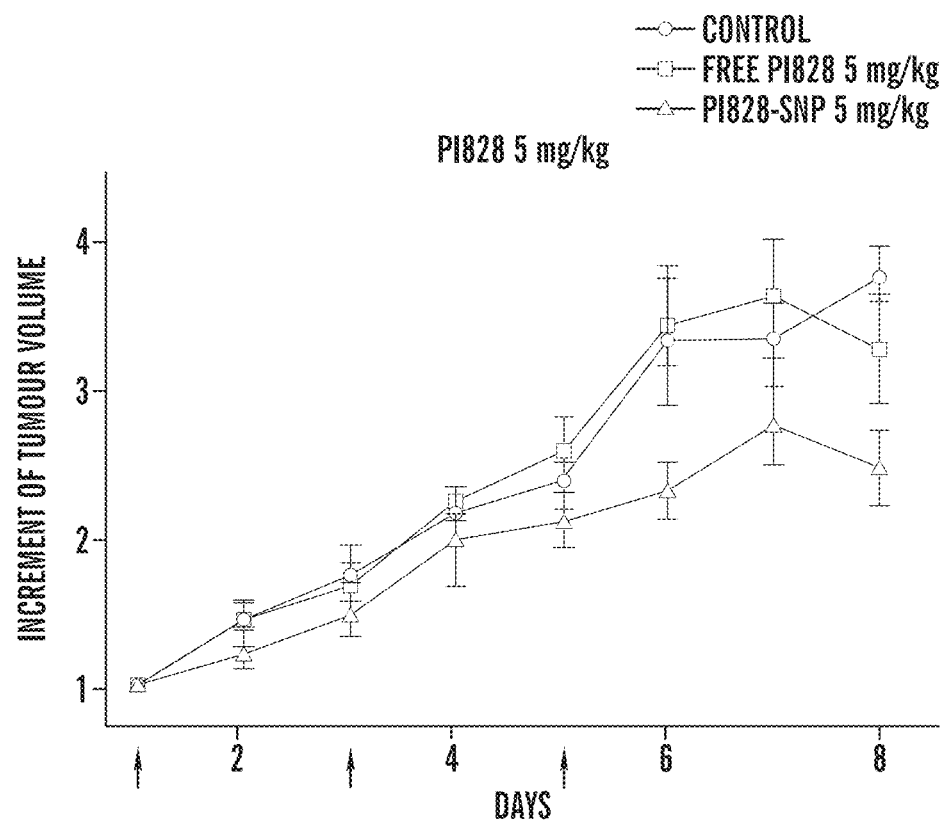
FIGS. 9A-9B (FIG. 9A) In vivo efficacy of PI828-SNPs in 4T1 breast cancer BALB/c mice bearing 8 day old subcutaneous tumors. Each animal wAS injected with three doses of either PBS (for control group), 5 mg/kg of free PI828, 5 mg/kg of PI828-SNP at same dose on each alternate days. Tumor volumes were measured every day for 8 days. End point for each animal was tumor size >2000 cm3 or tumor ulceration or necrosis or animal death.
Figure 9B:
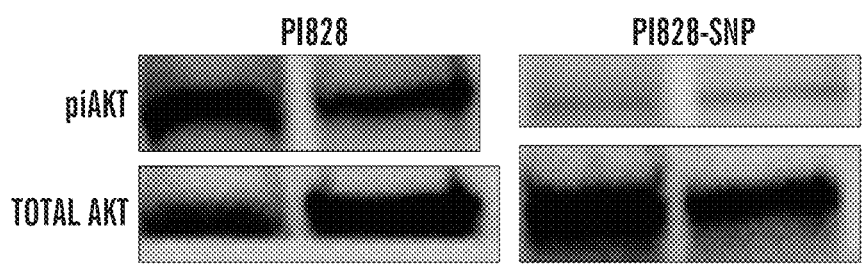

Treatment with PI828-SNPs (5 mg/kg PI828 equivalent, 3 doses) also exerted a superior inhibitory effect on Akt phosphorylation in vivo as compared to free PI828, translating into greater tumor growth inhibition (FIGS. 9A-9B). However, at this dose, the antitumor efficacy was significantly lower than that achieved with the PI103-SNPs. One explanation is that PI828, which is an analogue of LY294002, inhibits PI3K in the micromolar range, whereas PI103 is more potent. However, given that the both PI103-SNPs and PI828-SNPs inhibited PI3K signaling, it is likely that the release kinetics of the active agent plays a critical role in efficacy and needs to be considered in the design of supramolecular nanoparticles.

Effect of PI-103-SNP on Insulin Tolerance:

PI3K plays a central role in mediating insulin signaling that is conserved throughout eukaryotic evolution. While both the p110☐ and p110α isoforms have been implicated in insulin signaling, it is the former that is predominant in maintaining glucose homeostasis (10). We therefore investigated the effect of PI103-SNPs on insulin tolerance in a 4T1 breast cancer model. Consistent with previous studies (12,20), mice injected with free PI-103 exhibited only a minor decrease in blood glucose level after insulin injections. In contrast a significant drop in blood glucose level was observed when insulin was injected in mice pre-treated with PI103-SNP, or with empty nanoparticles as a control.

Figure 4A:
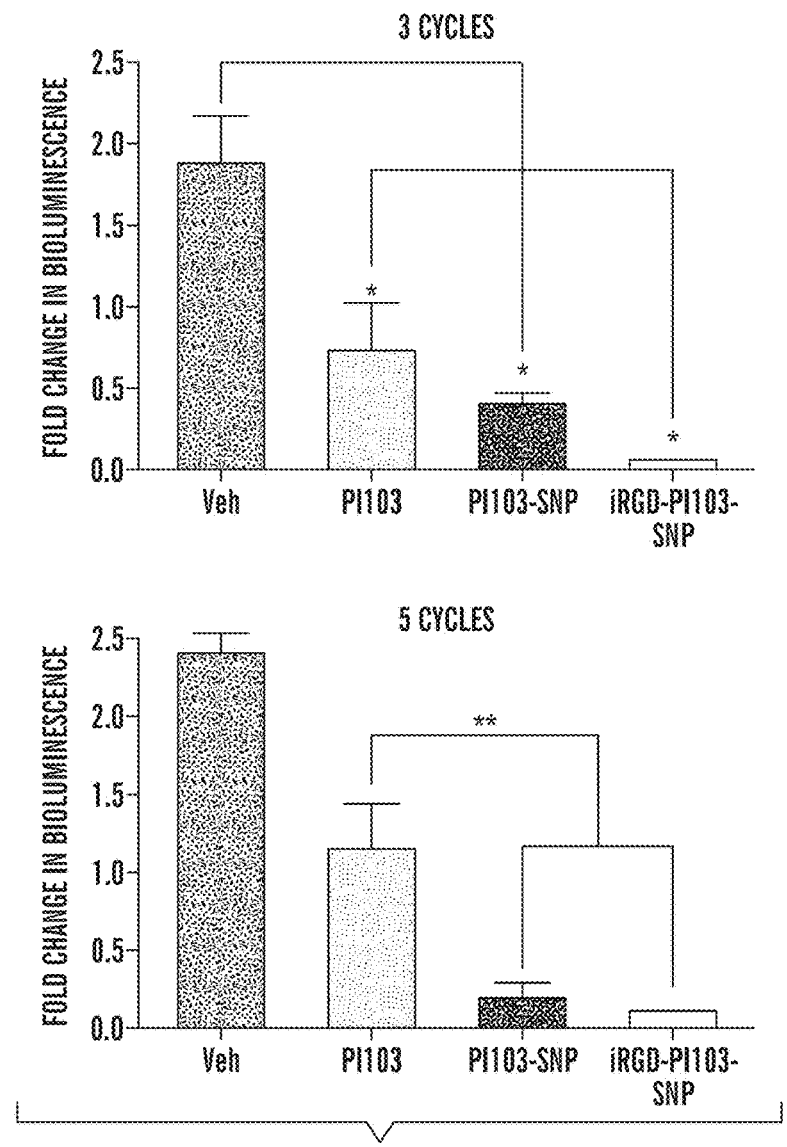
FIGS. 4A-4D demonstrate that PI103-SNP inhibits tumor growth in a K-ras$^{LSL/+}$/Pten$^{fl/fl}$ ovarian cancer model.
Figure 4B:
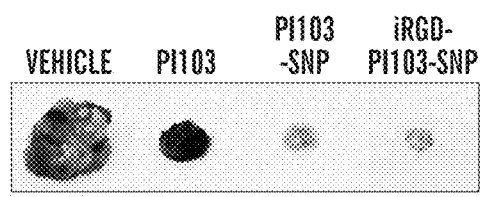
Figure 4C:
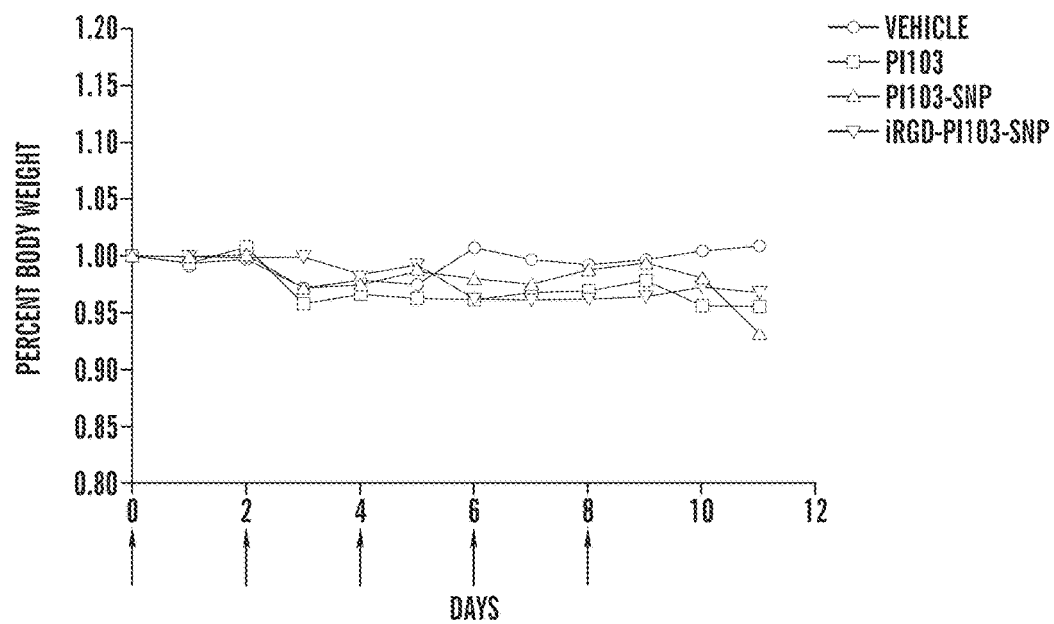
Figure 4D:
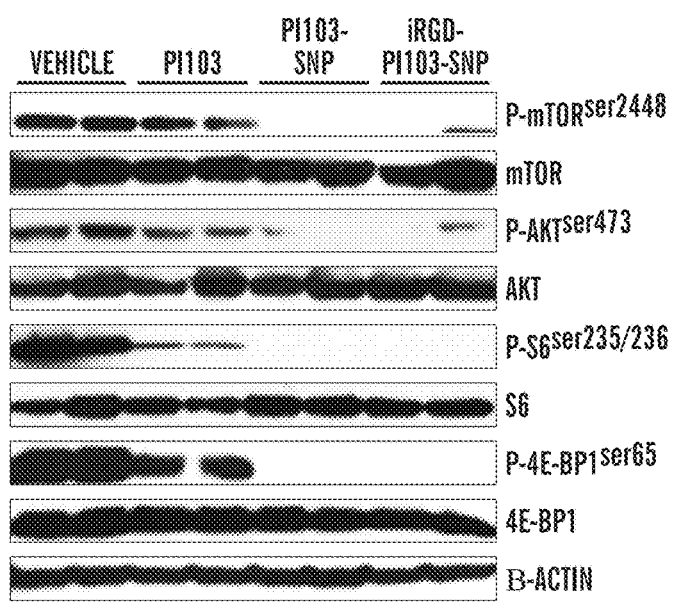

Efficacy of PI103-SNPs in an In Vivo K-Ras$^{LSL/+}$/Pten$^{fl/fl}$ Ovarian Cancer Model:

We also evaluated the effect of PI-103-SNP in a K-Ras$^{LSL/+}$/Pten$^{fl/fl}$ ovarian cancer model (26). We selected this model because tumors that lack Pten have been reported to be addicted to PI3K signaling (7). On the other hand, tumors that present a mutated or activated Ras have been reported to be less responsive to PI3K inhibitors (7). As shown in FIG. 4A, bioluminescence quantification of tumor luciferase signal indicates that the 3 doses of free PI103, PI-103-SNP and iRGD-PI103-SNP resulted in significant tumor regression as compared to vehicle control. The bioluminescence response of iRGD-PI-103-SNP was statistically significantly higher than free PI-103 after 3 cycles of treatments as compared with 5 cycles of treatment, consistent with previous observations that iRGD facilitates intra-tumoral penetrance and accumulation. No change in body weight was observed in any treatment group (FIG. 4C). The expression levels of PI3K/mTOR pathway markers, as assessed by western blot analysis of tumor samples from different groups, showed significant inhibition of activation of phospho-mTOR, phospho-AKT, phospho-S6 and phospho-4EBP1 in PI-103 nanoparticle and iRGD-coated PI103 nanoparticle groups as compared to the free PI-103 (FIG. 4D).

Supramolecular nanochemistry, the development of complex chemical nanostructures from molecular building blocks that interact via non-covalent intermolecular forces, is an emerging concept in cancer theranostics. Indeed, in a recent study, gandolinium (111)-encapsulated supramolecular nanoparticles were used in diagnosis of cancer metastasis (27). Similarly, we demonstrated that the use of structure activity relationships can facilitate the assembly of platinum cytotoxics into supramolecular nanostructures with resultant increase in antitumor efficacy and reduction in nephrotoxicity (16). Here we demonstrate that supramolecular nanochemistry can be extended to molecularly targeted therapeutics facilitating efficient inhibition of the PI3K signaling pathway.

While the use of nanotechnology to preferentially target anticancer agents to solid tumors is increasingly being explored, the traditional processes for synthesis of nanopharmaceuticals are often incompatible with the physico-chemical properties of many chemotherapeutic agents, which limits the entrapment efficiency or introduces suboptimal release kinetics. Indeed, in our current study, we observed that the attempts at encapsulating PI103 resulted in suboptimal loading or formation of unstable nanoparticles. Such challenges have limited the number of nanomedicines that have translated to the clinic despite the advantages of nanotechnology. In contrast, the higher incorporation efficiencies into the SNPs along with the observed stability indicate that the SNPs can facilitate clinical translation.

The clinical translation of PI3K inhibitors has been a challenge (28). A key difficulty is biomarker selection, with most studies relying on the phosphorylation status of Akt (29). Consistent with these studies, we observed that the SNP treatment in the ovarian cancer model resulted in significantly greater inhibition of phosphorylation of Akt, and of the downstream signaling molecules mTOR, S6 and 4E-BP1, as compared with free PI103. Interestingly, in the breast tumors, which were excised at a later time point post-treatment than the ovarian cancers, we observed that the phospho-Akt levels were similar in the SNP and free drug groups. However, the phosphorylation status of mTOR and S6 kinase, was significantly inhibited following treatment with the SNPs, and correlated well with the increased anti-tumor efficacy compared with the free drug. These results suggest that the downstream signals might be superior biomarkers of PI3K inhibitor efficacy than the upstream Akt. It is likely that this distinction between the predictive ability of the biomarkers is being dissected due to the temporality of inhibition arising from sustained release of the active agent from the supramolecular nanoparticles as compared with an binary ion' state of inhibition achieved by a therapeutic concentration of PI103 that can switch 'off' as soon as the drug is rapidly removed (12).

The sustained inhibition of the PI3K signaling achieved using the supramolecular nanoparticles can potentially overcome another challenge facing clinical translation of PI3K inhibitors. As seen in the current study, an acute exposure to the free drug (PI103) resulted in an increase in the phospho-Akt levels at later time-points. Such a rebound activation of the pathway is consistent with previous reports (28, 30), and has been reported to arise from a homeostatic feedback loop via an upregulation of receptor tyrosine kinases. Similarly, inhibition of mTORC1 can relieve a negative loop from S6K to IRS 1, leading to the activation of IGFR1 and PI3K-Akt (31). Interestingly, treatment with the PI103-SNPs could potentially overcome this feedback loop as evident from a sustained inhibition of the phospho-Akt signal. The reason may be that the intracellular concentration of PI103 achieved with SNPs is higher than when the cells are exposed to the free drug. Indeed, in a recent commentary, Engleman et al. have posed the question whether lack of efficacy of PI3K inhibitors is due to inadequate inhibition of the target or because complete inhibition of the target is not sufficient to produce antitumor activity (31) The current results indicate that in addition to the level of inhibition of the pathway, the temporality in terms of sustained release and target inhibition may be a critical element in determining antitumor outcome. Interestingly, a similar observation was made during the evolution of current clinical candidate GDC-0941 from PI103, where ~90% inhibition of Akt phosphorylation for several hours was seen as a requirement for antitumor activity, establishing a link between pharmacokinetic exposure and pharmacodynamic biomarker changes (9).

The ability of nanoparticles to passively accumulate in tumors coupled with the increased intracellular concentrations of the free drug achieved in this study permits increased intra-tumoral apoptosis. We also demonstrate that the efficacy is further improved by placing active targeting moieties such as iRGD peptides on the nanoparticle surface. Second, the sustained release, resulting in prolonged inhibition of the PI3K pathway and absence of the 'feedback loop' raises an interesting possibility that the duration of inhibition could be a critical determinant in clinical success in addition to drug concentration. Interestingly, the current results also highlight that while conventional tools can facilitate dissection of biological interactions on a spatial or concentration axes, the use of nanochemistry can potentially enable dissection on a temporal axis. Third, the absence of insulin resistance with the PI103-SNP, a class effect associated with p110a inhibitors including PI103, indicates that the supramolecular nanochemistry can significantly impact the therapeutic index. Additionally, rational optimization of the chemical structures to facilitate supramolecular assembly can overcome existing limitations associated with parent molecules such as PI103, thereby opening up the possibility of resuscitating promising drug candidates that had failed to translate into the clinic, thereby rejuvenating the diminishing drug pipelines.

Materials and Methods

Synthesis and Characterization of SNPs:

For PI103-SNP or PI828-SNP synthesis, L-a-phosphatidylcholine, drug-cholesterol conjugate and DSPE-PEG (at optimized weight ratios) were dissolved in 1.0 mL DCM. For the PI103-encapsulated nanoparticles, L-a-phosphatidylcholine, cholesterol, DSPE-PEG and PI103 were taken in different weight ratios, and while PI103 was dissolved in methanol; cholesterol, DSPE-PEG and phosphatidylcholine were dissolved in dry DCM. Resulting solutions were evaporated in a round-bottomed flask with the help of a rotary evaporator and thoroughly dried. The resulting thin films were hydrated with PBS with constant rotation at 55° C. for 2 h.

Nanoparticles were eluted through a Sephadex column followed by extrusion by a hand-held mini extruder (filter size 200 nm). The size was checked by DLS and drug loading was determined by UV-VIS spectroscopy. For release kinetics studies, drug-loaded nanoparticles (1 mg drug/ml, 5 ml) were suspended in PBS buffer (pH 7.4), 4T1 cell lysate or 4306 cell lysate in a float-a-lyzer dialysis tube (MWCO=3500 Dalton, Spectrum Lab). The dialysis tube was suspended in 1 L PBS pH 7.4 with gentle stirring to simulate the infinite sink tank condition. A 100 □L portion of the aliquot was collected from the sample at predetermined time intervals and replaced by equal volume of PBS buffer, and the released drug was quantified by UV-MS Spectrophotometer.

Cell Viability Assay:

4T1 and MDA MB 468 breast cancer cells were cultured in RPMI, 4306 ovarian cancer cells were cultured in DMEM, supplemented with 10% FBS and 1% of Antibiotic-Antimycotic 100× solution. $4 \times 10^3$ Cells were seeded into 96-well flat-bottomed plates. Free drug or drug loaded nanoparticles (normalized to equivalent amounts of free drug) were added in triplicate in each 96-well plate and then plates were incubated in 5% $CO^2$ atmosphere at 37° C. After desired time period of incubation, cells were washed and incubated with 100 µL phenol-red free medium (without FBS) containing 20 µl of the CellTiter 96 Aqueous One Solution reagents (PROMEGA, WI). After 2 hours incubation, the absorbance in each well was recorded.

PI103-SNPs Internalization Assay:

4T1 breast cancer cells ($1 \times 10^6$ cells) were seeded in 10 ml petri dish and incubated with free PI103 or equivalent amount of PI103-SNPs. After 4 hours incubation in 5% $CO_2$ atmosphere at 37° C., cells were washed thrice with PBS and replenished with fresh media. After desired time of incubation, $2 \times 10^8$ cells were lysed from each sample, centrifuges and supernatant was collected. Amount of drug in the samples were measured by UV-Vis spectroscopy using drug free cells as control.

Western Blot Assay:

For western blot, $5 \times 10^4$ Cells were seeded in each well of a 6 well plate and incubated with free drug or equivalent amount of drug loaded nanoparticles in appropriate concentration for 24 hours followed by washing ice cold PBS. The protein was collected and protein lysates were electrophoresed. Then membranes were incubated with Phospho AKT, total AKT and actin antibodies overnight at 4° C. After appropriate amount of washing with TBST, membranes were incubated with horseradish peroxidase-conjugated secondary antibody for 1 hour. Detection was done using G-box (Syngene) and densitometric quantification was done by image J software.

Efficacy Study of SNPs in Murine 4T1 Breast Cancer Model:

4T1 breast cancer cells ($1 \times 10^8$) were implanted subcutaneously in the flanks of 4-week-old BALB/c mice. The drug therapy was started on day 9. The drug therapy consisted of administration of PBS (for Control group), free drug (5 mg/kg) and SNPs (5 mg/kg). For PI103-SNPs, the drug therapy also consisted iRGD-PI103-SNPs group (5 mg/kg). The tumor volumes and body weights were monitored on every alternate day for 11 days. The tumor volume was calculated by using the formula, $L \times B^2/2$ and tumor volume increments were calculated as $V_t/V_0$ ($V_0$ was tumor volume at the time of first injection). All animal procedures were approved by the Harvard Institutional Use and Care of Animals Committee.

Insulin Tolerance Test Using PI103-SNPs:

Random fed mice (murine 4T1 breast cancer model) were injected with a single dose of Empty nanoparticles (Control), Free PI-103 (5 mg/kg) and PI103-SNPs via tail vain injections. Freshly prepared Insulin solution (0.75 U/Kg) in 0.1 ml 0.9% NaCl was injected intraperitoneally to mice 1 hour after the drug administration. The blood glucose levels were measured before and 45 min after the insulin injections using glucometer.

Efficacy Study of PI103-SNPs in Murine Ovarian Cancer Tumor Model:

Ovarian adenocarcinomas were induced in genetically engineered K-Ras$^{LSL/+}$/Pten$^{fl/fl}$ mice via intrabursal delivery of adenovirus-carrying Cre recombinase. Tumor cells were also engineered to express luciferase once activated by Adeno-Cre to make tumor imaging possible before and after drug treatment. Once mice developed medium to large tumors, they were placed into one of four treatment groups (vehicle, Free-PI-103 5 mg/kg, PI-103-SNP 5 mg/kg, and iRGD-PI103-SNP 5 mg/kg) and all drugs were administered via tail vein injection. Tumor imaging in vivo was performed using an IVIS Lumina II Imaging System. Quantification of bioluminescence was achieved by using Living Image Software 3.1 (Caliper Life Sciences). Images were taken a day prior to initial treatment (day 0, baseline image), after 3 treatments, and 1 d after 5 treatments.

Western Blot Assay of In Vivo Tumor Samples:

For animal tissue, tumor stored in −80° C. were pulverized in a mortar and pestle using liquid nitrogen, then treated with RIPA buffer to extract the protein. Amount of protein was measured by BCA assay and equal amount of protein lysates were electrophoresed on a polyacrylamide gel, then transferred to polyvinylidene difluoride membrane, (BIO-RAD) and blocked in with 5% milk solution. Then membranes were incubated with appropriate concentration of primary antibody overnight at 4° C., followed by horseradish peroxidase-conjugated secondary antibody for 1 hour. Detection was done using G-box from SYNGENE and densitometric quantification was done by IMAGE-J software.

Tumor Slice Staining and Imaging:

For IHC and TUNEL study, tumor slices (5 Am) were cut after frozen in OCT medium at Harvard Medical School Core facility. For iRGD targeting images these sections were directly imaged under the green filter of Nikon TE2000 microscope. For TUNEL imaging studies, tumor sections were stained with standard TMR red fluorescent terminal deoxynucleotidyl tranferase-mediated dUTP nick end labeling (TUNEL) kit following the manufacturer's protocol (In Situ Cell Death Detection Kit, TMR-Red, Roche). Images were obtained using a Nikon Eclipse TE2000 fluorescence microscope equipped with red filter. Significant internalization of FAM-1RGD tagged PI103-cholesterol was imaged. Blood vessels were stained with vWF staining kit.

Statistics:

The statistical analysis was determined by two-tailed student's t-test and one-way ANOVA followed by Newman Keuls Post Hoc test. $p<0.05$ was considered to indicate significant differences.

Supplemental Materials and Methods:

All chemical reagents were of analytical grade, used as supplied without further purification unless indicated. All reactions were performed under inert conditions unless otherwise indicated.

Dichloromethane (DCM), anhydrous DCM, Methanol, Cholesterol, Dimethylamino Pyridine (DMAP), Succinic Anhydride, Sodium Sulfate, Pyridine, 1-Ethyl-3-(3-dimethylaminopropyl)carbodiimide (EDC), L-a-phosphatidylcholine and Sephadex G-25 were purchased from SIGMA-ALDRICH. PI-103 was purchased from SELLECKCHEM. 1,2-Distearoyl-sn-Glycero-3-Phosphoethanolamine-N4Amino(Polythylene Glycol) 2000] and the mini handheld Extruder kit (including 0.2 pm Whatman Nucleopore Track-Etch Membrane, Whatman filter supports and 1.0 mL Hamiltonian syringes) were bought from AVANTI POLAR LIPIDS INC. Analytical thin-layer chromatography (TLC) was performed using precoated silica gel Aluminium sheets 60 F254 bought from EMD LABORATORIES. Spots on the TLC plates were visualized under UV light, and/or by treatment with alkaline permanganate solution followed by heating. MTS reagent was supplied by PROMEGA. Column chromatography was conducted using silica gel (230-400 mesh) from QUALIGENS. $^1H$ and $^{13}C$ NMR spectra were recorded on Bruker DPX 400 MHz spectrometer. Chemical shifts are reported in 6 (ppm) units using $^{13}C$ and residual $^1H$ signals from deuterated solvents as references. Spectra were analyzed with Mest-Re-C Lite (Mestrelab Research) and/or XWinPlot (Bruker Biospin). Electrospray ionization mass spectra were recorded on a Micromass Q Tof 2 (WATERS) and data were analyzed with MASSLYNX 4.0 (WATERS) software.

Synthesis of PI103-Cholesterol Conjugate:

Cholesterol (500 mg, 1.29 mmol) was dissolved in 5 ml of anhydrous pyridine. Succinic anhydride (645 mg, 6.45 mmol) and catalytic amount of DMAP was added to the reaction mixture to form clear solution. The reaction mixture was flushed with argon and allowed to stir under argon atmosphere for 12 h. Then, pyridine was removed under vacuum and the crude residue was diluted in 30 ml DCM. It was washed with 1N HCl (30 ml) and water (30 ml). The organic layer was separated and dried over anhydrous sodium sulfate, filtered and concentrated in vacuo. Completion of the reaction was confirmed by performing a TLC in 1:99 Methanol:DCM solvent mixture. The product was used for next step without further purification. PI-103 (25 mg, 0.072 mmol) was dissolved in 3 ml anhydrous DCM followed by addition of cholesterol-succinic acid (0.216 mmol, 105 mg), EDC (0.216 mmol, 41.4 mg) and DMAP (0.216, 26 mg). The reaction mixture was stirred at room temperature for 12 h under argon. Upon completion of reaction as monitored by TLC, the reaction mixture was diluted with 10 ml DCM and washed with dilute HCl and water. The organic layers were separated, combined and dried over anhydrous sodium sulfate. The solvent was evaporated under vacuum and the crude product was purified by using column chromatography, eluting with methanol:methylene chloride gradient, to give the PI-103 cholesterol conjugate as a light yellow solid (52 mg, 90%). $^1H$ NMR (CDCl$_3$, 400 MHz): □ 8.65-8.53 (m, 1H), 8.36 (d, J 8.3 Hz, 1H), 8.19 (d, J=1.7 Hz, 1H), 7.56-7.41 (m, 1H), 5.29 (s, 1H), 4.28-4.15 (m, 2H), 3.97-3.86 (m, 2H), 3.64 (s, 1H), 2.93 (d, J=7.0 Hz, 1H), 2.76 (d, J=7.0 Hz, 1H), 2.35 (s, 1H), 2.17 (s, 1H), 1.59 (s, 4H), 1.29 (d, J=34.2 Hz, 3H), 1.25-1.23 (m, 6H), 1.13-0.80 (m, 13H), 0.66 (s, 2H), 0.03 (m, 12H). HRMS Calculated for [C501-164N406+H]+:817.4899 Found: 817.4883.

Synthesis of PI-828-Cholesterol Conjugate:

20.0 mg (0.044 mmol) of cholesteryl chloroformate was dissolved in 2.0 mL dry DCM. To it 28 mg (0.088 mmol) of PI-828 dissolved in 2.0 mL of dry DCM was added. Finally 15.5 □L (0.088 mmol) of dry DIPEA was added to it dropwise at room temperature in an inert condition. Progress of the reaction was monitored by thin layer chromatography. After 24 h, it was quenched with 100 mL 0.1(N) HCl and the compound was extracted in DCM. The desired product was separated by column chromatography using a solvent gradient of (0-5)% MeOH in DCM. iHNMR (300 MHz) 8 (ppm)=8.165-8.13 (m); 7.59-7.40 (m, aromatic); 6.72 (s); 5.98-5.93 (m); 5.42-5.40 (m); 4.67-4.59 (m); 3.75-3.74 (m); 3.44-3.40 (m); 2.43-2.34 (m); 2.04-1.93 (m); 1.86-1.77 (m); 1.65-1.43 (m); 1.35-1.43 (m); 1.32-0.85 (m).

Preparation of PI3K-Inhibiting NPs:

PI103-SNP:

3.5 mg (50 mol %) of L-a-phosphatidylcholine, 2.5 mg (20 mol %) PI103-cholesterol conjugate and 7.5 mg (30 mol %) of 1,2-Distearoyl-sn-Glycero-3-Phosphoethanolamine-N4Amino(Polythylene Glycol) 2000](DSPE-PEG) were dissolved in 1.0 mL DCM. Solvent was evaporated into a thin and uniform lipid-drug film using a rotary evaporator. The lipid-drug film was then hydrated with 1.0 mL H$_2$O for 1 h at 55° C. The hydrated nanoparticles looked light yellow to white with little viscous texture. It was passed though Sephadex G-25 column and extruded at 55° C. to obtain sub 200 nm particles. A standard curve of PI103-Cholesterol conjugate in DMF was generated by measuring absorbance at 285 nm using UV-Vis spectrophotometry (SHIMADZU 2450). A known concentration of nanoparticle was dissolved in DMF and the absorbance value at 285 nm was used to calculate the loading from standard curve. This was validated using HPLC method. The iRGD tagged PI103 nanoparticles were synthesized by the same procedure but iRGD peptide was conjugated to DSPE-PEG-maleimide using thiol conjugation as described by Prof. Ruoslahti.

PI828-SNP:

PI-828 conjugated cholesteryl chloroformate, phosphatidylcholine and DSPE-PEG (in 5:10:1 weight ratio) were dissolved in DCM. The resulting solution evaporated in a round-bottomed flask with the help of a rotary evaporator and thoroughly dried. The resulting thin film was hydrated with PBS with constant rotation at 70° C. for 2 h. Nanoparticles were eluted through a Sephadex column followed by extrusion by a hand-held mini extruder (filter size 200 nm). The size was checked by DLS and drug loading was determined by UV-VIS spectroscopy.

PI103-Encapsulated NP:

Phosphatidylcholine, Cholesterol, DSPE-PEG and PI103 were taken in 10:5:1:1 weight ratio. PI103 was soluble in Methanol and Cholesterol, DSPE-PEG and Phosphatidylcholine were soluble in dry DCM. The solution was taken in a round-bottomed flask and evaporated using a rotary evaporator. The thin film was dried thoroughly and was hydrated by 1.0 mL of ddH$_2$O. It was stirred at the highest possible speed in rotary evaporator @ 55° C. The white colored suspension was passed through Sephadex G-25 column. The eluent was extruded with the help of a hand-held mini extruder (AVANTI) using 200 nm polycarbonate filter membranes. Drug loading was performed by UV spectrophotometer.

Release Kinetics Studies:

Drug loaded nanoparticles (1 mg drug/ml, 5 ml) were suspended in PBS buffer (pH 7.4), 4T1 cell lysate and 4306 cell lysate (additionally for PI828-SNPs) and sealed in a dialysis tube (MWCO=3500 Dalton, Spectrum Lab). The dialysis tube was suspended in 1 L PBS ph7.4 pH with gentle stirring to simulate the infinite sink tank condition. A 100 pL portion of the aliquot was collected from the incubation medium at predetermined time intervals and replaced by equal volume of PBS buffer, and the released drug was quantified by UV-VIS Spectrophotometer and plotted as cumulative drug release.

Nanoparticle Characterization and Stability Studies:

The mean particle size of the nanoparticles was measured by Dynamic Light Scattering method using Zetasizer Nano ZS90 (Malvern, UK). 10 pL of nanoparticles solution was diluted to 1 ml using DI water and 3 sets of 10 measurements each were performed at 90 degree scattering angle to get the average particle size. The zeta potential was measured using a Zetasizer ZS90 with the nanoparticles diluted in water for measurement according to the manufacturer's manual. The physical stability of nanoparticles was evaluated by measuring changes in mean particle size and zeta potential during storage condition at 4° C.

Cryo-Transmission Electron Microscopy for PI103-SNPs:

The sample was preserved in vitrified ice supported by holey carbon films on 400 mesh copper grids. The sample was prepared by applying 3 pL of sample suspension to a cleaned grid, blotting away with filter paper and immediately proceeding with vitrification in liquid ethane. Grids were stored under liquid nitrogen until transferred to the electron microscope for imaging. Electron microscopy was performed using an FEI Tecnai Cryo-Bio 200 KV FEG TEM, operating at 120 KeV equipped with 2 Gatan Sirius CCD cameras one 2K*2K and one 4K*4K pixel. Vitreous ice grids were transferred into the electron microscope using a cryostage that maintains the grids at a temperature below −170° C. Images of the grid were acquired at multiple scales to assess the overall distribution of the specimen. After identifying potentially suitable target areas for imaging at lower magnification, high magnification images were acquired at nominal magnification of 52,000× (0.21 nm/pixel), and 21,000× (0.50 nm/pixel). Images were acquired at a nominal underfocus of −5 pm (21,000×) and −4 pm (52,000×) at electron doses of −10-15 e/A° 2.

Cell Viability Assay:

4T1 and MDA MB 468 breast cancer cells were cultured in RPMI, 4306 ovarian cancer cells were cultured in DMEM, supplemented with 10% FBS and 1% of Antibiotic-Antimycotic 100× solution (Invitrogen, 15240-062). 4×10$^3$ Cells were seeded into 96-well flat-bottomed plates. Free drug or drug loaded nanoparticles (normalized to equivalent amounts of free drug) was added in triplicate in each 96-well plate at appropriate concentrations (1, 10, 100 nM and 1, 10, and 50 pM) and then plates were incubated in 5% CO2 atmosphere at 37° C. After desired time period of incubation, cells were washed and incubated with 100 pl phenol-red free medium (without FBS) containing 20 pl of the CellTiter 96 Aqueous One Solution reagents (Promega, WI). After 2 hours incubation in a 5% CO2 atmosphere at 37° C., the absorbance in each well was recorded at 490 nm using an Epoch plate reader (Biotek instruments, VT). The absorbance reflects the number of surviving cells. Blanks were subtracted from all data and results analyzed using Graph-Pad Prism™ software (GraphPad, San Diego, Calif.). Each experiment was independently repeated thrice and data shown is mean±SE of n=3.

PI103-SNPs Internalization Assay:

4T1 breast cancer cells (1×10$^6$ cells) were seeded in 10 ml petri dish and incubated with serum free media for 6 hours after it reached 70% confluency. Then, free PI103 or equivalent amount of PI103-SNPs was added in 20 pM concentration in serum deprived media (1% FBS). After 4 hours incubation in 5% CO2 atmosphere at 37° C., cells were washed thrice with PBS and replenished with fresh media. After desired time of incubation, 2×10$^6$ cells were lysed from each sample, centrifuges and supernatant was collected. Amount of drug in the samples were measured by UV-Vis spectroscopy using drug free cells as control.

Western Blot Assay:

For western blot 5×10$^4$ Cells were seeded in each well of a 6 well plate. When cells were 70% confluent, they were incubated in serum free media for 6 hours. Then, free drug or equivalent amount of drug loaded nanoparticles were added in appropriate concentration in serum deprived media (1% FBS). After 24 hours of incubation in 5% CO2 atmosphere at 37° C., cells were washed twice with ice cold PBS and protein was collected by scraping using RIPA buffer supplemented with protease inhibitor (Roche diagnostic). Amount of protein was measured by RCA assay and equal amount of protein lysates were electrophoresed on a 4-20% polyacrylamide gel, transferred to polyvinylidene difluoride membrane, and blocked in TBST-T with 5% dry milk. Then membranes were incubated in TBST with Phospho AKT (S473) (1:500 dilution), total AKT (1:1000 dilution), and actin (1:2000 dilution) antibodies (all antibodies from Cell Signalling Technology) overnight at 4° C. After appropriate amount of washing with TBST, membranes were incubated with horseradish peroxidase-conjugated secondary antibody for 1 hour. Detection was done using G-Box™ from Syngene and densitometric quantification was done by image J™ software.

Efficacy Study of PI828-SNPs and PI103-SNPs in Murine 4T1 Breast Cancer Model:

4T1 breast cancer cells (1×10$^5$) were implanted subcutaneously in the flanks of 4-week-old BALB/c mice (weighing 20 g, Charles River Laboratories). The drug therapy was started on day 9. For PI828-SNPs, the drug therapy consisted of administration of PBS (for Control group), free PI-828 (5 mg/kg) and PI828-SNPs (5 mg/kg). For PI103-SNPs, the drug therapy consisted of administration of PBS (for control group), free PI-103 (5 mg/kg) and PI103-SNPs (5 mg/kg) and 1RGD-PI103-SNPs (5 mg/kg) (administered by tail-vain injection). The tumor volumes and body weights were monitored on every alternate day for 11 days. The tumor volume was calculated by using the formula, L×B2/2, where the longest diameter was considered as L and the shortest diameter as measured using a vernier caliper as B. Tumor volume increments were calculated as VtlV0 (V0 was tumor volume at the time of first injection). The animals were sacrificed when the average tumor volume of the control exceeded 2000 mm3 in the control group. The tumors were harvested immediately following sacrifice and stored in 10% formalin for further analysis.

Western Blot Assay of In Vivo Tumor Samples:

For animal tissue, tumor stored in −80° C. were pulverized in a mortar and pestle using liquid nitrogen, then treated with RIPA buffer to extract the protein. Amount of protein was measured by BCA assay and equal amount of protein lysates were electrophoresed on a polyacrylamide gel, then transferred to polyvinylidene difluoride membrane, (Bic-Rad) and blocked in with 5% milk scullion. Then membranes were incubated with appropriate concentration of primary antibody (all antibodies from Cell Signalling Technology) overnight at 4° C., followed by horseradish peroxidase-conjugated secondary antibody for 1 hour. Detection was done using G-box from Syngene and densitometric quantification was done by image J™ software.

Insulin Tolerance Test Using PI103-SNPs:

Random fed mice (murine 4T1 breast cancer model) were injected with a single dose of Empty nanoparticles (Control), Free PI-103 (5 mg/kg) and PI103-SNPs via tail vain injections. Freshly prepared Insulin solution (0.75 U/Kg) in 0.1 ml 0.9% NaCl was injected intraperitoneally to mice 1 hour after the drug administration. The blood glucose levels were measured before and 45 min after the insulin injections using glucometer.

Efficacy Study of PI103-SNPs in Murine Ovarian Cancer Tumor Model:

Ovarian adenocarcinomas were induced in genetically engineered K-ras isu+/Pten mice via intrabursal delivery of adenovirus-carrying Cre recombinase. Tumor cells were also engineered to express luciferase once activated by Adeno-Cre to make tumor imaging possible before and after drug treatment. Once mice developed medium to large tumors, they were placed into one of four treatment groups (vehicle, Free-PI-103 5 mg/kg, PI-103-SNP 5 mg/kg, and iRGD-PI103-SNP 5 mg/kg) and all drugs were administered via tail vein injection. Treatment was administered five times over a 10 d period with a 1 d period between treatments for Free-PI-103 and PI103-SNP, while iRGD-PI103-SNP was administered three times over a 7 d period with 1 d break between treatments. Tumor imaging in vivo was performed using an 1VIS Lumina II™ Imaging System. Quantification of bioluminescence was achieved by using Living Image Software 3.1™ (Caliper Life Sciences). Prior to imaging, mice received 150 mg/kg of D-luciferin firefly potassium salt via intraperitoneal injection. Five minutes post-luciferin injection, mice were anesthetized in a 2.5% isoflurane induction chamber where they were kept under anesthesia by a manifold supplying isoflurane and their body temperature was maintained steady by a 37° C. temperature stage. Bioluminescent signal was collected 15 min after luciferin administration for an exposure time of 30 s. Images were taken a day prior to initial treatment (day 0, baseline image), after 3 treatments, and 1 d after 5 treatments.

Western Blot Analysis of In Vivo Tumor Samples:

Treatment efficacy was quantified by examining expression of PI3KImTOR proteins following treatment cycle via western blot analysis. Tissue lysates were examined on a 4-20% Tris Glycine gel (Invitrogen) and transferred to a 0.4 pM PVDF membrane (Perkins Elmer). Non-specific proteins were blocked with 5% nonfat dry milk. Primary antibodies (Cell Signaling Technologies, 1:1000 dilution) used with pAkt S473, pS6, pmTOR, p4E-BP1, Akt, S6, mTOR, and 4E-BPI were incubated overnight. B-Actin was used as a loading control. Anti-rabbit IgG secondary antibody (Cell Signaling Technologies, 1:2000) was then incubated at room temperature for 1 h. Expressed proteins were detected using Supersignal West Pico Chemiluminescence™ substrate (Thermo Scientific).

Tumor Slice Staining and Imaging:

For IHC and TUNEL study, tumor slices (5 Am) were cut after frozen in OCT medium at Harvard Medical School Core facility. For iRGD targeting images these sections were directly imaged under the green filter of Nikon TE2000™ microscope. For TUNEL imaging studies, tumor sections were stained with standard TMR red fluorescent terminal deoxynucleotidyl tranferase-mediated dUTP nick end labeling (TUNEL) kit following the manufacturer's protocol (In Situ Cell Death Detection Kit, TMR-Red, Roche). Images were obtained using a Nikon Eclipse TE2000™ fluorescence microscope equipped with red filter. Significant internalization of FAM-iRGD tagged PI103—cholesterol was imaged. Blood vessels were stained with vWF staining kit.

REFERENCES

1. World Health Organization (2008) WHO Cancer Report, Available at http://vvww.whointicancer/ent
2. Gschwind A, et al. (2004) The discovery of receptor tyrosine kinases: targets for cancer therapy. Nat Rev Cancer 4, 361-370.
3. Zhang J, et al. (2009) Targeting cancer with small molecule kinase inhibitors. Nat Rev Cancer 9, 28-39.
4. Ferrari M (2005) Cancer nanotechnology: Opportunities and challenges. Nat Rev Cancer 5:161-171.
5. Sengupta S, Sasisekharan R. (2007) Exploiting nanotechnology to target cancer. Br J Cancer 96: 1315-1319.
6. Engelman J A, Luo J, Cantley L C. (2006) The evolution of phosphatidylinositol 3-kinases as regulators of growth and metabolism. Nat Rev Genet. 7:606-19.
7. Engelman J A. (2009) Targeting PI3K signalling in cancer: opportunities, challenges and limitations. Nat Rev Cancer. 9:550-62.
8. Cantley L C, Neel B G (1999) New insights into tumor suppression: PTEN suppresses tumor formation by restraining the phosphoinositide 3-kinase/AKT pathway. Proc Natl Acad Sci USA. 96:4240-5.
9. Workman P, et al. (2010) Drugging the PI3 kinome: from chemical tools to drugs in the clinic. Cancer Res. 70:2146-57.
10. Knight Z A, et al. (2006) A pharmacological map of the PI3-K family defines a role for p110alpha in insulin signaling. Cell. 125(4):733-47.
11. Bendell J C, et al. (2012) Phase I, dose-escalation study of BKM120, an oral pan-Class 1 PI3K inhibitor, in patients with advanced solid tumors. J Clin Oncol; 30(3): 282-90.
12. Raynaud F I, et al. (2009) Biological properties of potent inhibitors of class I phosphatidylinositide 3-kinases: from PI-103 through PI-540, PI-620 to the oral agent GDC-0941. Mol Cancer Ther. 8(7):1725-38.

13. Yuan F, et al. (1994) Microvascular permeability and interstitial penetration of sterically stabilized (stealth) liposomes in a human tumor xenograft. Cancer Res 54:3352-3356.
14. Harfouche R, et al. (2009) Nanoparticle-mediated targeting of phosphatidylinositol-3-kinase signaling inhibits angiogenesis. Angiogenesis. 12: 325-38.
15. Karve S, et al (2012). Revival of the abandoned therapeutic wortmannin by nanoparticle drug delivery. Proc Nati Acad Sci USA. 109(21):8230-5.
16. Sengupta P, et al. (2012). Cholesterol-tethered platinum II-based supramolecular nanoparticle increases antitumor efficacy and reduces nephrotoxicity. Proc Nati Aced Sci USA. 109(28):11294-9.
17. Lehn J M (1995) Supramolecular Chemistry: Concepts and Perspectives (VCH, New York).
18. Lehn J M (2002) Toward complex matter: Supramolecular chemistry and self-organization. Proc Natl Acad Sol USA 99:4763-4768.
19. Gharbi S I, et al (2007) Exploring the specificity of the PI3K family inhibitor LY294002. Biochem J. 404(1):15-21.
20. Sengupta S, et at. (2005) Temporal targeting of tumour cells and neovasculature with a nanoscale delivery system. Nature 436:568-572.
21. Schipper M L, et al. (2009) Particle size, surface coating, and PEGylation influence the biodistribution of quantum dots in living mice. Small. 5(1):126-34.
22. Seavey M M, et al (2009). A novel human Her-2/neu chimeric molecule expressed by *Listeria monocytogenes* can elicit potent HLA-A2 restricted CD8-positive T cell responses and impact the growth and spread of Her-2/neu-positive breast tumors. Clin Cancer Res. 15(3):924-32.
23. Miller T W, et al. (2011) Mutations in the phosphatidylinositol 3-kinase pathway: role in tumor progression and therapeutic implications in breast cancer. Breast Cancer Res. 13(6):224.
24. Goldman J et al. (2012) Chemotherapy-induced Akt survival signaling is regulated by CD44-Ezrin/Radaxin Moesin (ERM) scaffolding, dependent on EGFR activity. Cancer Res. 72:27.
25. Sugahara K N, et al (2009) Tissue-penetrating delivery of compounds and nanoparticles into tumors. Cancer Cell. 16(6):510-20.
26. Dinulescu D M, et al. (2005) Role of K-ras and Pten in the development of mouse models of endometriosis and endometrioid ovarian cancer. Nat Med 11:63-70.
27. Chen K J, et al. (2011) A small MRI contrast agent library of gadolinium(III)-encapsulated supramolecular nanoparticles for improved relaxivity and sensitivity. Biomaterials 32:2160-2165.
28. Turke A B, Engelman J A. (2010) PIKing the right patient. Clin Cancer Res. 16(14):3523-5.
29. Clarke P A, Workman P. (2012) Phosphatidylinositide-3-kinase inhibitors: addressing questions of isoform selectivity and pharmacodynamic/predictive biomarkers in early clinical trials. J Clin Oncol. 30(3):331-3.
30. Muranen T, et al. (2012) Inhibition of PI3KImTOR leads to adaptive resistance in matrix-attached cancer cells. Cancer Cell. 21(2):227-39.
31. Courtney K D, et al (2010). The PI3K pathway as drug target in human cancer. J Clin Oncol. 28(6):1075-83.

Example 2: Cholesterol-Tethered Platinum II-Based Supramolecular Nanoparticle Increases Antitumor Efficacy and Reduces Nephrotoxicity Nanoscale drug delivery vehicles have been harnessed extensively as carriers for cancer chemotherapeutics. However, traditional pharmaceutical approaches for nanoformulation have been a challenge with molecules that exhibit incompatible physicochemical properties, such as platinum-based chemotherapeutics. Here we describe the rational design of active molecules that facilitate supramolecular assembly in the nanoscale dimension. Using cisplatin as a template, we describe the synthesis of a unique platinum (II) tethered to a cholesterol backbone via a unique monocarboxylato and O→Pt coordination environment that facilitates nanoparticle assembly with a fixed ratio of phosphatidylcholine and 1,2-distearoyl-sn-glycero-3-phosphoethanolamine-N-[amino (polyethylene glycol)-2000]. The nanoparticles formed exhibit lower IC50 values compared with carboplatin or cisplatin in vitro, and are active in cisplatin-resistant conditions. Additionally, the nanoparticles exhibit significantly enhanced in vivo antitumor efficacy in murine 4T1 breast cancer and in K-RasLSL/+/Ptenfl/fl ovarian cancer models with decreased systemic- and nephro-toxicity. The results described herein indicate that the integration of rational drug design and supramolecular nanochemistry is a powerful strategy for drug development.

Cancer remains one of the main causes of death in the United States and many western countries. In addition, the incidence is also increasing in less developed and economically transitioning countries (1). The World Health Organization projects over 12 million deaths worldwide in 2030 because of cancer, up from 7.6 million in 2008 (2). To address this growing problem, there is an urgent need to develop treatment strategies that are more efficacious with lesser adverse effects. An increasingly pursued approach to achieve these goals is the use of nanotechnology to preferentially target anticancer agents to solid tumors (3). This approach capitalizes on the unique leaky angiogenic tumor vasculature coupled with impaired intratumoral lymphatic drainage, contributing to an enhanced permeation and retention (EPR) effect (4). Indeed, nanoparticles carrying a doxorubicin payload or an albumin-paclitaxel nanocomplex increase intratumoral drug concentration (5, 6) and are currently in the clinics (7). However, traditional processes for nanoformulation are often incompatible with physicochemical properties of many chemotherapeutic agents, which limit the entrapment efficiency or introduce suboptimal release kinetics.

Described herein is a unique paradigm moving beyond traditional encapsulation strategies to the rational design of molecules that facilitate supramolecular assembly in the nanoscale dimension. In this study, cisplatin [cis-dichlorodiamineplatinum (II)] was as an example to demonstrate this approach. Cisplatin is one of the most widely used chemotherapeutic agents (8) but poses significant challenges for nanoformulations (9, 10). For example, SPI-077, a sterically stabilized liposome encapsulating cisplatin, exhibited poor clinical efficacy resulting from impaired drug release (11, 12).

To achieve supramolecular nanoassembly, we synthesized a cholesterol-tethered cisplatinum (II) amphiphile. The design of the tether was inspired by the process of "aquation," wherein the chloride leaving groups of cisplatin are rapidly displaced to form cis-Pt[(NH3)2(OH2)Cl]+ and cis-Pt[(NH3)2(OH2)2]2+(8). Self-assembling cholesterol-succinic acid-cisplatinum II-based nanoparticles (SACNs) exhibited increased potency and efficacy in vitro and in vivo, respectively. Additionally, the SACNs exceed the size cutoff for clearance by the kidney (13), and therefore exhibited limited cisplatin-associated nephrotoxicity (14). We demonstrate herein that rational drug design can enable the increase in the supramolecular dimension from the Angstrom- to the nano-scale, thereby conferring unique biological properties. Furthermore, only three platinates—cisplatin, carboplatin, and oxaliplatin—have been successfully used in the clinics (8). The increased efficacy with improved therapeutic index of the current molecule compared with the existing platinates indicates the potential for clinical translation as the next-generation platinum-based chemotherapeutic.

Synthesis of Cholesterol-Succinic Acid-Pt(II) Molecule.

Figure 14:
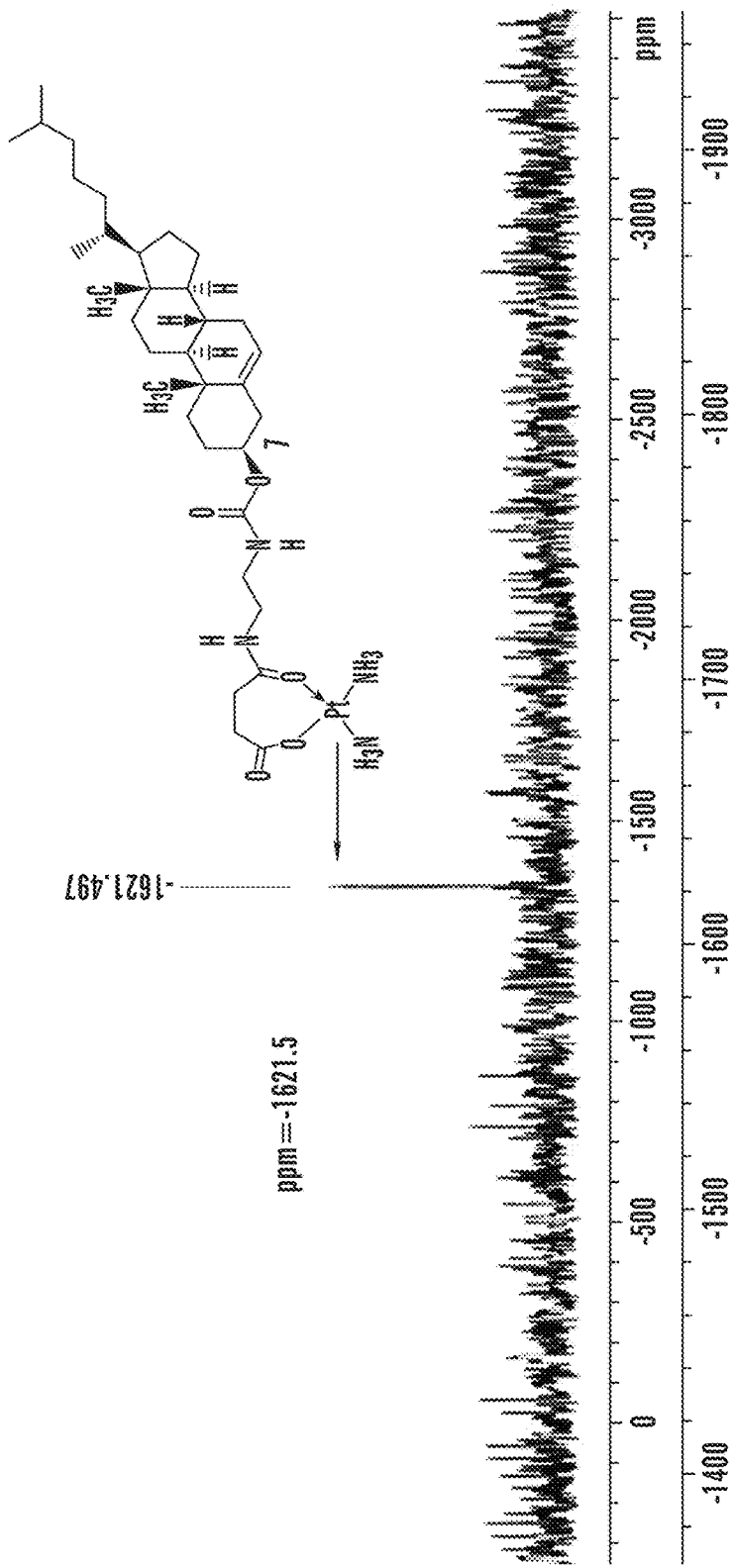
FIG. 14 depicts the $^1$H NMR spectra of cholesterol-ethylenediamine conjugate.
Figure 15:
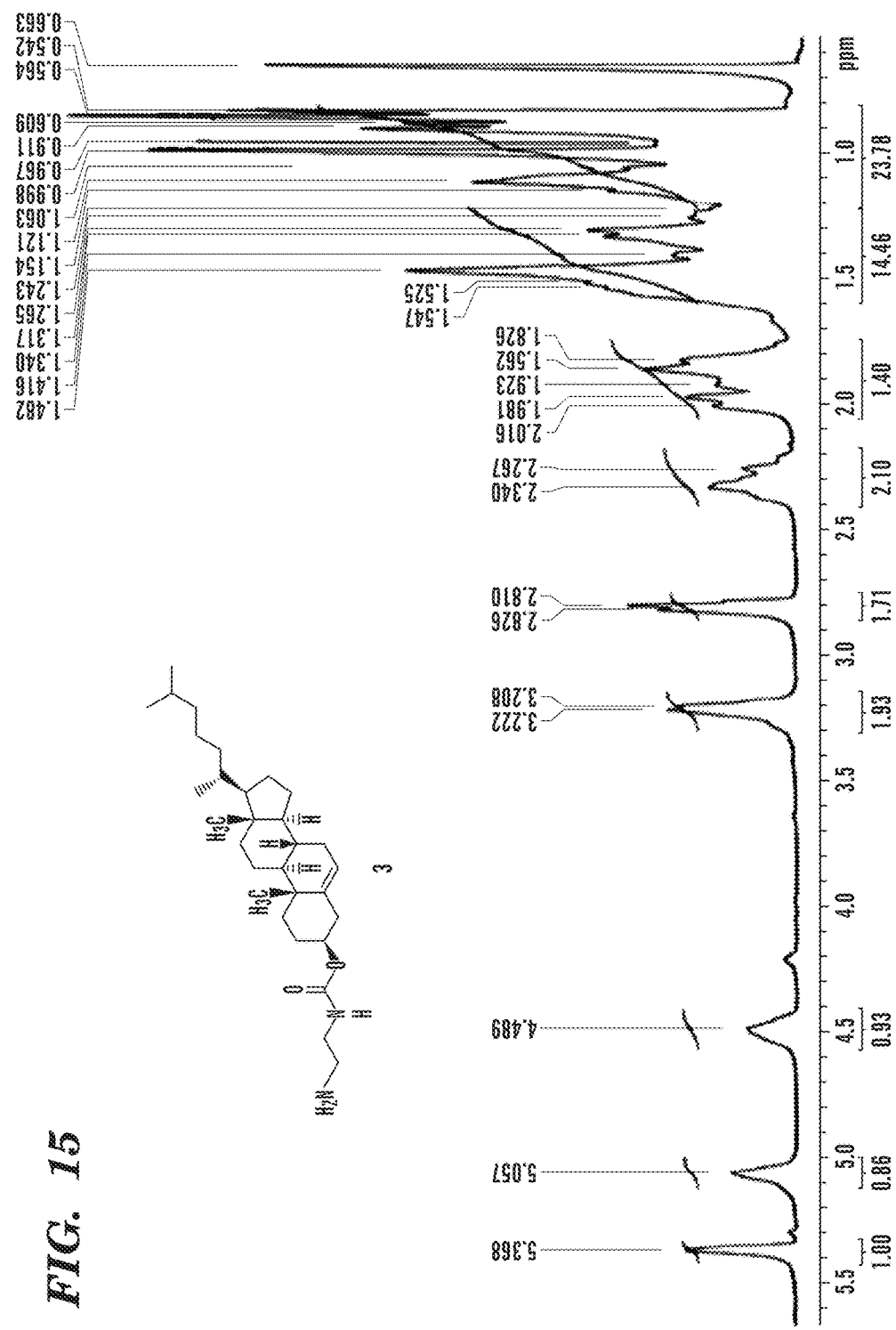
FIG. 15 depicts the $^1$H NMR spectra of cholesterol-ethylenediamine-succinic acid conjugate.
Figure 16:
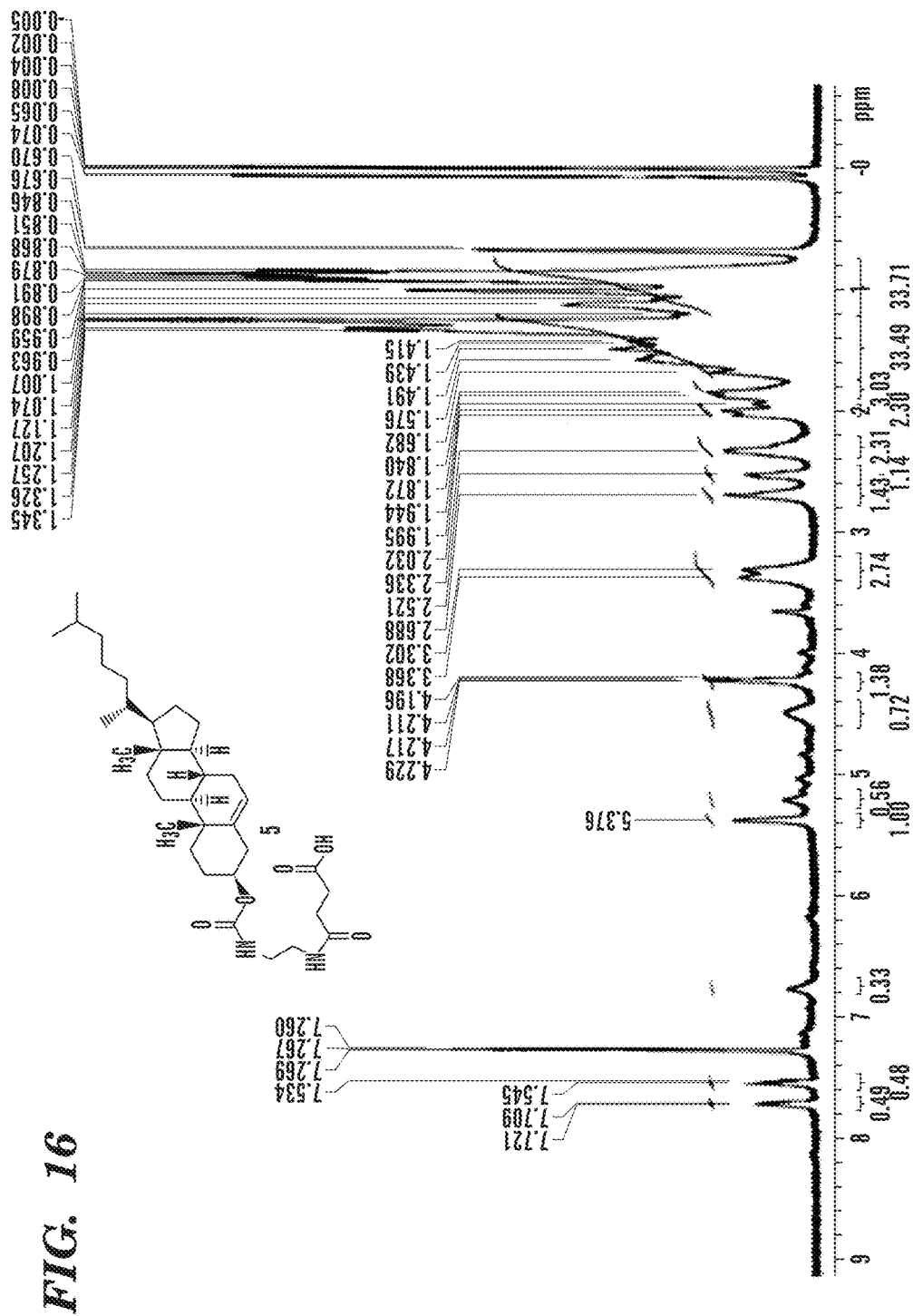
FIG. 16 depicts the 195 Pt NMR spectra of the cholesterol-ethylenediamine-succinic acid conjugate with Pt.
Figure 17:
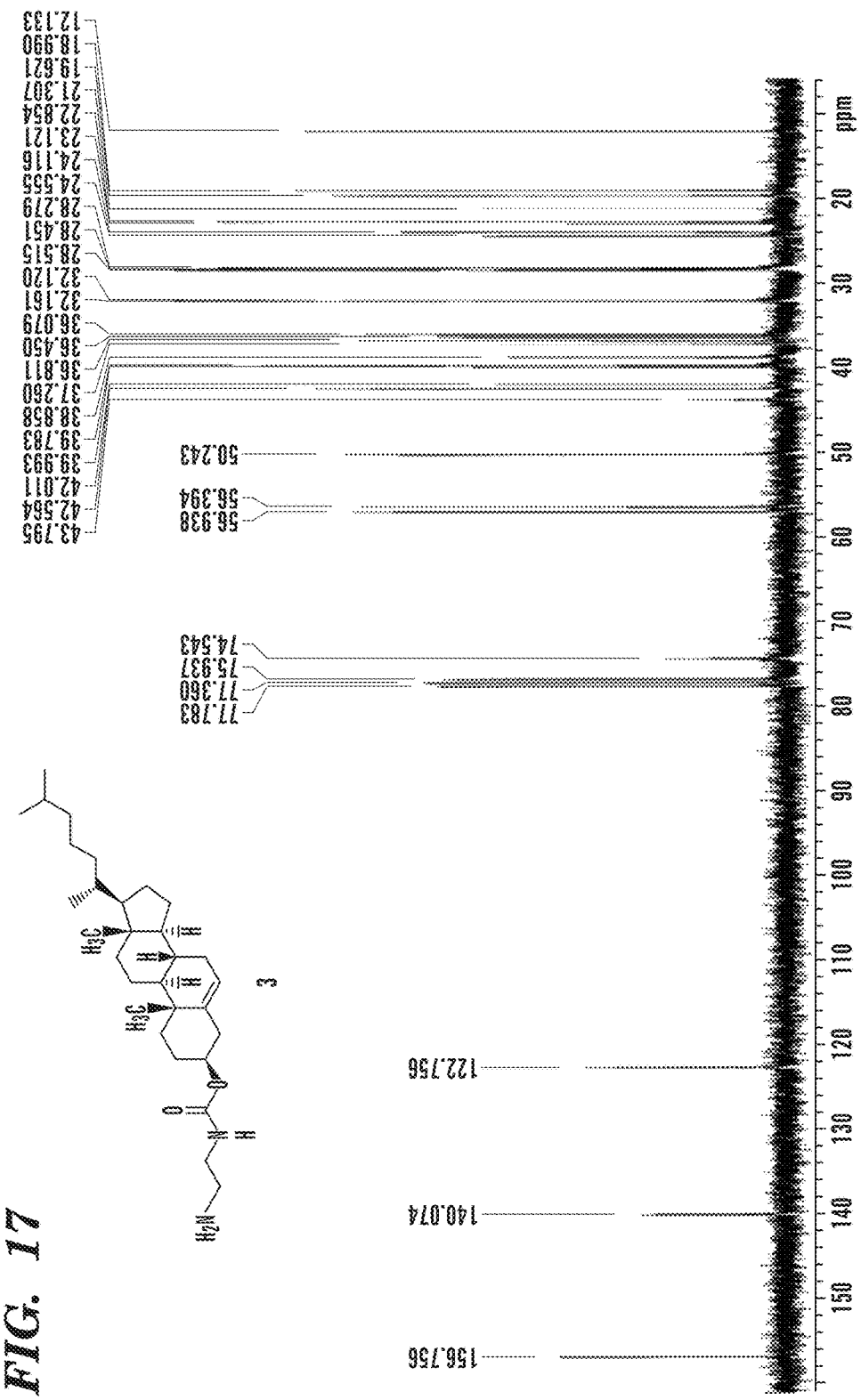
FIG. 17 depicts the $^{13}$C NMR spectra of cholesterol-ethylenediamine conjugate.
Figure 18:
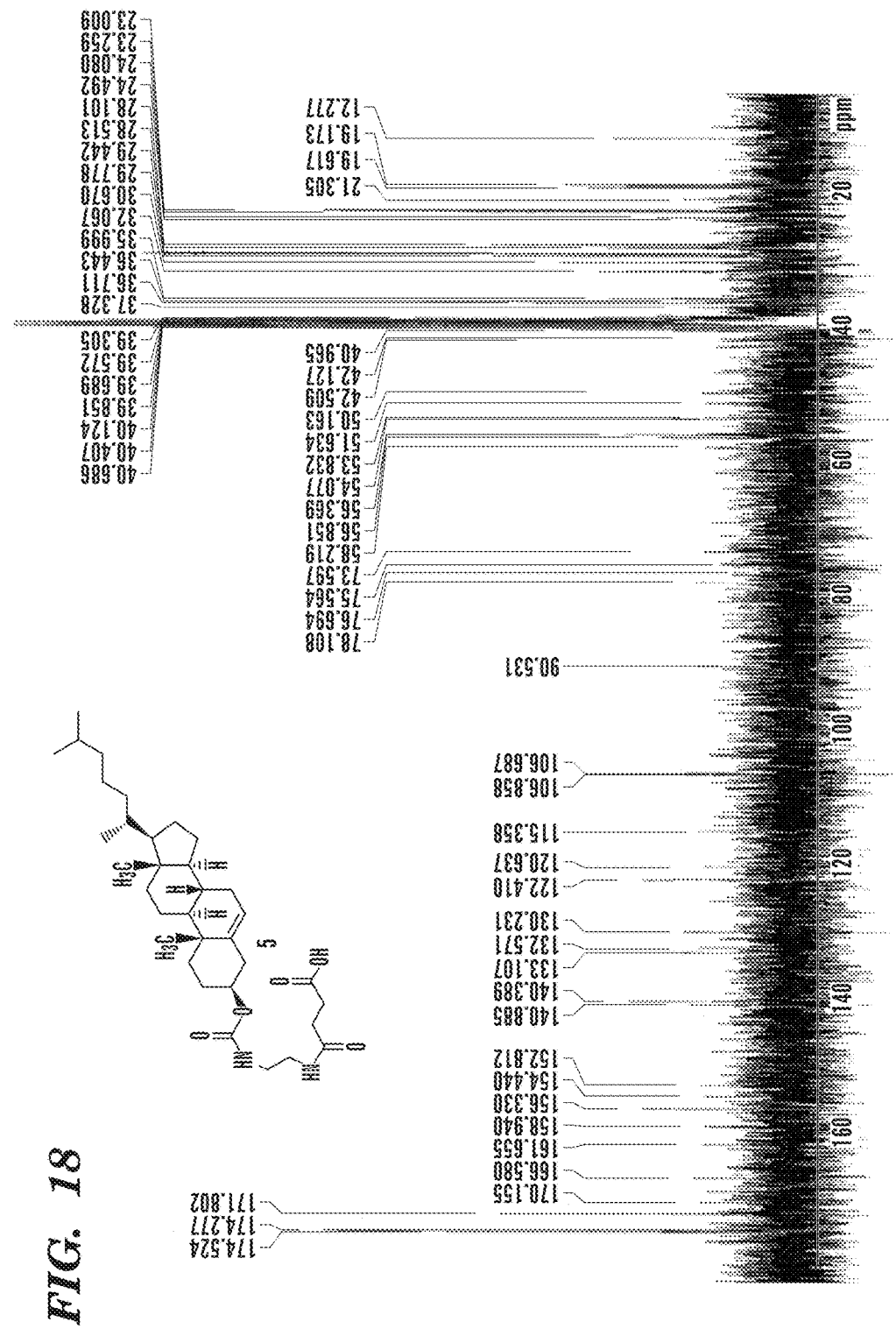
FIG. 18 depicts the $^{13}$C NMR spectra of cholesterol-ethylenediamine-succinic acid conjugate.

Aquation of cisplatin results in the rapid formation of active species cis-[Pt(NH3)2Cl(OH2)]+ and cis-[Pt(NH3)2(OH2)2]2+ with a rate constant of 8×10-5 s-1 (15). In contrast, the rate constant for aquation of carboplatin, where the platinum is coordinated with a stable bidentate 1,1-cyclobutanedicarboxylato ligand, was found to be 7.2×10-7 s-1. This difference in their rate of aquation was matched by their rates of binding to DNA, indicating that the rate of aquation correlates with potency (16, 17). Indeed, we had demonstrated that Pt chelated to a polyisobutylene maleic acid glucosamine copolymer via a monocarboxylato and an O→Pt coordinate bond release of Pt in a pH-dependent manner, and more efficiently than when the Pt was chelated using dicarboxylato bonds or via a monocarboxylato and an N→Pt coordinate bond (18, 19). As a result, we rationalized that the introduction of a coordination environment where the Pt was chelated via a monocarboxylato and an O→Pt coordinate bond is critical to the design of an efficacious platinate. As outlined in the given scheme (FIG. 10A), we first synthesized cholesterol-ethylenediamine conjugate in near quantitative yield (99.1%) by reacting cholesteryl chloroformate with excess ethylene diamine. Next, we introduced monocarboxylato and amide chelating moiety by reacting cholesterol-ethylenediamine conjugate with succinic anhydride (at 95% yield). Finally, the conjugate was reacted with aquated cis-Pt[(NH3)2(OH2)2]2+ in 1:1 molar ratio in acidic pH (pH=6.4) to obtain cholesterol-cisplatin conjugate, characterized by monocarboxylato and an O→Pt coordinate bond of an amide, as indicated by an unique single 195Pt NMR peak at −1,621.497 ppm (FIG. 14). All of the other intermediates were characterized by 1H and 13C NMR spectroscopy (FIGS. 15-18).

Synthesis and Characterization of SACNs.

Figure 10A:
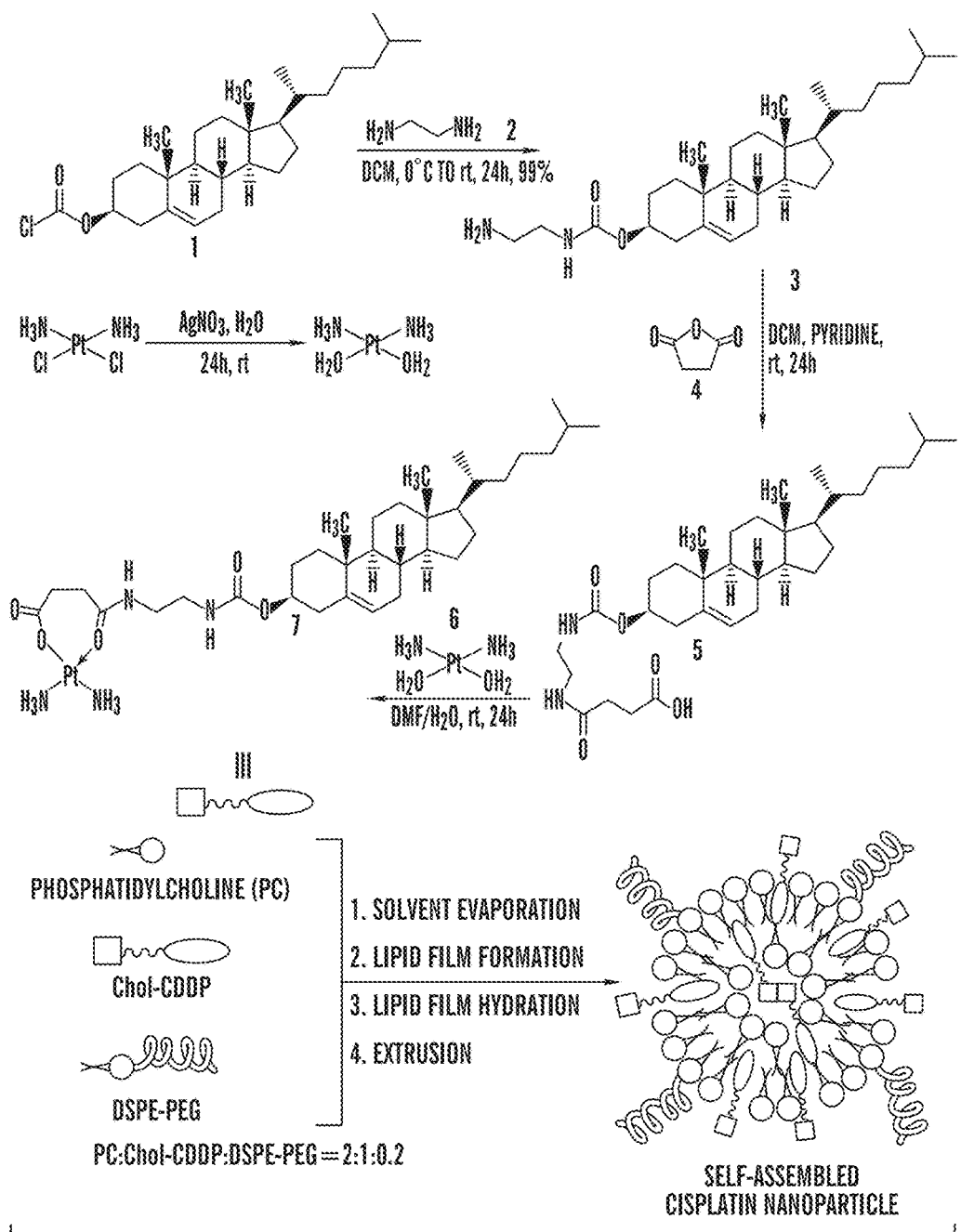
FIGS. 10A-10D demonstrate the synthesis and characterization of SACNs.
Figure 10B:
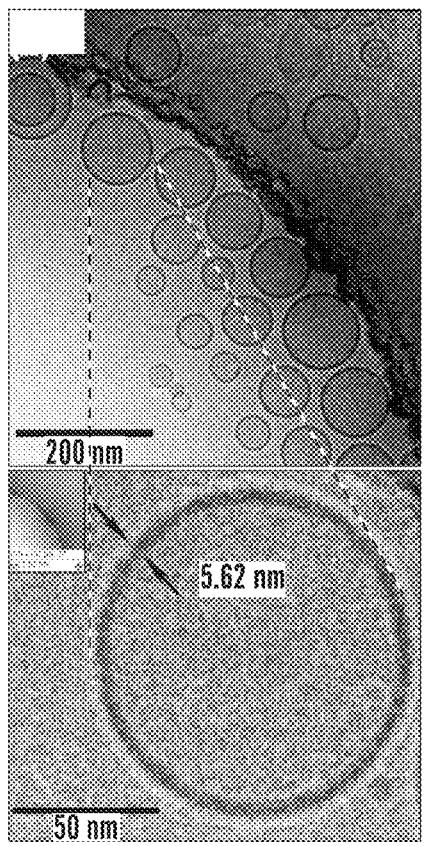
Figure 10D:
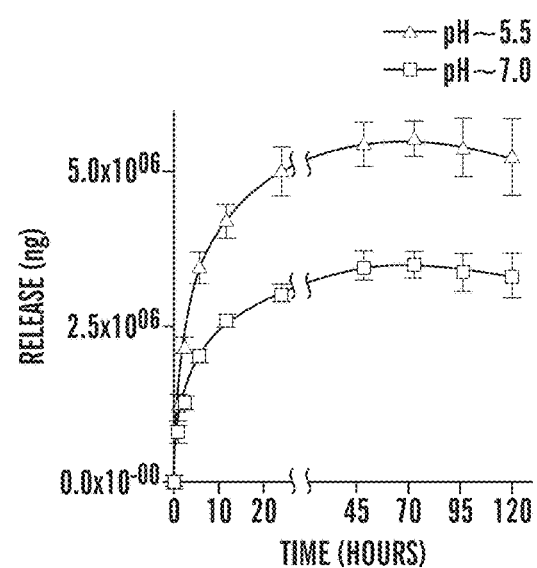
Figure 10C:
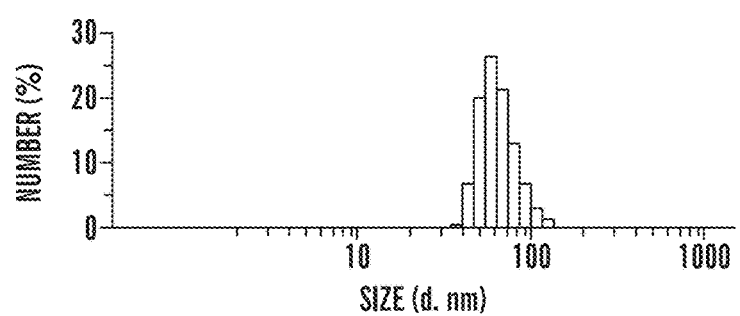

We engineered the SACNs from the cholesterol-succinic acid-platinum (II) molecule, phosphatidylcholine (PC) and 1,2-distearoyl-sn-glycero-3-phosphoethanolamine-N-[amino(polyethylene glycol-2000] (DSPE-PEG) in 1:2:0.2 weight ratio using a lipid-film hydration self assembly method (20) (FIG. 10A). The ultrastructure analysis using cryo-transmission electron microscopy (cryo-TEM) (FIG. 10B) revealed the formation of predominantly uni- and rare multilamellar structures less than 200 nm in diameter, with a membrane thickness ~5 nm. Dynamic light scattering further confirmed the size distribution of SACNs with a mean hydrodynamic diameter of 141.4±1.2 nm (n=9) (FIG. 10C). To validate the kinetics of cisplatin release, SACNs were incubated at acidic pH 5.5 over 120 h, with pH 7 as a reference. As shown in FIG. 10D, SACNs exhibited a pH-dependent sustained release of cisplatin. Interestingly, the rate of release was slower than observed earlier using a polymeric system, indicating that the cholesterol can incorporate into the lipid layer in a manner where the Pt moiety is present both on the outer as well as inner part of the membrane.

In Vitro Efficacy of SACNs.

Figure 11A:
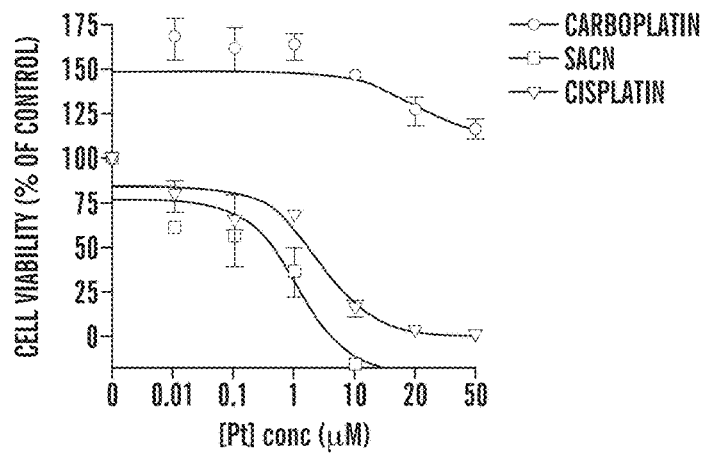
FIGS. 11A-11E demonstrate the in vitro characterization of SACNs.
Figure 11B:
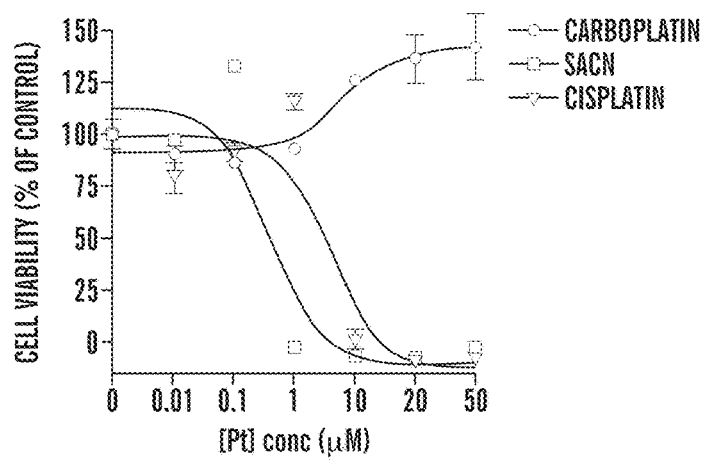
Figure 11C:
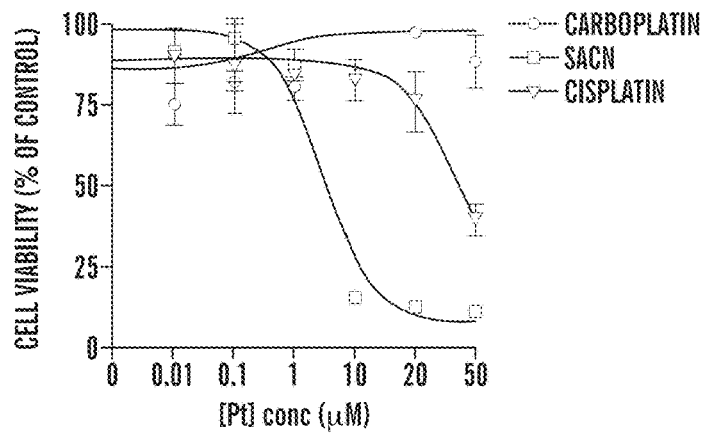
Figure 11D:
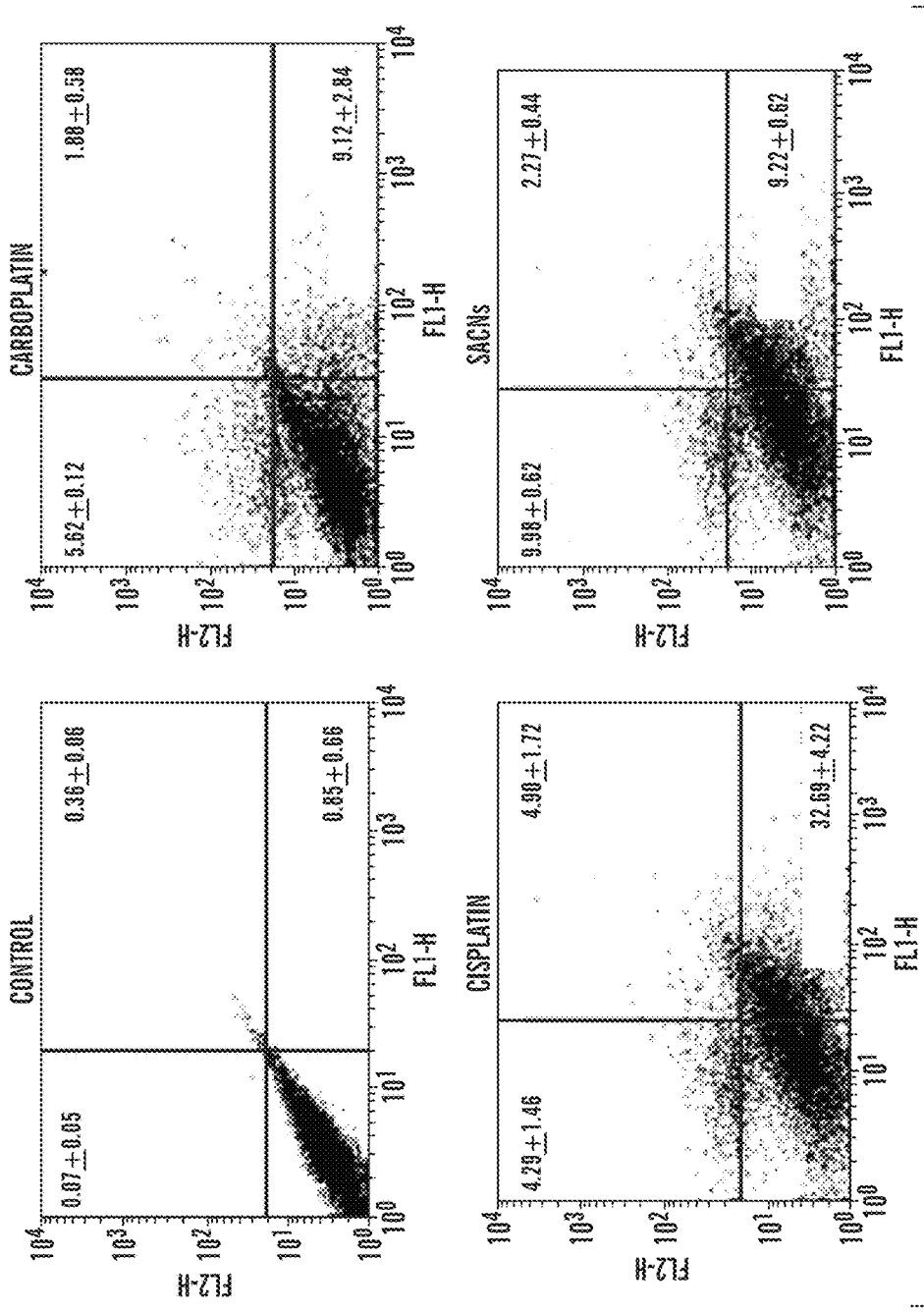
Figure 11E:
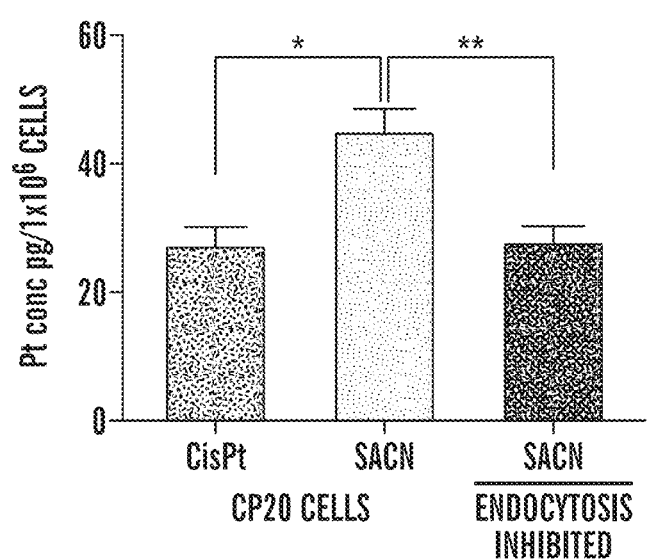

To evaluate the efficacy of the SACNs in vitro, we performed a cell viability assay using Lewis lung carcinoma (LLC) and 4T1 breast cancer cell lines. Cell viability was quantified by using a 3-(4,5-dimethylthiazol-2-yl)-5-(3-carboxymethoxyphenyl)-2-(4-sulfophenyl)-2H-tetrazolium, inner salt assay at 48 h postincubation. As shown in FIGS. 11A-11B, free cisplatin induced LLC and 4T1 cell kill with $IC_{50}$ values of 2.91±0.015 µM and 4.72±0.016 µM, respectively. In neither of these cell lines did carboplatin exert any inhibitory activity at this concentration range. Interestingly, the SACNs were found to be more efficacious than cisplatin against both 4T1 and LLC cells, with $IC_{50}$ values of 0.44±0.016 µM and 1.16±0.016 µM, respectively. We next tested the efficacy of the SACNs in a cisplatin-resistant hepatocellular carcinoma (7404-CP20) cell line. Although the $IC_{50}$ value for free cisplatin in this assay was calculated to be 42.84±0.04 µM, consistent with previously reported values (21), the SACNs were found to be overcome the resistance with an $IC_{50}$ value of 3.02±0.013 µM (FIG. 11C). To elucidate the mechanism of cell death, we incubated 4T1 cells with a sub-$IC_{50}$ concentration of the SACNs, cisplatin or carboplatin, for 24 h. The cells were labeled with FITC-Annexin V that binds to phosphatidylserine, an early marker for apoptosis. As seen in FIG. 11D, treatment with platinates induced both apoptosis and necrosis of the tumor cells, with both cisplatin and SACNs being more efficacious than carboplatin. Studies using FITC-labeled SACNs revealed that the nanoparticles were internalized and localized in the endolysosomal compartment in a temporal manner (e.g. internalization of FITC-SACNs in the endolysosomal compartments within 4 h) (data not shown). This finding is further validated by incubating the tumor cells (4T1 and 7404-CP20) with FITC-labeled SACNs at 37° C. and 4° C., wherein the internalization of SACNs into the cells was decreased in the latter condition (data not shown). To dissect the mechanism underlying the efficacy of SACNs in the cisplatin-resistant 7404-CP20 cell line, we quantified the intracellular concentration of Pt in the cells following incubation with cisplatin or SACNs containing equivalent levels of Pt. As shown in FIG. 11E, the SACNs resulted in significantly elevated intracellular levels of Pt compared with cisplatin. Incubating cells with SACNs at 4° C., which inhibits energy-dependent endocytosis, reduced the intracellular Pt concentration to cisplatin-treated levels, validating that the SACNs can enter these cells via endocytosis.

Efficacy of SACNs in an In Vivo 4T1 Breast Cancer Model.

Figure 12A:
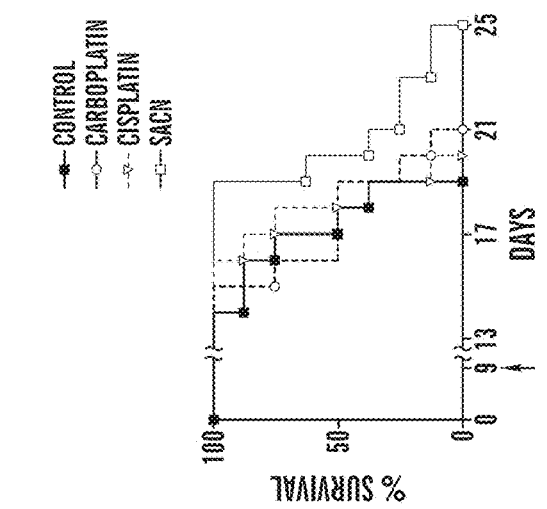
FIGS. 12A-12F demonstrate the in vivo antitumor activity of SACNs in 4T1 breast cancer model.
Figure 12B:
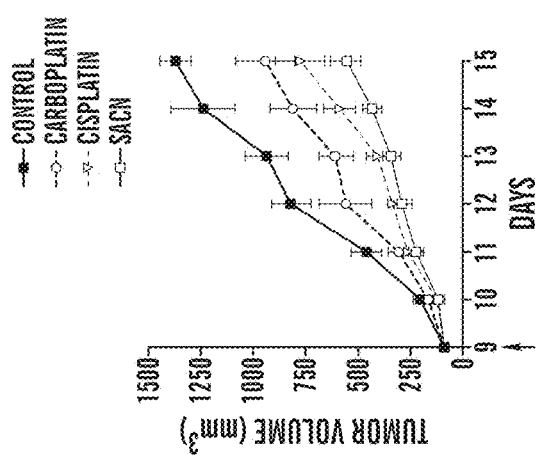
Figure 12C:
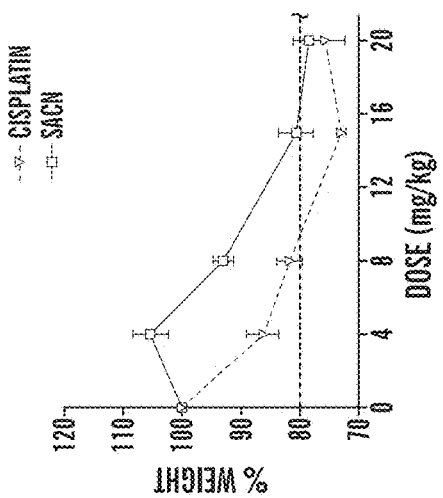

Motivated by the sustained release of Pt and enhanced in vitro efficacy of SACNs, we evaluated its antitumor efficacy in vivo. As the first step, we established the maximum tolerated dose (MTD) for the SACNs in BALB/c mice to be 16 mg/kg compared with 9 mg/kg of cisplatin (FIG. 12A). We next dosed syngeneic BALB/c mice bearing 4T1 breast tumors (mean tumor volume ~100 mm$^3$) with a single dose of cisplatin (8 mg/kg). Other groups of animals received vehicle, carboplatin, or SACNs, (the latter two received a Pt dose equivalent to 8 mg/kg dose of cisplatin). As shown in FIG. 12B, although all of the platinates resulted in significant tumor inhibition compared with the vehicle-treatment, the SACNs exerted the maximal tumor inhibition (P<0.01 vs. control) followed by cisplatin and carboplatin. Furthermore, although treatment with carboplatin or cisplatin exerted only minor increase in survival over vehicle-treated controls, the SACNs significantly increased overall survival trend (FIG. 12C).

Figures 12D, 12E, 12F:
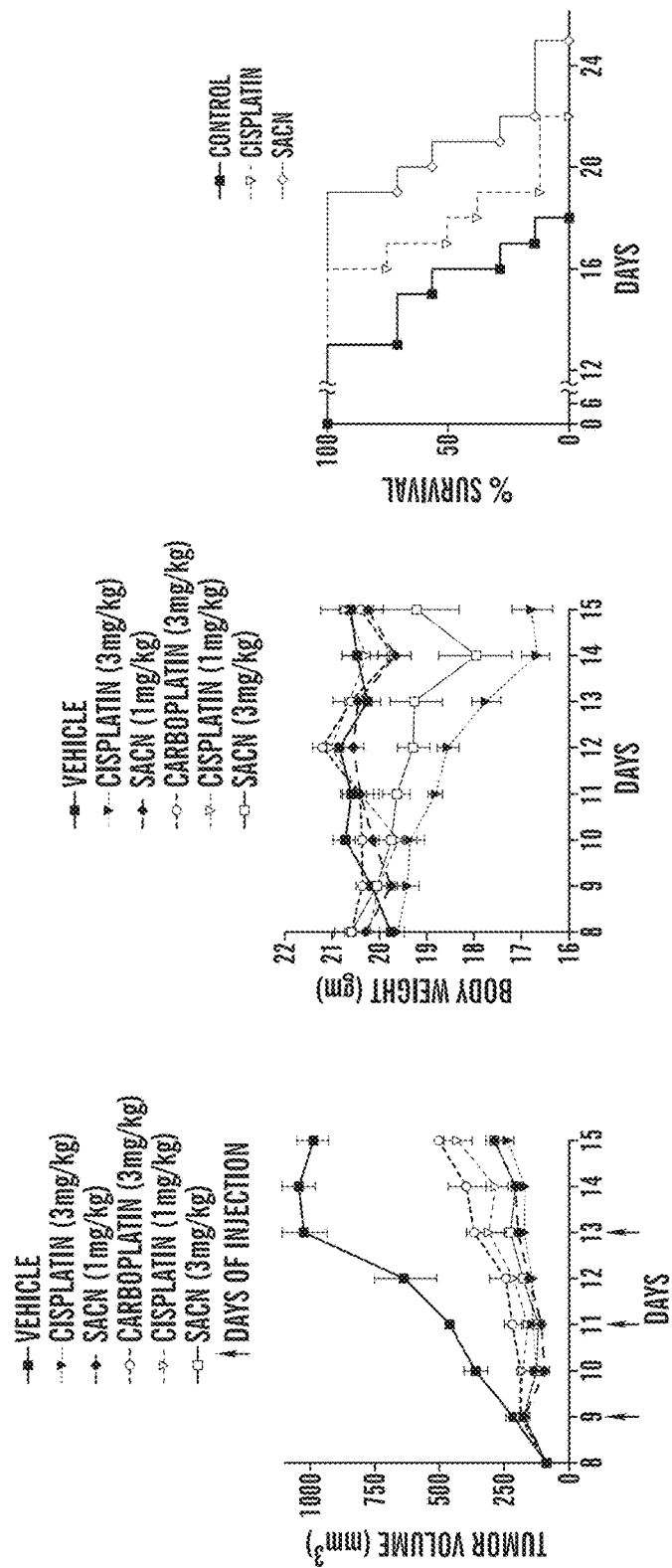

We next tested the effects of multiple low-dose treatment with cisplatin, carboplatin, or the SACNs, with the highest platinum dose in each case adding up to the levels of Pt delivered at the MTD of cisplatin. Two additional groups were included that were treated with a lower dose of cisplatin or SACNs (equivalent of 1 mg/kg dose of platinum). As shown in FIG. 12D, treatment with cisplatin resulted in a dose-dependent inhibition of tumor growth. Interestingly, although at the highest doses the tumor inhibition with the SACNs or cisplatin were identical, at the lower doses the SACNs exerted a superior antitumor effect compared with free cisplatin (P<0.05, ANOVA). Furthermore, cisplatin resulted in a significant reduction in mean body weight (P<0.05, ANOVA) compared with the SACN-treated groups (FIG. 12E), indicating that the latter can reduce the systemic toxicity associated with cisplatin chemotherapy. Interestingly, even at the lower dose both the SACNs and cisplatin exerted greater tumor inhibition as opposed to the higher dose of carboplatin (FIGS. 12D-12E). At the higher dose, both cisplatin and SACNs were found to increase survival, although the latter was superior (FIG. 12 F).

Figure 13A:
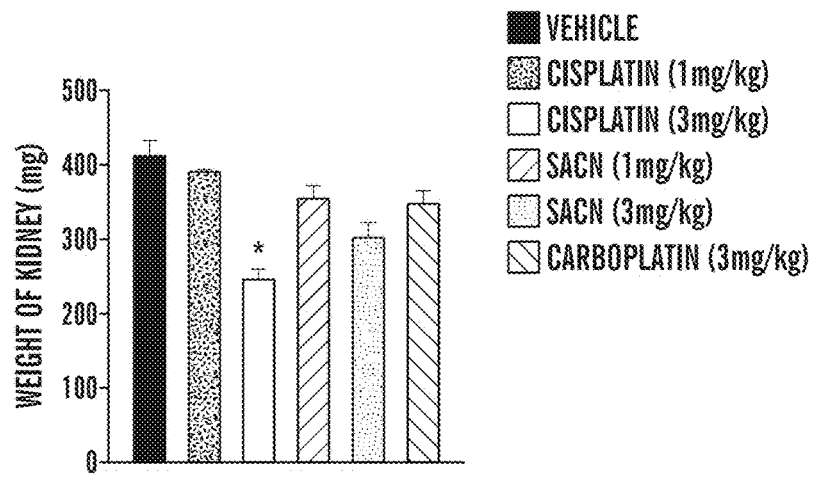
FIGS. 13A-13B demonstrate that SACNs preferentially accumulate in the tumor bypassing the kidney, and exert reduced nephrotoxicity. Mice were treated with PBS, carboplatin (3 mg/kg), cisplatin (3 mg/kg and 1 mg/kg), and SACNs (cisplatin NP, 3 mg/kg and 1 mg/kg) (n=4, doses are Pt equivalent) on days 9, 11, and 13 posttumor implantation.

To elucidate the mechanism underlying of increased in vivo efficacy, the tumors were excised posttreatment and processed for TUNEL as a marker for apoptosis. SACNs induced significantly greater apoptosis than cisplatin, but at the higher doses both the SACNs and cisplatin induced similar apoptosis, consistent with the tumor inhibition results (data not shown). However, at the latter dose level, cisplatin but not SACNs resulted in significant nephrotoxicity as evident by reduced kidney weight and up-regulation of kidney injury molecule-1 (KIM1) expression (FIG. 13A). Additionally, TUNEL of the excised kidney sections indicated significant apoptosis in cisplatin-treated mice, whereas the SACNs demonstrated negligible apoptosis even at the higher dose (data not shown).

SACNs Home Preferentially to the Tumors and Bypass Kidney.

Figure 13B:
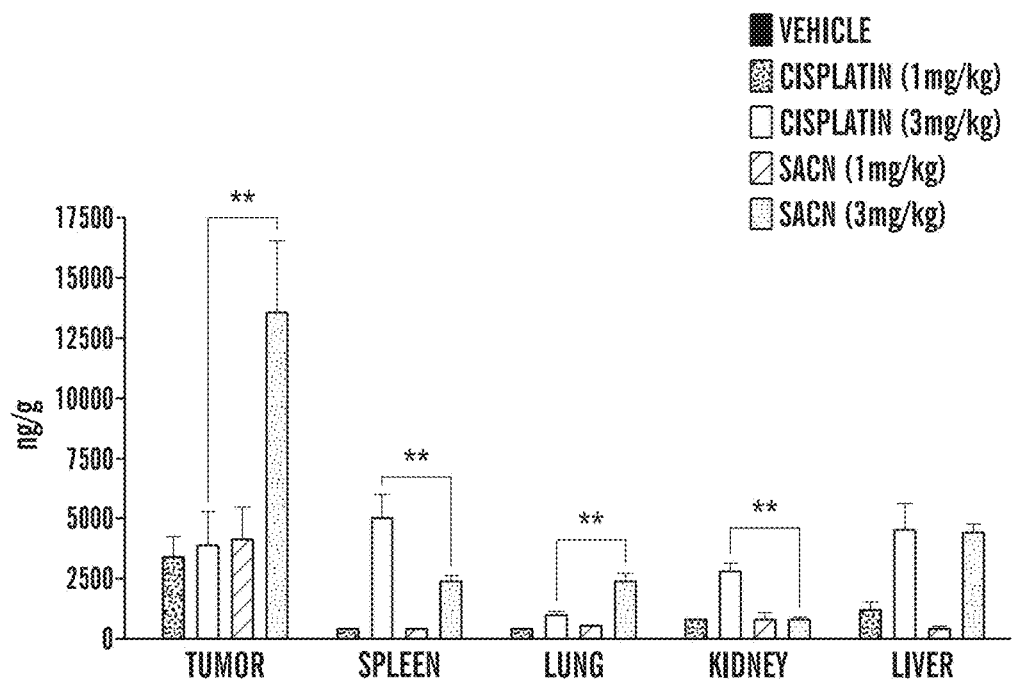

To elucidate the mechanism underlying the enhanced apoptosis in the tumor and reduced nephrotoxicity evident with the SACNs, we probed the tumor and reticuloendothelial system (RES) organs for the platinum biodistribution. Tumor-bearing animals were dosed with cisplatin or SACNs at doses equivalent to 1 and 3 mg/kg of platinum. As shown in FIG. 13B, there was a dose-dependent accumulation of platinum (as quantified per gram of tissue using inductive-coupled plasma atomic absorption spectra) in the RES tissues. Interestingly, the SACNs (3 mg/kg Pt dose) resulted in significantly higher concentration in the tumor than achieved following dosing of an equivalent amount of cisplatin. Furthermore, at this dose, cisplatin resulted in significantly higher platinum build-up in the kidney, which could account for cisplatin-associated nephrotoxicity, compared with the SACN-treated groups.

Efficacy of SACNs in an In Vivo K-Ras$^{LSL/+}$/Pten$^{fl/fl}$ Ovarian Cancer Model.

Figure 19A:
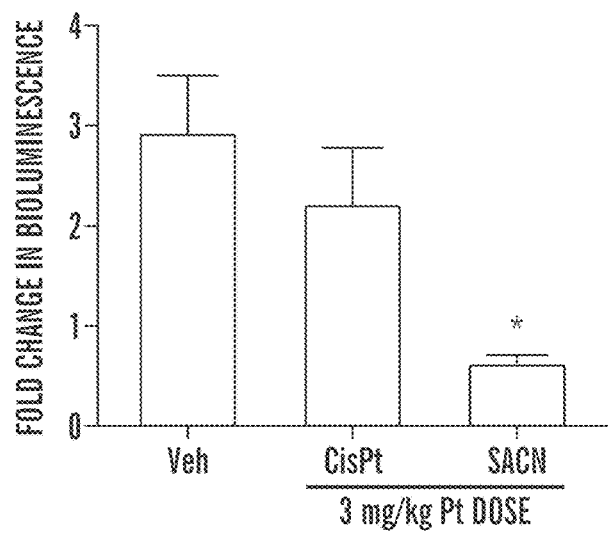
FIGS. 19A-19B demonstrate the in vivo anti-tumor activity of SACNs in a K-RasLSL/+/Ptenfl/fl ovarian cancer model.
Figure 19B:
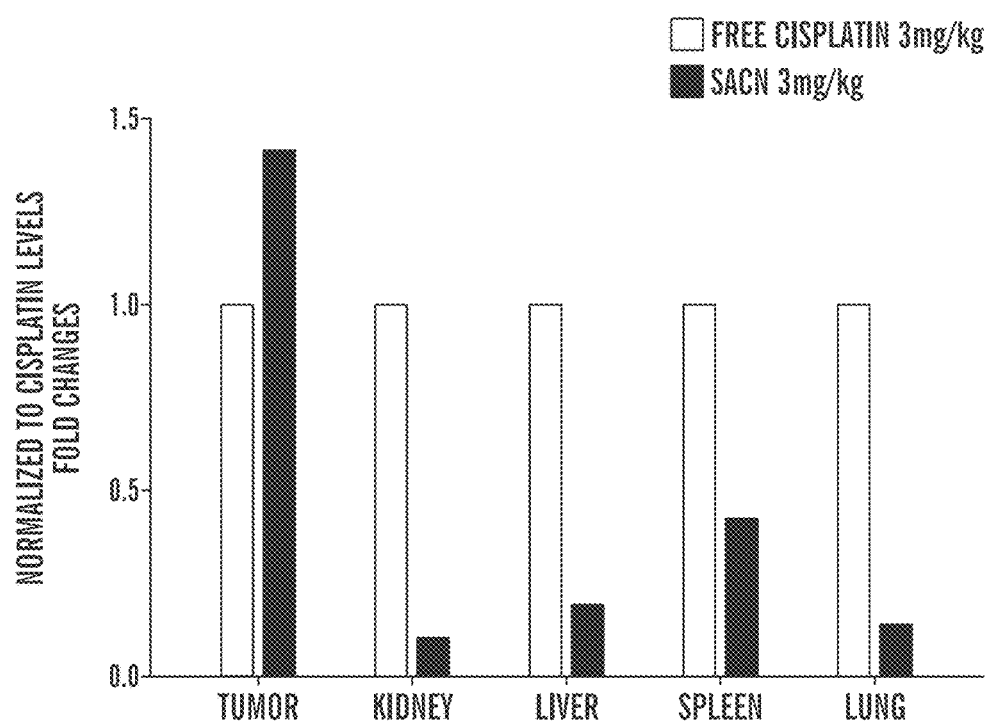
Figure 20:
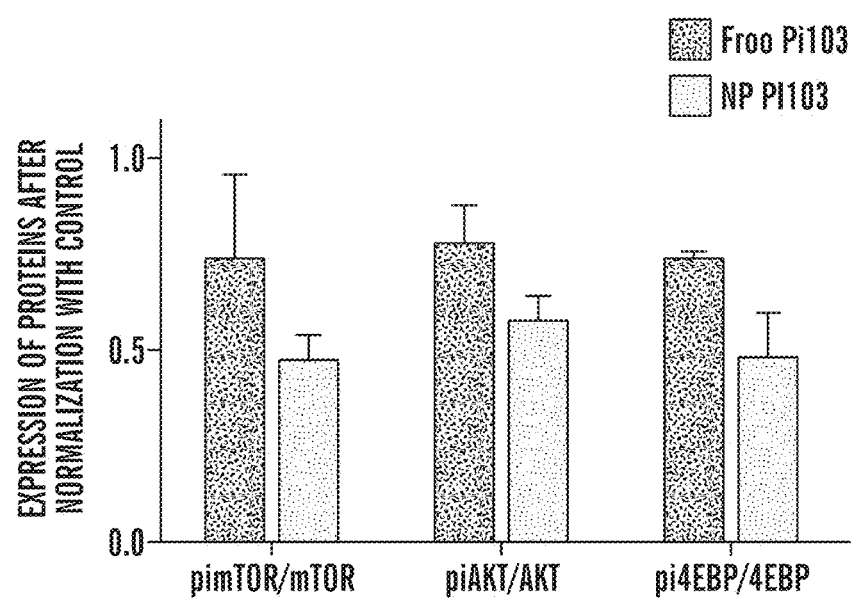
FIG. 20 depicts the quantification of the data shown in FIG. 3E.
Figure 21A:
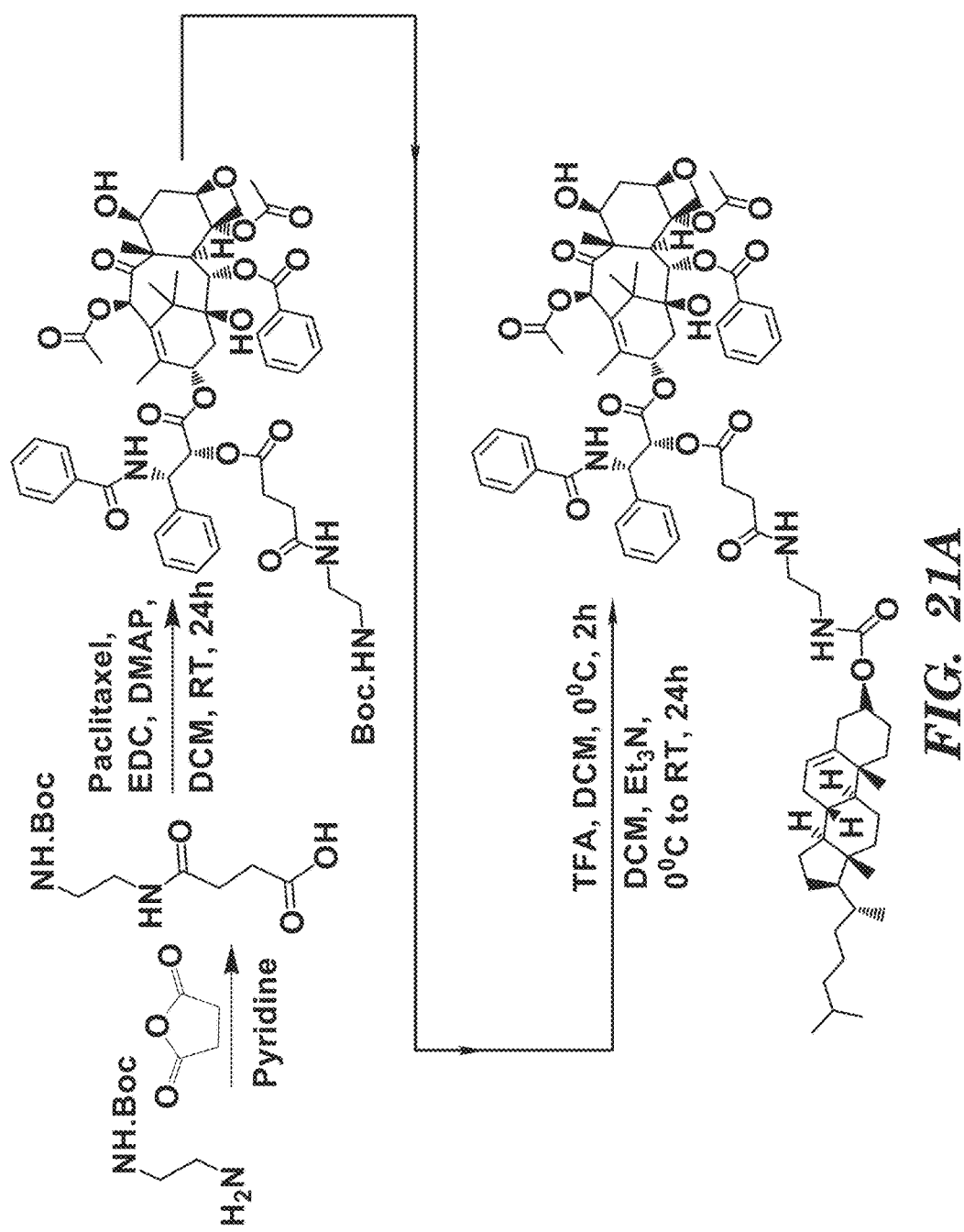
Figure 21B:
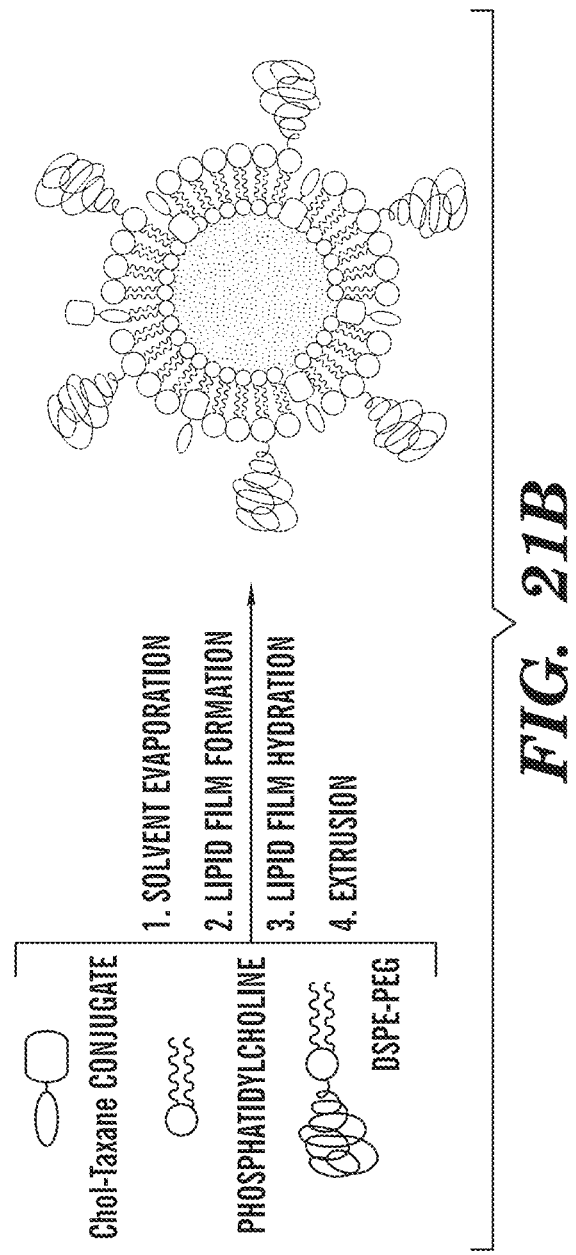
Figure 21D:
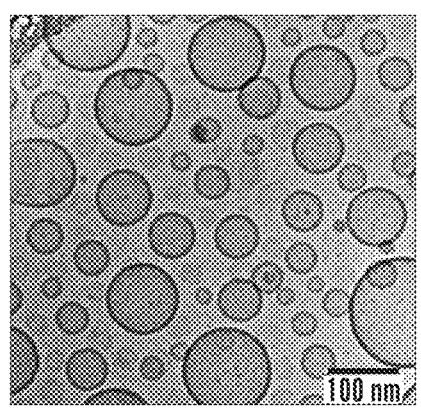
Figure 21F:
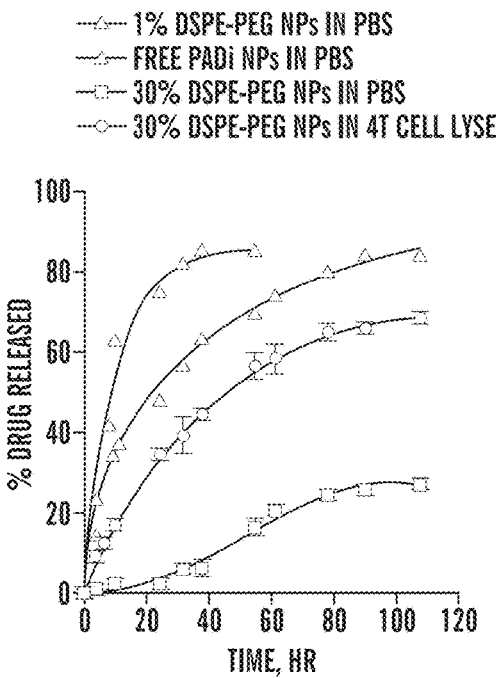
Figure 21E:
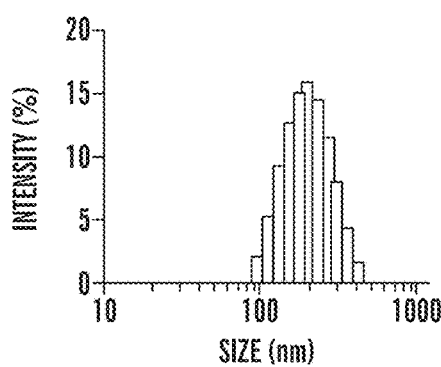
Figure 21G:
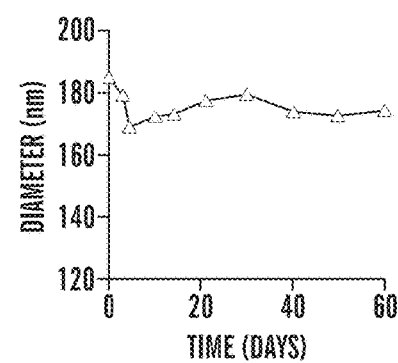
Figure 22B:
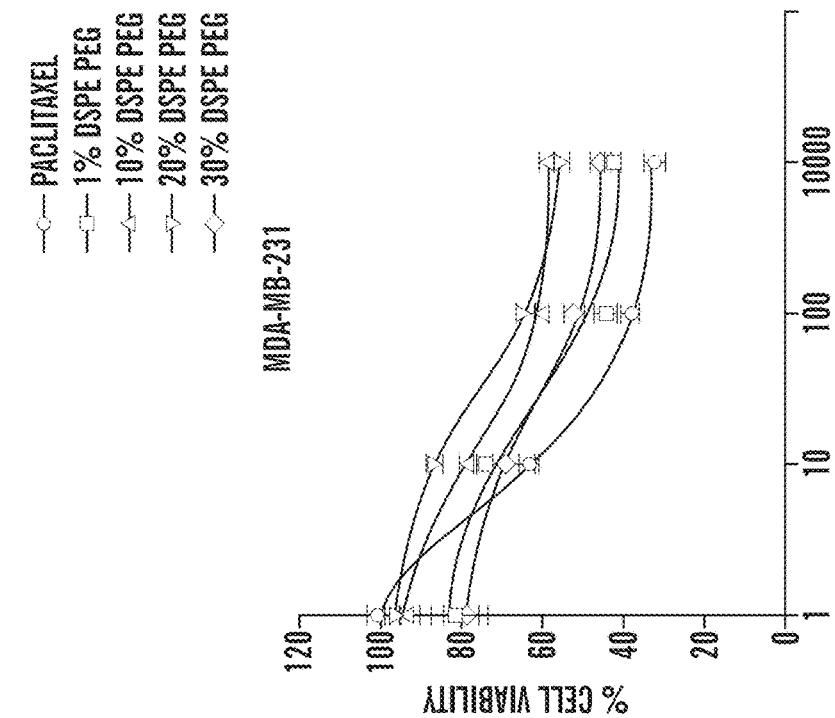
FIGS. 22A-22F demonstrate the in vitro characterization of Pacli-chol nanoparticles.
Figure 22A:
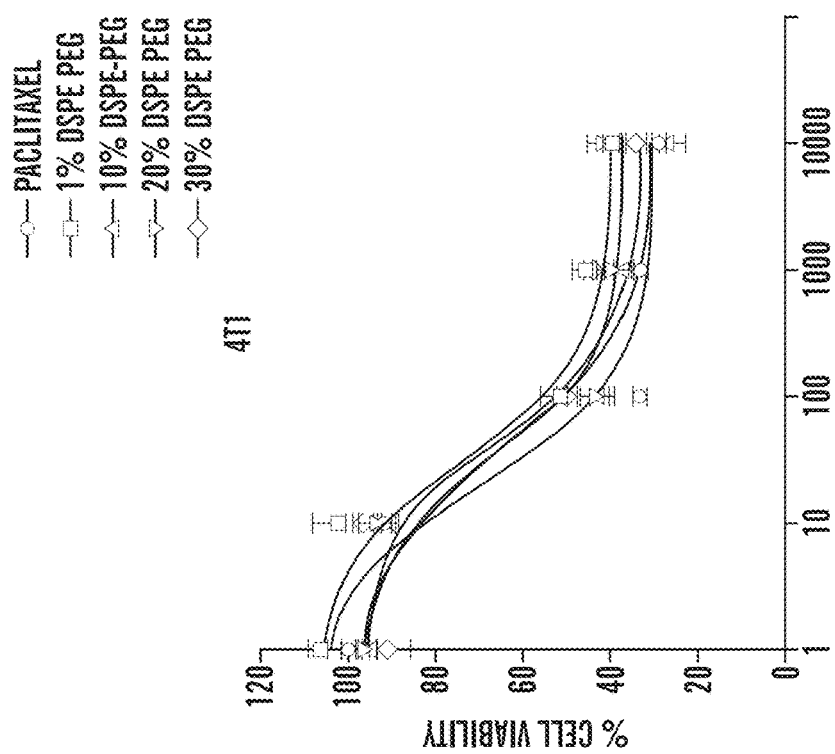
Figure 22C:
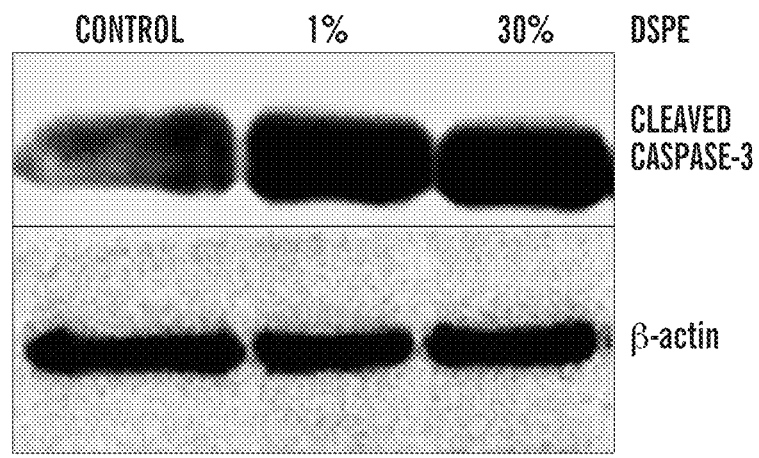
Figure 22D:
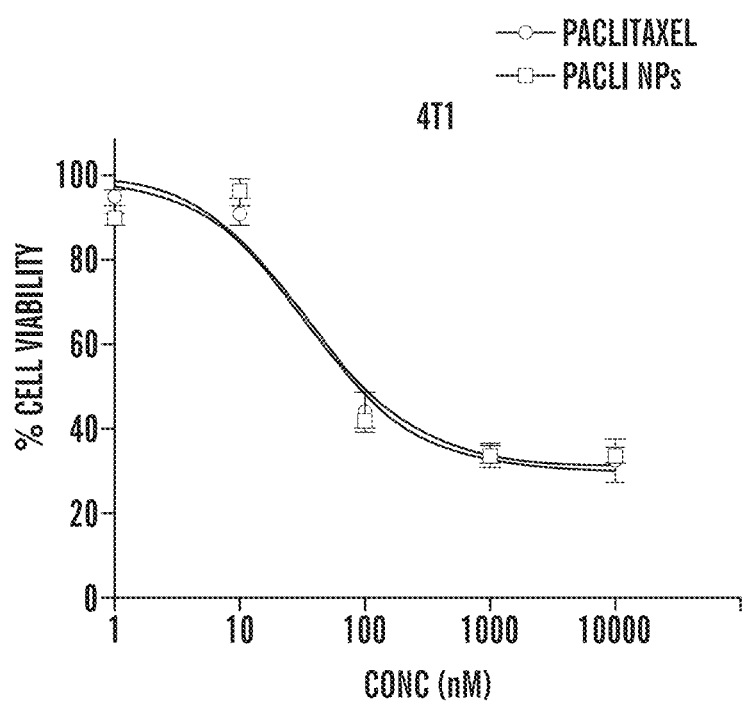
Figure 22E:
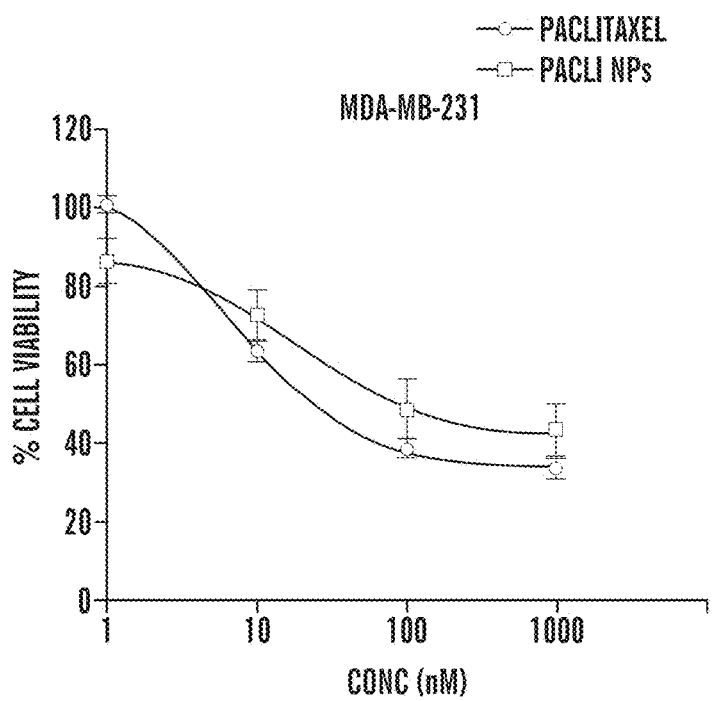
Figure 22F:
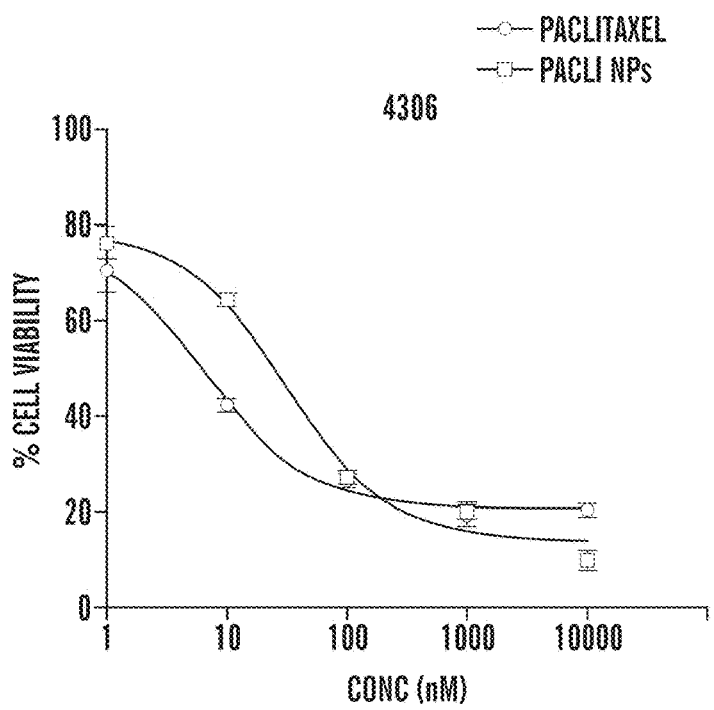
Figure 23A:
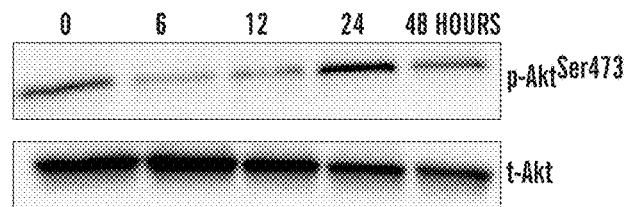
Figure 23B:
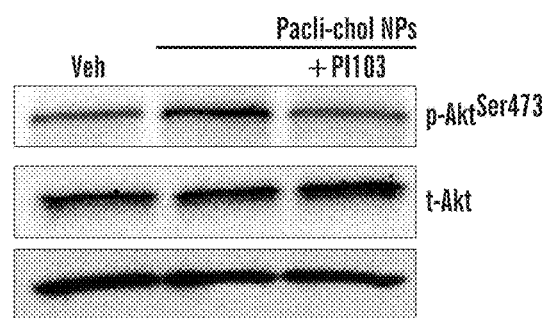
Figure 23C:
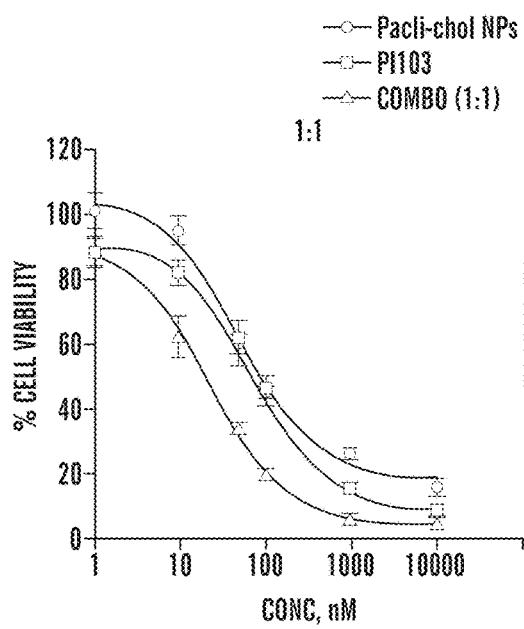
Figure 23D:
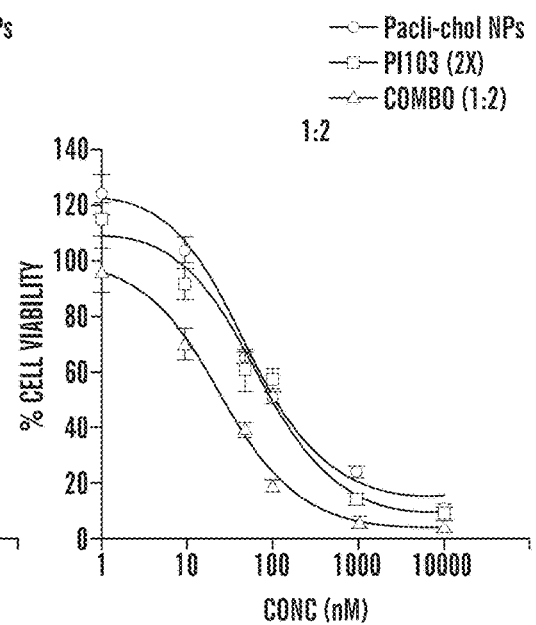
Figures 23H, 24A:
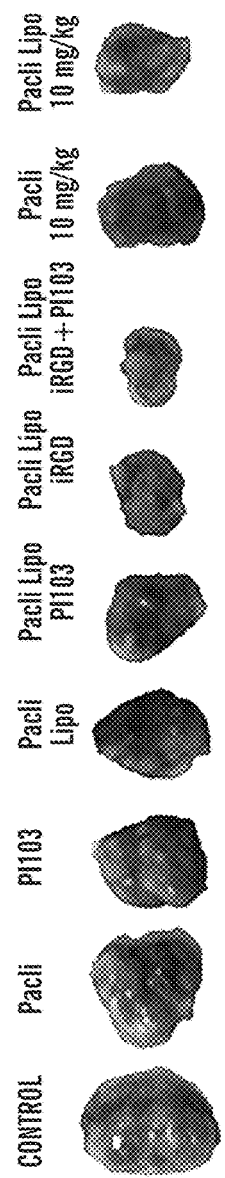
Figure 24B:
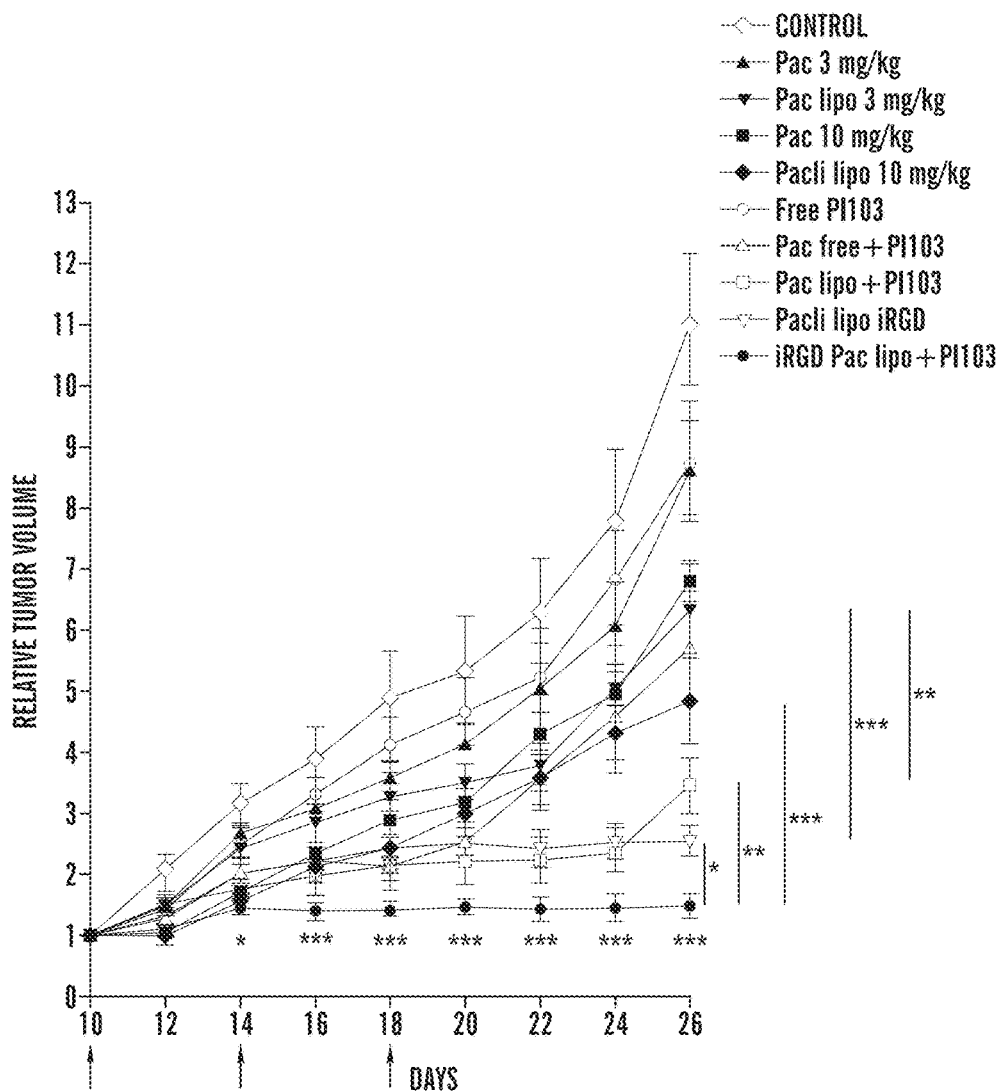
Figure 24C:
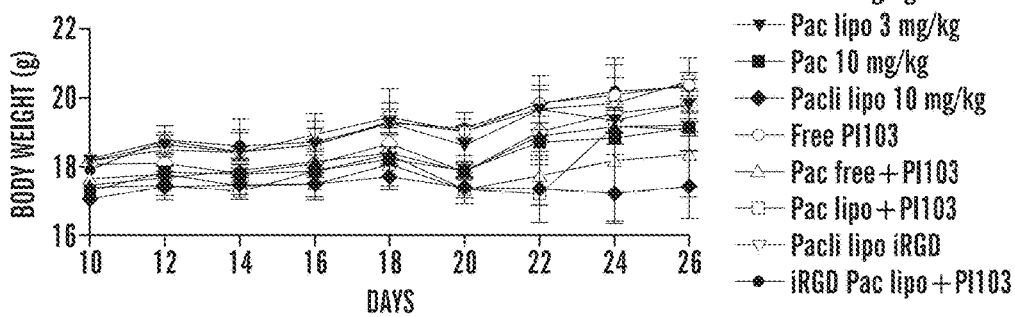

In recent years, it has been well established that frequent somatic PTEN and K-Ras mutations are implicated in wide spectrum of human cancers, including endometrioid ovarian cancer (2211-24). As shown in FIG. 19A, the animals bearing medium and large K-ras$^{LSL/+}$/Pten$^{fl/fl}$ ovarian cancer treated with SACNs (Pt dose equivalent to 3 mg/kg of cisplatin) resulted in greater regression compared with cisplatin treatment. TUNEL revealed apoptosis in both SACN- and cisplatin-treated tumor. However, although cisplatin induced apoptosis of nephrons, negligible cell death was evident in the kidney with SACNs (data not shown), which correlated with elevated levels of Pt in the tumor with reduced concentrations in the kidney following SACN treatment compared with cisplatin-treatment (FIG. 19B).

Discussion

Supramolecular chemistry, the development of complex chemical systems from molecular building blocks that interact via noncovalent intermolecular forces (25), has emerged as a field that explains and impacts many biological and physical concepts. In an elegant perspective, Jean-Marie Lehn had envisioned a unique paradigm called supramolecular nanochemistry (26). Indeed, gadolinium (III)-encapsulated supramolecular nanoparticles were recently shown to enhance relaxivity with increased sensitivity, and serve as a tool for diagnosis of cancer metastasis (27). In another study, camptothecin was encapsulated in a supramolecular nanoparticle (28). However, although these emerging studies have focused on using supramolecular interactions to encapsulate molecules for targeting cancer, we report here the rational redesign of a cancer chemotherapeutic drug to enable supramolecular assembly into a nanostructure.

Although cisplatin [cis-dichlorodiamineplatinum (II)] is the drug of choice as a first or second line chemotherapy for most cancers, its clinical efficacy is dose-limited because of nephrotoxicity, resulting from a peritubular uptake in both proximal and distal tubules mediated by a organic cation transporter 2 (29). As nanoparticles >5.5 nm can bypass glomerular filtration (13), cisplatin made an excellent candidate for rational engineering into a supramolecular nanostructure to potentially overcome nephrotoxicity. As the first step, we converted cis-platinum (II) into an amphiphile via conjugation to a cholesterol succinic acid conjugate, which facilitated the supramolecular assembly of this platinate into SACNs with PC and DSPE-PEG arising from hydrophilic-hydrophobic interactions (30, 31). Cholesterol and PC were selected as both are components of biological cellular membranes, and the 3β-OH group of cholesterol is easily amenable to conjugation, and alter pharmacodynamic/pharmacokinetic profile as well as cellular uptake of the active agent (32). DSPE-PEG was incorporated to impart "stealth" property to SACNs as surface modification of nanoparticles with PEG has been reported to decrease interaction with opsonin (33), and thereby reduce clearance by the RES. Indeed, consistent with the above hypothesis, our biodistribution studies revealed that the SACNs could bypass glomerular filtration in the kidney, evident by the significantly lower Pt concentration in the kidney compared with cisplatin. This finding was further validated by low expression of KIM1, an early marker for kidney injury (34), with concomitant decrease in kidney apoptosis observed following SACNs treatment. Furthermore, the SACNs preferentially accumulated in the tumor are consistent with previous reports where such stealth nanosystems were reported to home into the tumors via the EPR effect (5).

Although the SACNs enable enhanced intratumoral concentrations, a critical driver of efficacy is the efficient release of active cis-[Pt(NH$_3$)$_2$]$^{2+}$ moiety. For example, the stable cyclobutanedicarboxylate chelating ligand lowers the rate of aquation of carboplatin by two-to-four orders of magnitude than cisplatin, and to obtain cytotoxicity comparable to cisplatin a 4- to 20-fold higher dose of carboplatin is required (16). Similarly, AP5280, a N-(2-hydroxypropyl) methacrylamide copolymer-bound platinum was found to exert minimal nephrotoxicity in clinical studies (35), but was less potent than carboplatin because the platinum is held to an aminomalonic acid chelating agent coupled to the COOH terminal glycine of a tetra-peptide spacer (36). The criticality in the amphiphile design in this study was therefore the introduction of the monocarboxylato and O→Pt coordination environment between the platinum and the leaving group, in this case the cholesterol succinic acid conjugate. We have previously demonstrated that this coordination environment was more efficient in releasing activated Pt in a pH-dependent manner than when coordination is via more stable dicarboxylato linkages or monocarboxylato and N→Pt linkage (18, 19). This finding is consistent with the increased potency of SACNs compared with carboplatin as observed in vitro and validated by increased tumor cell apoptosis and necrosis. Interestingly, the SACNs also exhibited slightly improved efficacy compared with cisplatin in the breast cancer (4T1) and LLC cells, and was significantly superior to cisplatin in the hepatocellular carcinoma (7404-CP20), which could be explained by the SACNs harnessing additional mechanisms of uptake into the 7404-CP20 cells besides traditional platinum transporters that are mutated in these cells. Indeed our studies using fluorescently tagged SACNs revealed internalization via endocytosis in a temporal manner.

Inhibition of endocytosis decreased the intracellular levels of Pt following SACN treatment to that achieved by treatment with cisplatin. Although previous studies have reported that cholesterol has been shown to facilitate cellular uptake through caveolin-mediated endocytosis (37), we observed that pretreatment of the cells with chlorpromazine, an inhibitor of clathrin-mediated endocytosis, nystatin, a caveolae-mediated endocytosis inhibitor, or cytochalasin D, an inhibitor of macropinocytosis/phagocytosis, could not fully abolish internalization of the SACNs (data not shown), which could suggest a redundancy in the mechanisms of SACN internalization. However, it should be noted that recent reports have questioned the specificity of endocytosis inhibitors (38), and in our study we did observe changes in cellular morphology, even at lower doses and short incubation times. SACNs were also internalized in a similar manner by endothelial cells and fibroblasts in vitro (data not shown). Without wishing to be bound by theory, in vivo, the preferential EPR-mediated intratumoral accumulation, and the tendency of SACNs to internalize within the low pH endolysosomal compartment together with the predisposition of the SACNs to release activated cis-$[Pt(NH_3)_2]^{2+}$ in an acidic environment, may contribute to preferential tumor targeting.

Although the SACNs exhibit increased potency, we also observed an increase in the MTD in vivo compared with cisplatin, suggesting that it may be possible to overcome the dosing limits associated with cisplatin in the clinics. We selected the 4T1 breast cancer and the genetically engineered K-ras$^{LSL/+}$/Pten$^{fl/fl}$ ovarian adenocarcinoma mouse models for our in vivo studies because these closely mimic human tumor progression. Interestingly, even at a single sub-MTD platinum dose comparable to the MTD of cisplatin, the SACNs exerted superior antitumor efficacy, both in terms of tumor inhibition and survival, which could be attributed to the preferential accumulation and increased potency. Furthermore, there may be a metronomic dosing effect involved in the therapeutic outcome potentially arising from the sustained release because, even at the lower doses, SACNs were more efficacious than cisplatin. Interestingly, recent clinical reports have indicated that metronomic dosing of cisplatin exerts an antiangiogenic effect (39). Interestingly, we observed that administration of lower multiple doses of cisplatin was more effective in increasing survival compared with a single MTD. This finding indicates that therapeutic efficacy of SACNs can be optimized by tailoring the dosing regimen.

The results described herein demonstrate that integrating rational drug design and supramolecular nanochemistry can permit a powerful strategy for drug development. Furthermore, because platinum-based chemotherapeutics form the frontline therapy for a broad range of cancers, including testicular, ovarian, cervical, endometrial, bladder, head and neck, lung, and gastro-esophageal cancers, the increased efficacy and improved toxicity profile, resulting from an increase in the molecular dimension through supramolecular assembly, indicates that the constructed nanostructure can be efficacious for treatment.

Materials and Methods

Synthesis and Characterization of SACNs.

Briefly, a thin and uniform lipid-drug film of PC, cholesterol-cisplatin conjugate, and DSPE-PEG was coated using a rotary evaporator, then hydrated for 1 h at 60° C., passed although Sephadex G-25 column, and extruded at 65° C. to obtain sub-200 nm particles. Nanoparticles were analyzed using a nanozetasizer and using cryo-TEM. For release kinetics, drug loaded nanoparticles were suspended in buffer (pH=5.5 or 7) and sealed in a dialysis membrane (molecular weight cutoff=500 Da). The dialysis bags were incubated in 30 mL PBS buffer at room temperature with gentle shaking. An aliquot was collected from the incubation medium at predetermined time intervals, and the released drug was quantified.

Cell Viability/Apoptosis Assay.

The LLC cells, breast cancer cell line (4T1), and hepatocellular carcinoma cells (CP20) were seeded into 96-well flat bottomed plates ($4 \times 10^3$ cells per well). Drugs or SACNs were added at equivalent Pt concentrations and incubated for 48 h. Viability was quantified using the Cell-Titer 96 Aqueous One Solution™ reagent. Cellular apoptosis was quantified using Annexin-V-Alexa Fluor™ 488 conjugate and propidium iodide staining followed by FACS.

SACN Internalization Study.

The 4T1 cells were seeded on glass cover-slips and treated with FITC-encapsulated SACNs for a time-course ranging from 30 min to 18 h. At the indicated times, cells were washed twice in PBS and incubated in LysoTracker™ red for 30 min at 37° C. Images taken in three random fields were captured at using an inverted epifluorescence deconvolution microscope (Nikon). To study the role of endocytosis in SACN internalization, the cells were incubated at 4° C. or pretreated with endocytosis inhibitors.

In Vivo Murine 4T1 Breast Cancer Model.

The 4T1 breast cancer cells ($3 \times 10^5$) were implanted subcutaneously in the flanks of 4-wk-old BALB/c mice. The drug therapy consisted of intravenous administration of SACNs (1 mg/kg and 3 mg/kg equivalent Pt dose), cisplatin (1 mg/kg and 3 mg/kg equivalent Pt dose), and carboplatin (3 mg/kg equivalent Pt dose). PBS (100 µL) by tail-vain injection was used as a control for drug treatment. Treatment was started on day 9 postimplantation, and administered every alternate day till day 13. The tumor volumes and body weights were monitored on a daily basis. The tumor volume was calculated by using the formula, $L \times B^2$.

Transgenic Ovarian Cancer Tumor Model.

Ovarian adenocarcinomas were induced in genetically engineered K-ras$^{LSL/+}$/Pten$^{fl/fl}$ mice via intrabursal delivery of adenovirus carrying Cre recombinase. Tumor cells were engineered to express luciferase once activated by Adeno-Cre, to make tumor imaging feasible before and after drug treatment. The drug therapy consisted of tail vein administration of SACNs (3 mg/kg equivalent Pt dose), cisplatin (3 mg/kg equivalent Pt dose), or PBS (100 µL). Each animal was dosed three times over the course of treatment given every alternate day. Treatment efficacy was quantified by examining the fold increase in bioluminescence of the posttreatment signal compared with baseline.

Biodistribution of SACNs.

Tumor-bearing animals were treated as described earlier. Organs were harvested, weighed, and dissolved in concentrated $HNO_3$. To these mixtures 30% (vol/vol) $H_2O_2$ was added; the resulting solutions were stirred for 24 h at room temperature and then heated for another 12 h to evaporate the liquids. All solid residues were redissolved in 1 mL water and then amount of platinum was measured by inductive-coupled plasma-atomic absorption spectrometry/MS.

Histopathology.

The tissues were fixed in 10% formalin, paraffin-embedded, and sectioned at the Harvard Medical School Core Facility. Tumor and kidney paraffin sections were deparaffinized and stained with a standard TMR red fluorescent TUNEL kit following the manufacturer's protocol (In Situ Cell Death Detection Kit™, TMR-Red; Roche). The kidney sections were also immunolabeled for KIM1 expression. Images were obtained using a Nikon Eclipse TE2000™ fluorescence microscope equipped with red filter.

Supplemental Materials and Methods:

All reactions were performed under inert conditions unless otherwise indicated. All commercially obtained compounds were used without further purification. Dichloromethane (DCM), dry DCM, methanol, cholesteryl chloroformate, cholesterol, ethylenediamine, succinic anhydrite, silver nitrate, sodium sulfate, pyridine, cisplatin, L-α-phosphatidylcholine (PC), sephadex G25, FITC, and 1,2-phenylenediamine were bought from Sigma-Aldrich; 1,2-Distearoyl-sn-Glycero-3-Phosphoethanolamine-N-[Amino (Polythylene Glycol) 2000] (DSPE-PEG) and the mini handheld Extruder kit (including 0.2 m Whatman Nucleopore Track-Etch Membrane™, Whatman filter supports, and 1.0 mL Hamiltonian syringes) were bought from Avanti Polar Lipids. Anhydrous solvent dimethylformamide (DMF) was supplied by Acros Organics. Phosphotungstic Acid was from Ted Pella. Analytical TLC was performed using precoated silica gel aluminum sheets 60 F254 bought from EMD Laboratories. Spots on the TLC plates were visualized using alkanine permanganate or 6% ninhydrin solution in acetone. 1H NMR (300 MHz) and 13C NMR (75 MHz) spectra were obtained on a Varian Mercury 300™ spectrophotometer. The chemical shifts are expressed in parts per million (ppm) using suitable deuterated NMR solvents with reference to TMS at 0 ppm. MTS reagent was supplied by Promega. The cell viability assay and release kinetic data were plotted using GraphPad Prism™ software. Each sample was repeated at least in triplicate.

Synthesis of Cholesterol-Ethylenediamine Conjugate.

For synthesis of cholesterol-ethylenediamine conjugate, 1,044 µL (15.58 mmol, 14 equiv) of ethylene diamine (compound 2) was dissolved in 5.0 mL anhydrous DCM followed by cooling down to 0-5° C. with ice. Next, 500.0 mg (1.113 mmol, 1.0 equiv) of cholesteryl chloroformate was dissolved in 5.0 mL anhydrous DCM and was added to the reaction mixture drop-wise over a period 15 min with vigorous stirring, and was continued overnight until it came to room temperature. The reaction was worked up using water (50 mL×3) and DCM (50 mL), followed by saturated brine water wash. The organic layer was dried over anhydrous sodium sulfate and evaporated with the help of a rotary evaporator. Light yellow colored clear oily product (compound 3) was separated with 99.1% yield. 1H-NMR (300 MHz) δ (ppm)=5.37 (s, 1H), 5.06 (S, 1H), 4.49 (bs, 1H), 3.22-3.20 (m, 2H), 2.82-2.81 (m, 2H), 2.34-2.26 (m, 2H), 2.02-1.83 (m, 6H), 1.54-0.84 (m, 37H). 13C-NMR (75 MHz) δ (ppm)=156.7, 140.1, 122.7, 74.5, 56.9, 56.3, 50.2, 42.5, 42.0, 39.9, 39.7, 38.8, 37.2, 36.8, 36.4, 36.0, 32.1, 28.5, 28.4, 24.5, 24.1, 23.1, 22.8, 21.3, 19.6, 18.9, 12.1.

Synthesis of Cholesterol-Ethylenediamine-Succinic Acid Conjugate.

For synthesis of cholesterol-ethylenediamine-succinic acid conjugate, 350 mg (0.74 mmol, 1 equiv) of compound 3 was dissolved in 5.0 mL anhydrous DCM. To this mixture, 370.0 mg (3.7 mmols, 5 equiv) of succinic anhydride and 2 mL of pyridine were added. The stirring was continued for 24 h followed by work up in 0.1 N HCl and DCM several times. The organic layer was dried over sodium sulfate and evaporated to get white amorphous solid compound (compound 5). Yield: 95%. 1H-NMR (300 MHz) δ (ppm)=7.72-7.70 (m, 1H), 7.54-7.53 (m, 1H), 5.37 (s, 1H), 5.07 (s, 1H), 4.49 (bs, 1H), 4.22-4.19 (m, 2H), 3.36-3.30 (m, 4H), 2.68-2.33 (m, 4H), 2.02-1.83 (m, 6H), 1.54-0.84 (m, 37H). 13C-NMR (75 MHz) δ (ppm)=174.5, 174.2, 156.3, 140.4, 122.4, 74.5, 56.9, 56.4, 50.1, 42.5, 40.9, 39.3, 36.7, 36.9, 36.0, 30.6, 29.8, 29.4, 28.4, 28.1, 23.3, 23.0, 19.1, 12.0.

Synthesis of Aquated Cisplatin $[Pt(NH3)2(OH2)2]2+$. For synthesis of aquated cisplatin $[Pt(NH3)2(OH2)2]2+$, 50 mg (0.166 mmol, 1 equiv) of cisplatin was partially dissolved in 10.0 mL of H2O. To this mixture, 28.0 mg (0.166 mmol, 1 equiv) of silver nitrate was added and the resulting reaction mixture was stirred at room temperature for 24 h. It looked milky white and silver chloride was removed by centrifuging at 25,000×g for 1 h. Finally, the aquated cisplatin (compound 6) was obtained by filtration through 0.2 µm filter.

Synthesis of Cholesterol-Cisplatin Conjugate.

For synthesis of cholesterol-cisplatin conjugate (7), 200 mg (0.35 mmol, 1.0 equiv) of compound 5 was dissolved in 5.0 mL DMF. To this mixture, 20.0 mL of aquated cisplatin (compound 6) (conc 5.0 mg/mL, 1.0 equiv) was added and stirred for 24 h. The solvent was evaporated using a lyophilizer. The dried product (compound 7) was purified using a 500-Da molecular weight cutoff (MWCO) dialysis membrane for 24 h followed by lyophilization. 195Pt-NMR: δ (ppm)=−1,621.497 (s).

General Procedure of Synthesizing Self-Assembling Cholesterol-Succinic Acid-Cisplatinum II-Based Nanoparticles.

The general procedure of synthesizing self-assembled cholesterol-succinic acid-cisplatinum II-based nanoparticles (SACNs) is as follows: 10.0 mg of PC, 5.0 mg cholesterol-cisplatin conjugate (7), and 1.0 mg of DSPE-PEG were dissolved in 10.0 mL DCM. Solvent was evaporated into a thin and uniform lipid-drug film using a rotary evaporator. The lipid-drug film was then hydrated with 1.0 mL H2O for 1 h at 60° C. The hydrated nanoparticles looked light yellow to white with little viscous texture. This mixture was passed although Sephadex G-25 column and extruded at 65° C. to obtain sub-200 nm particles.

General Method of Pt(II) Quantification in SACNs.

A measured amount of the SACNs was heated at 100° C. in 1.2 mg/mL concentration of 1,2-phenylenediamine in DMF for 2 h. Pt(II) amount was calculated by UV-VIS spectrophotometry by using standard absorbance vs. concentration curve drawn at wave-length λ=706 nm (Shimadzu 2450). This result was validated using an inductively coupled plasma-atomic absorption spec-troscopy (ICP-AAS)-based method.

Release Kinetics of Pt(II) from Nanoparticle at Different pH.

Concentrated drug-loaded nanoparticles were suspended in buffer (pH=5.5 and 8.5) and sealed in a dialysis membrane (MWCO=500 Da; Spectrum Lab). The dialysis bags were incubated in 30 mL PBS buffer at room temperature with gentle shaking. A 500-µL portion of the aliquot was collected from the incubation medium at predetermined time intervals, and the released drug was quantified by UV-VIS spectrophotometer (Shimadzu 2450™) and ICP-AAS.

Sample Preparation for Cryo-Transmission Electron Microscopy.

The sample was preserved in vitrified ice supported by holey carbon films on 400 mesh copper grids. The sample was prepared by applying 3 µL of sample suspension to a cleaned grid, blotting away with filter paper and immediately proceeding with vitrification in liquid ethane. Grids were stored under liquid nitrogen until transferred to the electron microscope for imaging. Electron microscopy was performed using an FEI Tecnai T12™ microscope, operating at 120 KeV equipped with an FEI Eagle 4K×4K CCD camera. Vitreous ice grids were transferred into the electron microscope using a cryostage that maintains the grids at a temperature below −170° C. Images of the grid were acquired at multiple scales to assess the overall distribution of the specimen. After identifying potentially suitable target areas for imaging at lower magnification, high magnification images were acquired at nominal magnification of 52,000× (0.21 nm/pixel) and 21,000× (0.50 nm/pixel). Images were acquired at a nominal underfocus of −5 µm (21,000×) and −4 µm (52,000×) at electron doses of ~10-15 e/A° 2.

Cell Viability Assay.

The Lewis lung carcinoma (LLC) cells, breast cancer cell line (4T1), and hepatocellular carcinoma cells (CP20) were purchased from American Type Culture Collection. LLC cells and CP20 cells were cultured in DMEM and 4T1 cells were cultured in RPMI medium 1640-supplemented with 10% FBS, 50 unit/mL penicillin, and 50 unit/mL streptomycin. Trypsinized cultured LLC, 4T1, and CP20 cells were washed twice with PBS and seeded into 96-well flat-bottomed plates (4×103 cells per well). Free drugs and SACNs were added at appropriate concentrations (0.01, 0.1, 1, 10, 20, 50 µM Pt concentration). The plates were then incubated for 48 h in a 5% CO2 atmosphere at 37° C. The cells were washed and incubated with 100 µL phenol-red free medium (without FBS) containing 20 µL of the Cell-Titer 96 Aqueous One Solution™ reagent (Promega). After 2 h incubation in 5% CO2 atmosphere at 37° C., the absorbance in each well was recorded at 490 nm using an Epoch (BioTek™) plate reader. Results were quantified by subtracting the blank value from each value then normalizing against the control values and results were analyzed by using Prism™ software (GraphPad). Data shown are mean±SE of n=3.

Synthesis of FITC-Labeled SACNs.

For synthesis of FITC-labeled SACNs, 10.0 mg of PC, 5.0 mg of cholesterol-cisplatin conjugate 7, 1.0 mg of DSPE-PEG, and 1 mg of FITC were dissolved in 10.0 mL DCM. Solvent was evaporated into a thin and uniform lipid-drug film with the help of a rotary evaporator. The lipid-drug film was hydrated with 1.0 mL H2O for 2 h at 60° C. The hydrated nanoparticles appeared light yellow to white with little viscous texture. The mixture was passed although Sephadex G-25 column and extruded at 65° C. in dark to obtain sub 200-nm particles.

FITC-SACN Internalization Study.

The 4T1 or 7404-CP20 cells were seeded on glass coverslips in 24-well plates until subconfluent, and then treated with FITC-encapsulated SACNs for a time-course ranging from 30 min to 18 h. At the indicated times, cells were washed twice in PBS and incubated in LysoTracker Red™ (Ex: 577 nm; Em: 590 nm) for 30 min at 37° C. Cells were then washed again, fixed in 4% paraformaldehyde, then treated with DAPI (Ex: 350 nm; Em: 470 nm) for 30 s, and mounted using Prolong Gold™ antifade reagent (Invitrogen). Images taken in three random fields were captured at 40× using an inverted microscope (Nikon) equipped with UV, blue, and green filters to visualize DAPI, FITC, and LysoTracker red fluorescence, respectively. Cells incubated either only FITC encapsulated CNP or Lyso-Tracker red served as negative controls. Pharmacological inhibitors are often used to study endocytic pathways. We used Chlorpromazine (25 µM) as Clathrin-mediated endocytosis inhibitor, Nystatin (25 µg/mL) as caveolae-mediated endocytosis inhibitor, and Cytochalasin D (5 µg/mL) as macropinocytosis/phagocytosis inhibitor. Cells were pretreated with the inhibitors for 2 h before incubation with the FITC-SACNs for 4 h, following which they were imaged after being processed as de-scribed earlier. In other studies the cells were incubated at 4° C. to block energy-dependent endocytosis, as described by Drin et al. (1)

Quantification of Intracellular Pt In Vitro in 7404-CP20 Cells.

For quantification of intracellular Pt in vitro in 7404-CP20 cells, 5×105 CP20 cells were plated in 100-mm cell culture dish. When cells became around 70% confluent, they were serum-deprived for 6 h before the addition of the drugs. Cells were incubated with either 20 µM of free cisplatin or SACN at 37° C. or same dose of SACN at 4° C. to inhibit energy-dependent internalization. After that, drug-containing media was removed and cells were washed three times using cold PBS. Cell numbers from each dish were counted following trypsinization, and then lysed overnight in 70% nitric acid. Nitric acid was then evaporated and amount of Pt was measured by ICP-MS after appropriate dilutions in 5% nitric acid.

FACS Analysis of Apoptosis.

The 4T1 cells were grown in six-well plates incubated in the presence of SACNs or free cisplatin or free carboplatin at 1 µM concentration at 37° C. for 24 h. After 24 h, the cells were washed with PBS and collected at 0° C. The cells were then treated with Annexin-V-Alexa Fluor 488™ conjugate (Molecular Probes, Invitrogen) and incubated in the dark, at room temperature, for 15 min. The cells were then washed with PBS and incubated with propidium iodide (PI) solution (50 g/mL; Sigma) containing RNase (1 mg/mL; Sigma). The cell suspension were then transferred to FACS tubes and analyzed for Annexin-V/PI staining on a BD FACS Calibur™ instrument. Data were analyzed using a CellQuest-Pro™ software (BD Biosciences).

In Vivo Marine 4T1 Breast Cancer Model.

The 4T1 breast cancer cells (3×105) were implanted subcutaneously in the flanks of 4-wk-old BALB/c mice (weighing 20 g; Charles River Laboratories). The drug therapy was started on day 9. The drug therapy consisted of administration of SACNs (1 mg/kg and 3 mg/kg), free cisplatin (1 mg/kg and 3 mg/kg), and free carboplatin (3 mg/kg) (administered by tail-vain injection). PBS (100 µL) administered by tail-vain injection was used as a control for drug treatment. The tumor volumes and body weights were monitored on a daily basis. The tumor volume was calculated by using the formula, L×B2, where the longest diameter was considered as L and the shortest diameter as measured using a vernier caliper as B. The animals were killed when the average tumor volume of the control exceeded 2,000 mm3 in the control group. The tumors were harvested immediately following sacrifice and stored in 10% formalin for further analysis. All animal procedures were approved by the Harvard Institutional Use and Care of Animals Committee.

In Vivo Murine Ovarian Cancer Tumor Model.

Ovarian adenocarcinomas were induced in genetically engineered K-rasLSL/+/Ptenfl/fl mice via intrabursal delivery of adenovirus-carrying Cre recombinase. Tumor cells were engineered to express luciferase once activated by Adeno-Cre, to make tumor imaging feasible before and after drug treatment. Once mice developed medium-to-large tumors they were placed into one of three treatment groups (control, cisplatin 3 mg/kg, and SACNs), with all drugs administered intravenously via tail vein. The dose of SACNs was selected to be equivalent in Pt content as 3 mg/kg of cisplatin. The animals were injected with the drugs three times over a 6-d period with a 1-d interval between the dosings. Tumor imaging in vivo was performed with the IVIS Lumina II Imaging System™. Quantification of bioluminescence was achieved by using the Living Image Software 3.1™ (Caliper Life Sciences). Mice received 150 mg/kg of D-luciferin firefly potassium salt via intraperitoneal injection before imaging. Five minutes postluciferin injection, animals were anesthetized in a 2.5% isoflurane induction chamber where they were kept under anesthesia by a manifold supplying isoflurane and their body temperature was maintained by a 37° C. temperature stage. Bioluminescent signal was collected 15 min after luciferin administration for an exposure time of 30 s. Images were taken a day before treatment (day 0, baseline), in the middle of the treatment cycle, and 1 d following the final treatment. Treatment efficacy was quantified by examining the fold-increase in bioluminescence of the posttreatment signal compared with baseline. Statistical analysis of the toxicity data were analyzed using a one-way ANOVA test with the Prism 5™ software.

Biodistribution of Cisplatin and SACNs.

After the in vivo experiments, the animals were killed and the organs were harvested. The organs were then weighed and dissolved in concentrated $HNO_3$ (approximately 10 mL) by shaking for 24 h at room temperature and then heating at 100° C. for 12 h. To these mixtures 30% $H2O2$ was added, the resulting solutions were stirred for 24 h at room temperature, and then heated for another 12 h to evaporate the liquids. All solid residues were redissolved in 1 mL water and then amount of platinum was measured by inductively coupled plasma-spectrometry.

Platinum II can react with nitrogen, sulfur, and oxygen residues in other biomolecules, such as plasma proteins. As a result of these reactions, a variety of platinum species may be present in the body after treatment with cisplatin. This protocol does not distinguish platinum that may have become deactivated by reactions with plasma proteins from active drug, and only quantifies the total Pt concentrations at defined time point. We anticipate that such interactions will be normalized when we make comparisons between the SACN-treated groups and cisplatin-treated animals. However, there is a possibility that the preferential release of Pt (II) from SACNs in acidic vs. physiological pH might translate into lower deactivation by coordination with Drin G, Cottin S, Blanc E, Rees A R, Temsamani J (2003) Studies on the internalization mechanism of cationic cell-penetrating peptides. J Biol Chem 278:31192-31201. plasma proteins, and greater concentration of activated Pt (II) in the tumor.

Histopathology and TUNEL Assay (Apoptotic Assay).

The tissues were fixed in 10% formalin, paraffin-embedded, and sectioned at the Harvard Medical School Core Facility. Tumor and kidney paraffin sections were deparaffinized and stained with standard TMR red fluorescent TUNEL kit following the manufacturer's protocol (In Situ Cell Death Detection Kit™, TMR-Red; Roche). Images were obtained using a Nikon Eclipse TE2000 fluorescence microscope equipped with red filter.

Immunohistochemical Analysis of Kidney Injury Molecule-1.

Immunohistochemical analysis was performed on formalin-fixed, paraffin-embedded tissue sections. Briefly, paraffin embedded tissue sections were deparaffinized, rehydrated, and antigen retrieval was carried out in 0.1 M citrate buffer (pH 6.0) for 20 min in a pressure cooker. The slides were then washed in PBS solution and incubated in 3% BSA solution for 30 min following which they were incubated with goat anti-mouse kidney injury molecule-1 (Kim-1) antibody (R&D Systems), at 1:500 dilution for 60 min. Slides were washed in PBS solution and incubated in anti-goat secondary antibody (1:200 dilution; R&D Systems) for another 30 min. Staining of the tissue sections were done using VECTASTAIN ABC™ kit (Vector Laboratories) for 30 min followed by counterstaining with hematoxylin. Pictures were taken using Nikon ECLIPSE 90i™ microscope.

REFERENCES

1. Jemal A, Center M M, DeSantis C, Ward E M (2010) Global patterns of cancer incidence and mortality rates and trends. Cancer Epidemiol Biomarkers Prev 19:1893-1907
2. World Health Organization (2008) WHO Cancer Report. Available at http://www.who.int/cancer/en/. Accessed Jun. 12, 2012.
3. Ferrari M (2005) Cancer nanotechnology: Opportunities and challenges. Nat Rev Cancer 5:161-171,
4. Yuan F, et al. (1994) Microvascular permeability and interstitial penetration of sterically stabilized (stealth) liposomes in a human tumor xenograft. Cancer Res 54:3352-3356.
5. Northfelt D W, et al. (1996) Doxorubicin encapsulated in liposomes containing surface-bound polyethylene glycol: Pharmacokinetics, tumor localization, and safety in patients with AIDS-related Kaposi's sarcoma. J Clin Pharmacol 36:55-63.
6. Desai N, et al. (2006) Increased antitumor activity, intratumor paclitaxel concentrations, and endothelial cell transport of cremophor-free, albumin-bound paclitaxel, ABI-007, compared with cremophor-based paclitaxel. Clin Cancer Res 12:1317-1324.
7. Zamboni W C (2008) Concept and clinical evaluation of carrier-mediated anticancer agents. Oncologist 13:248-260,
8. Kelland L (2007) The resurgence of platinum-based cancer chemotherapy. Nat Rev Cancer 7:573-584.
9. Avgoustakis K, et al. (2002) PLGA-mPEG nanoparticles of cisplatin: in vitro nanoparticle degradation, in vitro drug release and in vivo drug residence in blood properties. J Control Release 79:123-135.
10. Haxton K J, Burt H M (2009) Polymeric drug delivery of platinum-based anticancer agents. J Pharm Sci 98:2299-2316.
11. Zamboni W C, et al. (2004) Systemic and tumor disposition of platinum after administration of cisplatin or STEALTH liposomal-cisplatin formulations (SPI-077 and SPI-077 B103) in a preclinical tumor model of melanoma. Cancer Chemother Pharmacol 53:329-336.
12. White S C, et al. (2006) Phase II study of SPI-77 (sterically stabilised liposomal cisplatin) in advanced non-small-cell lung cancer. Br J Cancer 95:822-828.
13. Choi H S, et al. (2007) Renal clearance of quantum dots. Nat Biotechnol 25:1165-1170.
14. Madias N E, Harrington J T (1978) Platinum nephrotoxicity. Am J Med 65:307-314.
15. Davies M S, Berners-Price S J, Hambley T W. (2000) Slowing of cisplatin aquation in the presence of DNA but not in the presence of phosphate: improved understanding of sequence selectivity and the roles of monoaquated and diaquated species in the binding of cisplatin to DNA. Inorg Chem 39:5603-5613.
16. Knox R J, Friedlos F, Lydall D A, Roberts J J (1986) Mechanism of cytotoxicity of anticancer platinum drugs: Evidence that cis-diaminedichloroplatinum(II) and cis-diamine-(1,1-cyclobutanedicarboxylato)platinum(II) differ only in the kinetics of their interaction with DNA. Cancer Res 46:1972-1979.
17. Los G, et al. (1991) Cellular pharmacokinetics of carboplatin and cisplatin in relation to their cytotoxic action. Biochem Pharmacol 42:357-363.
18. Paraskar A, et al. (2011) Rationally engineered polymeric cisplatin nanoparticles for improved antitumor efficacy. Nanotechnology 22:265101.
19. Paraskar A S, et al. (2010) Harnessing structure-activity relationship to engineer a cisplatin nanoparticle for enhanced antitumor efficacy. Proc Natl Acad Sci USA 107:12435-12440.
20. Sengupta S, et al. (2005) Temporal targeting of tumour cells and neovasculature with a nanoscale delivery system. Nature 436:568-572.
21. Shen D W, et al. (1995) Characterisation of high-level cisplatin-resistant cell lines established from a human hepatoma cell line and human KB adenocarcinoma cells: Cross-resistance and protein changes. Br J Cancer 71:676-683.
22. Sato N, et al. (2000) Loss of heterozygosity on 10q23.3 and mutation of the tumor suppressor gene PTEN in benign endometrial cyst of the ovary: possible sequence progression from benign endometrial cyst to endometrioid carcinoma and clear cell carcinoma of the ovary. Cancer Res 60:7052-7056.
23. Cuatrecasas M, et al. (1998) K-ras mutations in nonmucinous ovarian epithelial tumors: a molecular analysis and clinicopathologic study of 144 patients. Cancer 82:1088-1095.
24. Dinulescu D M, et al. (2005) Role of K-ras and Pten in the development of mouse models of endometriosis and endometrioid ovarian cancer. Nat Med 11:63-70.
25. Lehn J M. (1995) *Supramolecular Chemistry: Concepts and Perspectives* (VCH, New York).
26. Lehn J M. (2002) Toward complex matter: Supramolecular chemistry and self-organization. Proc Natl Acad Sci USA 99:4763-4768.
27. Chen K J, et al. (2011) A small MRI contrast agent library of gadolinium(III)-encapsulated supramolecular nanoparticles for improved relaxivity and sensitivity. Biomaterials 32:2160-2165.
28. Chen K J, et al. (2012) The therapeutic efficacy of camptothecin-encapsulated supramolecularnanoparticles. Biomaterials 33:1162-1169.
29. Yao X, et al. (2007) Cisplatin nephrotoxicity: A review. Am J Med Sci 334:115-124.
30. Bedu-Addo F K, et al. (1996) Interaction of polyethyleneglycol-phospholipid conjugates with cholesterol-phosphatidylcholine mixtures: Sterically stabilized liposome formulations. Pharm Res 13:718-724.
31. Matsumori N, et al. (2004) An amphotericin B-ergosterol covalent conjugate with powerful membrane permeabilizing activity. Chem Biol 11:673-679.
32. Torchilin V P (2005) Recent advances with liposomes as pharmaceutical carriers. Nat Rev Drug Discov 4:145-160.
33. Mosqueira V C, et al. (2001) Relationship between complement activation, cellular uptake and surface physicochemical aspects of novel PEG-modified nanocapsules. Biomaterials 22:2967-2979.
34. Vaidya V S, et al. (2010) Kidney injury molecule-1 outperforms traditional biomarkers of kidney injury in preclinical biomarker qualification studies, Nat Biotechnol 28:478-485.
35. Radermaker-Lakhai J M, et al. (2004) A Phase I and pharmacological study of the platinum polymer AP5280 given as an intravenous infusion once every 3 weeks in patients with solid tumors. Clin Cancer Res 10:3386-3395.
36. Lin X, et al. (2004) Improved targeting of platinum chemotherapeutics. the antitumor activity of the HPMA copolymer platinum agent AP5280 in murine tumour models. Eur J Cancer 40:291-297.
37. Sugano K, et al. (2010) Coexistence of passive and carrier-mediated processes in drug transport. Nat Rev Drug Discov 9:597-614.
38. Vercauteren D, et al. (2010) The use of inhibitors to study endocytic pathways of gene carriers: Optimization and pitfalls. Mol Ther 18:561-569.
39. Jian W, et al. (2009) Preclinical antitumor and antiangiogenic activity of a metronomic schedule of cisplatin against human transitional cell carcinoma (TCC) J Clin Oncol 27:e16018.

What is claimed herein:

1. A composition comprising a conjugate, the conjugate comprising a chemotherapeutic agent conjugated to cholesterol, wherein the chemotherapeutic agent is a PI3K inhibitor.

2. The composition of claim 1, wherein the conjugate is of Formula (I) or Formula (II):

FORMULA I

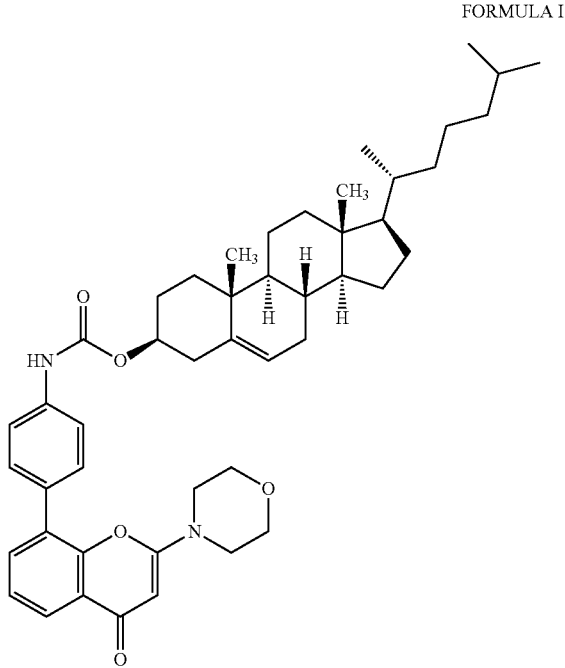

FORMULA II

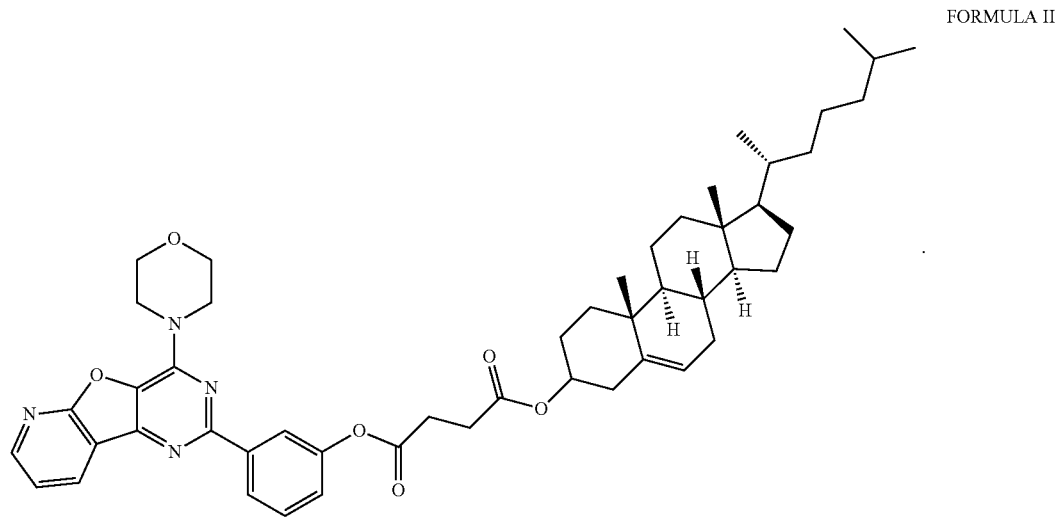

3. The composition of claim 1, wherein the composition further comprises a lipid in addition to the conjugate.

4. The composition of claim 3, wherein the lipid is a lipid conjugated with polyethylene glycol (PEG).

5. The composition of claim 4, wherein the PEG conjugated lipid is selected from the group consisting of:
PEG conjugated diacylglycerols and dialkylglycerols; PEG-conjugated phosphatidylethanolamine and phosphatidic acid; PEG conjugated ceramides; PEG conjugated dialkylamines; PEG conjugated 1,2-diacyloxy-propan-3-amines; 1,2-distearoyl-sn-glycem-3-phosphoethanolamine-N-[amino(polyethylene glycol)-2000] (DSPE-PEG2000); and any combinations thereof.

6. The composition of claim 1, wherein the composition further comprises a phospholipid.

7. The composition of claim 6, wherein the phospholipid is selected from the group consisting of:
phosphatidyl cholines; phosphatidyl cholines with acyl groups having 6 to 22 carbon atoms; phosphatidyl ethanolamines; phosphatidyl inositols; phosphatidic acids; phosphatidyl serines; sphingomyelin; phosphatidyl glycerols; phosphatidylcholine; phosphatidylglycerol; lecithin; β,γ-dipalmitoyl-α-lecithin; sphingomyelin; phosphatidylserine; phosphatidic acid; N-(2,3-di(9-(Z)-octadecenyloxy))-prop-1-yl-N,N,N-trimethylammonium chloride; phosphatidylethanolamine; lysolecithin; lysophosphatidylethanolamine; phosphatidylinositol; cephalin; cardiolipin; cerebrosides; dicetylphosphate; dioleoylphosphatidylcholine; dipalmitoylphosphatidylcholine; dipalmitoylphosphatidylglycerol; dioleoylphosphatidylglycerol; palmitoyl-oleoyl-phosphatidylcholine; distearoyl-phosphatidylcholine; stearoyl-palmitoyl-phosphatidylcholine; di-palmitoyl-phosphatidylethanolamine; di-stearoyl-phosphatidylethanolamine; di-myrstoyl-phosphatidylserine; di-oleyl-phosphatidylcholine; dimyristoyl phosphatidyl choline (DMPC); dioleoyl-phosphatidylethanolamine (DOPE); palmitoyloleoyl-phosphatidylcholine (POPC); egg phosphatidylcholine (EPC); distearoylphosphatidylcholine (DSPC); dioleoylphosphatidylcholine (DOPC); dipalmitoylphosphatidylcholine (DPPC); dioleoylphosphatidylglycerol (DOPG); dipalmitoylphosphatidylglycerol (DPPG); -phosphatidylethanolamine (POPE); dioleoyl-phosphatidylethanolamine 4-(N-maleimidomethyl)-cyclohexane-1-carboxylate (DOPE-mal); L-a-phosphatidylcholine; and any combinations thereof.

8. The composition of claim 1, further comprising a targeting agent.

9. The composition of claim 8, wherein the targeting agent is selected from the group consisting of:
peptides; polypeptides; proteins; enzymes; peptidomimetics; glycoproteins; antibodies (monoclonal or polyclonal) and portions and fragments thereof; lectins; nucleosides; nucleotides; nucleoside and nucleotide analogues; nucleic acids; monosaccharides; disaccharides; trisaccharides; oligosaccharides; polysaccharides; lipopolysaccharides; vitamins; steroids; hormones; cofactors; receptors; receptor ligands and iRGD (amino acid sequence CRGDKGPDC (SEQ ID NO: 1)).

10. The composition of claim 1, wherein the composition further comprises an anticancer agent in addition to the conjugate.

11. The composition of claim 10, wherein the anticancer agent is selected from the group consisting of:
a platinum compound, paclitaxel; carboplatin; bortezomib; vorinostat; rituximab; temozolomide; rapamycin; an alkylating agent; cyclosphosphamide; an alkyl sulfonate; busulfan; improsulfan; piposulfan; an aziridine; an ethylenimine; a methylamelamine; an acetogenin; a camptothecin; a cryptophycin; a nitrogen mustard; a nitrosurea; an antibiotic; a enediyne antibiotic; a bisphosphonate; doxorubicin; a mitomycin; an antimetabolite; a folic acid analogue; a purine analog; a pyrimidine analog; an androgen; an anti-adrenal; an epothilone; a maytansinoid; a trichothecene; gemcitabine; 6-thioguanine; mercaptopurine; methotrexate; vinblastine; etoposide; ifosfamide; mitoxantrone; vincristine; vinorelbine; novantrone; teniposide; edatrexate; daunomycin; aminopterin; xeloda; ibandronate; irinotecan; a topoisomerase inhibitor; a retinoid; capecitabine; combretastatin; leucovorin; lapatinib; erlotinib; and a compound having the structure of formula (IV):

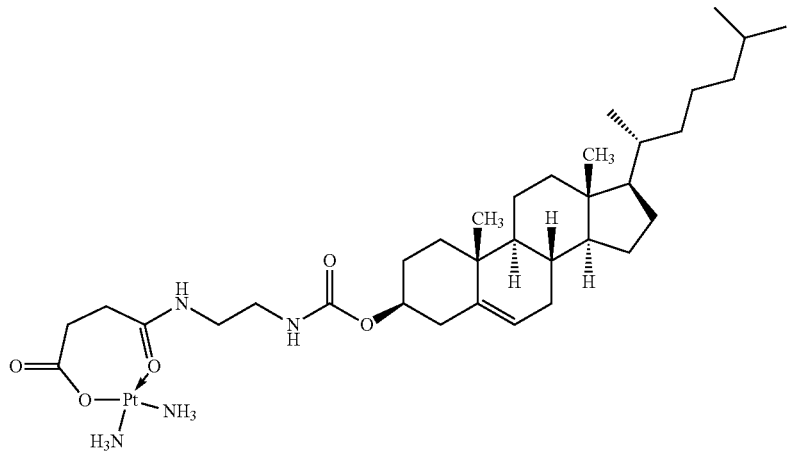

Formula IV

12. The composition of claim 1, wherein the composition comprises the conjugate, a PEG conjugated lipid, and a phospholipid.

13. The composition of claim 12, wherein the PEG conjugated lipid is DSPE-PEG2000 and the phospholipid is phosphatidylcholine.

14. A method of treating cancer, comprising, administering a composition of claim 1, to a subject in need of treatment for cancer wherein the cancer is selected from the group consisting of: breast cancer; ovarian cancer; glioma; gastrointestinal cancer; prostate cancer; carcinoma, lung carcinoma, hepatocellular carcinoma, testicular cancer; cervical cancer; endometrial cancer; bladder cancer; head and neck cancer; lung cancer; gastro-esophageal cancer, and gynecological cancer.

15. The method of claim 14, wherein the subject has been determined to have tumor cells with aberrant PI3K.

16. The composition of claim 1, wherein the PI3K inhibitor is selected from the group consisting of PI103; PI828; LY294002; wortmannin; demethoxyviridin; IC486068; IC87114; GDC-0941; perifosine; CAL101; PX-866; IPI-145; BAY 80-6946; BEZ235; P6503; TGR1202; SF1126; INK1117; BKM120; IL147; XL765; Palomid 529; GSK1059615; ZSTK474; PWT33597; TG100-115; CAL263; GNE-447; CUDC-907; and AEZS-136.

* * * * *

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Cys Arg Gly Asp Lys Gly Pro Asp Cys
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Ala Arg Ser Lys Asn Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Cys Gly Asn Lys Arg Thr Arg Gly Cys
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Arg Glu Lys Ala
1               5
```